(12) United States Patent
Onogi et al.

(10) Patent No.: US 8,765,941 B2
(45) Date of Patent: Jul. 1, 2014

(54) ANILINE DERIVATIVE HAVING ANTI-RNA VIRAL ACTIVITY

(75) Inventors: Hiroshi Onogi, Tokyo (JP); Masatoshi Hagiwara, Chiba (JP); Masaaki Suzuki, Aichi (JP); Hiroko Koyama, Gifu (JP); Takamitsu Hosoya, Kanagawa (JP); Toshiyuki Hiramatsu, Tokyo (JP)

(73) Assignee: Kino Pharma, Inc., Tokyo (JP)

( * ) Notice: Subject to any disclaimer, the term of this patent is extended or adjusted under 35 U.S.C. 154(b) by 542 days.

(21) Appl. No.: 12/934,206

(22) PCT Filed: Feb. 4, 2009

(86) PCT No.: PCT/JP2009/052253
§ 371 (c)(1),
(2), (4) Date: Sep. 23, 2010

(87) PCT Pub. No.: WO2009/119167
PCT Pub. Date: Oct. 1, 2009

(65) Prior Publication Data
US 2011/0059950 A1  Mar. 10, 2011

(30) Foreign Application Priority Data

Mar. 25, 2008 (JP) .................................. 2008-078728

(51) Int. Cl.
*C07D 225/02* (2006.01)
*C07D 401/00* (2006.01)
*C07D 401/12* (2006.01)
*A61K 31/395* (2006.01)
*C07D 213/83* (2006.01)
*C07D 405/12* (2006.01)
*A61K 31/55* (2006.01)
*A61K 31/00* (2006.01)
*A61K 31/4545* (2006.01)
*C07D 213/81* (2006.01)
*A61K 31/455* (2006.01)
*C07D 213/82* (2006.01)
*C07D 409/12* (2006.01)

(52) U.S. Cl.
CPC ............ *C07D 213/81* (2013.01); *A61K 31/395* (2013.01); *C07D 213/83* (2013.01); *C07D 405/12* (2013.01); *A61K 31/55* (2013.01); *A61K 31/00* (2013.01); *A61K 31/4545* (2013.01); *C07D 401/12* (2013.01); *A61K 31/455* (2013.01); *C07D 225/02* (2013.01); *C07D 213/82* (2013.01); *C07D 409/12* (2013.01)
USPC .......................................... 540/450; 540/481

(58) Field of Classification Search
None
See application file for complete search history.

(56) References Cited

U.S. PATENT DOCUMENTS

2004/0171603 A1   9/2004  Pato et al.
2007/0135367 A1   6/2007  Hagiwara et al.

FOREIGN PATENT DOCUMENTS

| CA | 2551602 | * | 7/2005 | ......... A61K 31/4409 |
| WO | 02/094796 A2 | | 11/2002 | |
| WO | 2005/063293 A1 | | 7/2005 | |

OTHER PUBLICATIONS

Fukuhara, Takeshi et al. "Utilization of host SR protein kinases and RNA-splicing machinery during viral replication," Proceedings of the National Academy of Sciences of the USA, Jul. 2006, pp. 11329-11333, vol. 103 No. 30.
International Search Report of PCT/JP2009/052253, mailing date Apr. 28, 2009.
Written Opinion of PCT/JP2009/052253, mailing date Apr. 28, 2009.

* cited by examiner

*Primary Examiner* — Noble Jarrell
(74) *Attorney, Agent, or Firm* — Westerman, Hattori, Daniels & Adrian, LLP

(57) ABSTRACT

Viruses, and particularly RNA viruses, have high mutation rates. Hence, antiviral agents that have been developed to date targeting protease or reverse transcriptase of viruses have quickly lost their effectiveness and resistant viruses have emerged. Also, in recent years, viral diseases caused by various new viruses such as SARS, avian influenza, and the hepatitis C have become social menaces. Therefore, the development of a novel antiviral agent that can cope with a virus resistant to an existing drug or a new virus and has a wide range of applications has been demanded. The present invention provides a novel anti-RNA viral agent and a method for use thereof. The present invention further provides an anti-RNA viral agent that is also effective against a new virus or a drug-resistant virus, and a method for use thereof.

2 Claims, 12 Drawing Sheets

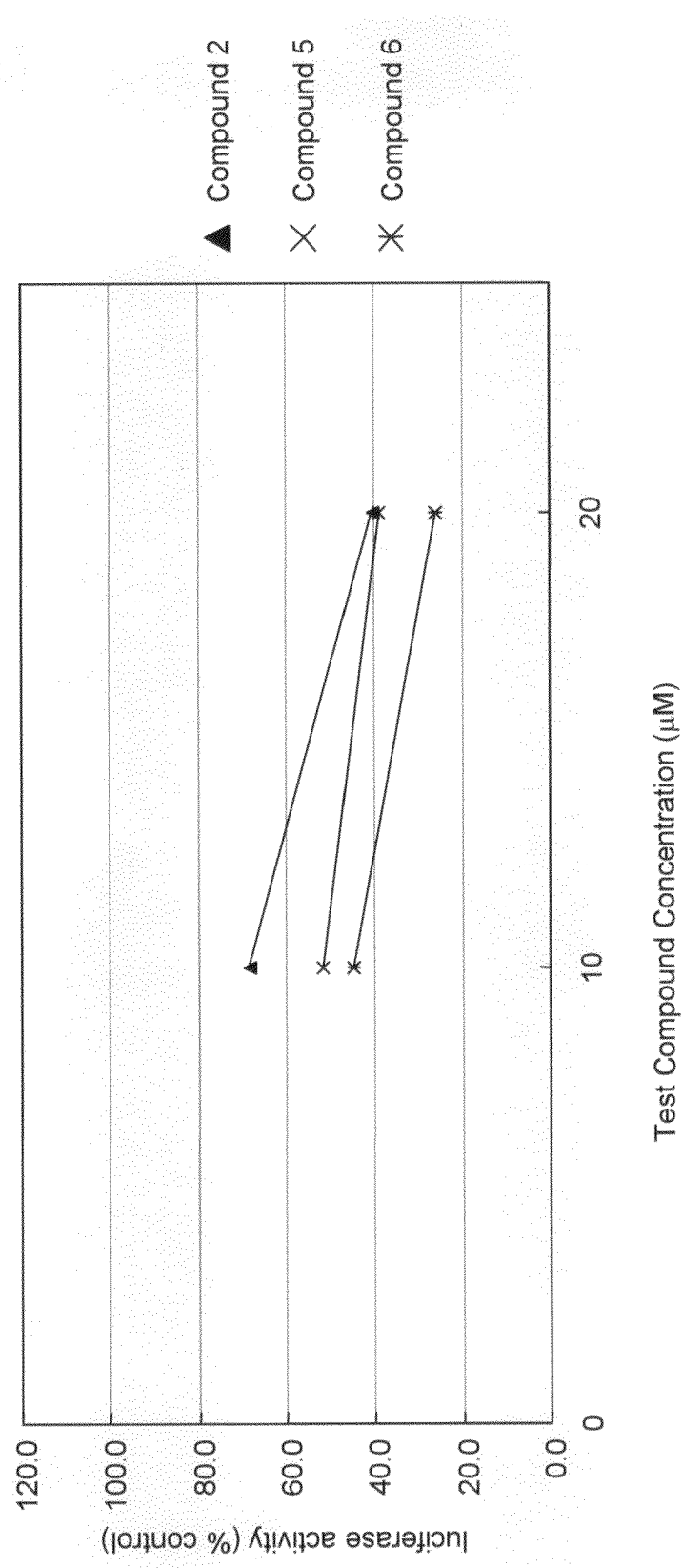

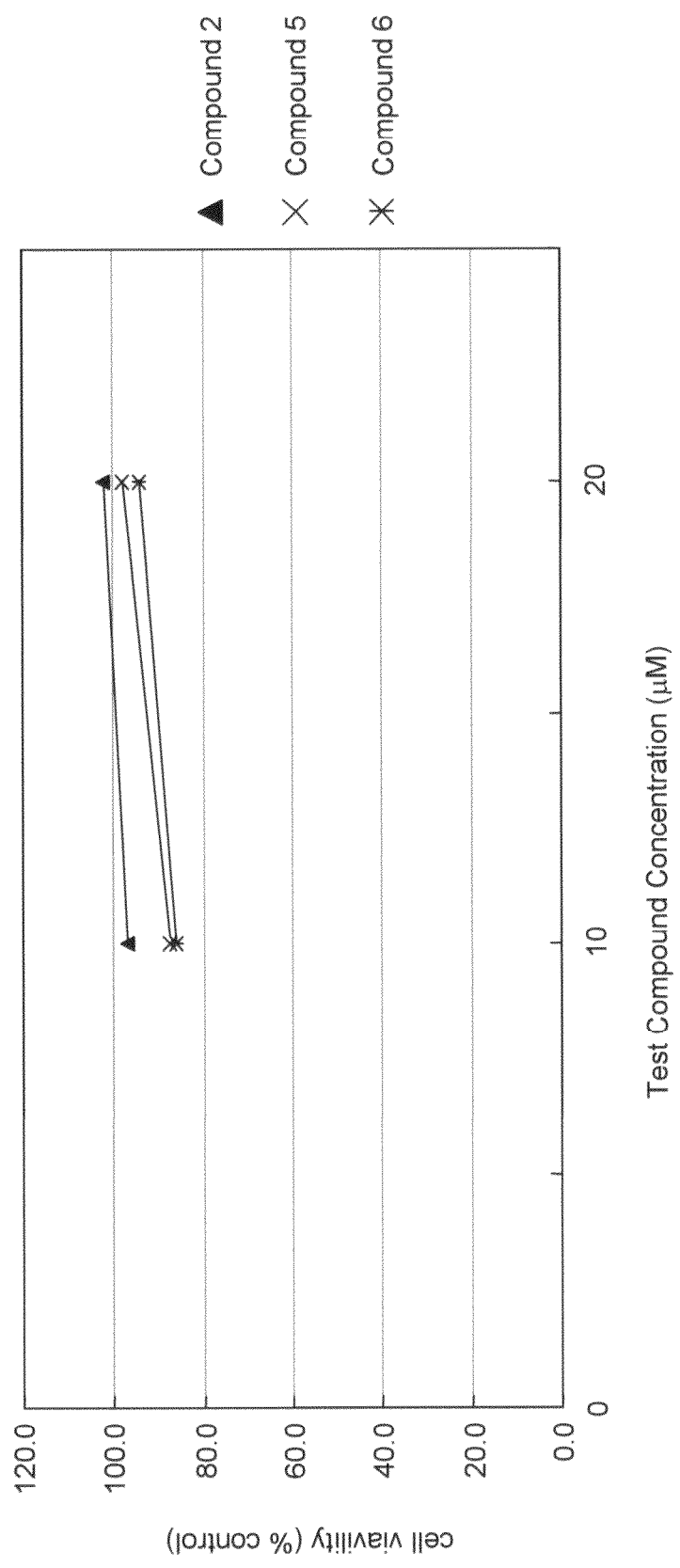

SEQUENCE LISTING

```
<160> NUMBER OF SEQ ID NOS: 4

<210> SEQ ID NO 1
<211> LENGTH: 23
<212> TYPE: DNA
<213> ORGANISM: Artificial
<220> FEATURE:
```

```
<223> OTHER INFORMATION: primer

<400> SEQUENCE: 1 agttttcac ggaggtggat ggg                                             23

<210> SEQ ID NO 2
<211> LENGTH: 23
<212> TYPE: DNA
<213> ORGANISM: Artificial
<220> FEATURE:
<223> OTHER INFORMATION: primer

<400> SEQUENCE: 2
gtccgggttc ttccaagact cta                                            23

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
acggatttgg tcgtattggg                                                20

<210> SEQ ID NO 4
<211> LENGTH: 24
<212> TYPE: DNA
<213> ORGANISM: Artificial
<220> FEATURE:
<223> OTHER INFORMATION: primer

<400> SEQUENCE: 4
gtagttgagg tcaatgaagg ggtc                                           24
```

ANILINE DERIVATIVE HAVING ANTI-RNA VIRAL ACTIVITY

TECHNICAL FIELD

The present invention relates to a compound inhibiting a kinase of a host cell involved in viral infection. The present invention particularly relates to an inhibitor for a kinase that controls viral protein translation. Furthermore, the present invention relates to an antiviral agent against RNA viruses belonging to the families Flaviviridae, Reoviridae, Paramyxoviridae, Orthomyxoviridae, Retroviridae, and the like, which comprises a kinase inhibitor as an active ingredient. In particular, the present invention relates to a compound effective in prevention or treatment of diseases caused by RNA viruses. Specifically, the present invention relates to a preventive or therapeutic agent for hepatitis C and a preventive or therapeutic agent for influenza virus infection.

BACKGROUND OF THE INVENTION

Infection of humans with miroorganisms has long been a matter of conventional concern. In particular, the risk of various infections to humans is further increasing with the development of modes of transportation and expansion of the living areas of people in recent years. Representative examples of therapeutic agents against infections include antibiotics. However, an antibiotic is a medicine that can exhibit its effects only when it inhibits the in vivo metabolic pathway of a pathogen. Nevertheless, viruses depend totally on host cells in terms of protein synthesis and energy production mechanisms and lack their own metabolic pathways. Hence, antibiotics cannot exhibit direct viral inhibitory effects. Therefore, infections caused by viruses rather than bacteria are currently becoming a threat.

Viruses are minute microorganisms having no cell structure, and they are broadly classified as DNA viruses or RNA viruses. There exist three modes of viral infection: acute infection with significant disintegration of host cells; persistent infection with clinical symptoms that remain at relatively minor levels but become chronic; and latent infection with viruses that remain in a state in which no observable viral protein synthesis takes place for a long time period, although cancer is induced in some cases.

Examples of an RNA virus causing a human disease include Japanese encephalitis virus, hepatitis C virus (HCV), and the like of the family Flaviviridae, Rotavirus and the like of the family Reoviridae, mumps virus, measles virus, and the like of the family Paramyxoviridae, influenza virus and the like of the family Orthomyxoviridae, and human immunodeficiency virus (HIV) and the like of the family Retroviridae.

Among such diseases, hepatitis C, which is caused by infection with hepatitis C virus, tends to be chronic. Once hepatitis C becomes chronic, it becomes a severe disease, with a high percentage of cases progressing to cirrhosis or liver cancer. An effective therapeutic method is strongly desired. Regarding influenza viruses, it is well known that pandemic outbreak thereof occurs every several years. It is also known that patients may die if the infection left untreated. Therefore, an urgent need is to provide the market with a remedy effective against influenza viruses.

Examples of an antiviral agent against an RNA virus include Amantadine, Zanamivir, Oseltamivir, and the like against influenza viruses, Zidovudine, Nevirapine, Ritonavir, and the like against HIV, and Ribavirin and the like against HCV.

However, currently used remedies against viral disease are still under development since they are problematic in terms of adverse reaction, effectiveness, and the like, as suggested. Also, another problem may arise such that a virus resistant to an antiviral agent considered to be effective appears. Therefore, development of a novel antiviral agent is still desired.

The present inventors have studied proteins involved in splicing regulation. In the course of this study, the present inventors have discovered that a group of compounds including compounds represented by the following formulae exhibit inhibitory activity against SRPK, which is a kinase and thus have antiviral effects, as disclosed in International Patent Publication Pamphlet WO2005/063293.

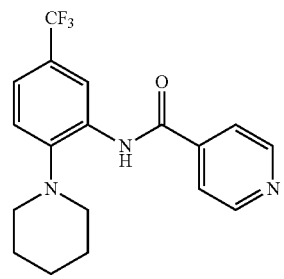 [SMILES: O=C(Nc1cc(C(F)(F)F)ccc1N1CCCCC1)c1ccncc1]

DISCLOSURE OF THE INVENTION

Problems to be Solved by the Invention

Viruses and particularly RNA viruses, have high mutation rates, so that existing antiviral agents that have been developed targeting viral protease, reverse transcriptase, and the like lose their effectiveness at high rates. Thus, development of an even more effective antiviral agent has been desired.

In particular, in recent years, viral diseases resulting from various novel viruses, such as SARS, avian influenza, and hepatitis C, have become societal menaces. Therefore, an object of the present invention is to develop a new antiviral agent with a wide range of applications, which can cope with viruses resistant to existing drugs or novel viruses.

Means for Solving the Problems

The present inventors have conventionally studied with focus on protein kinase of host cells involved in viral gene expression. In particular, as a result of synthesizing many compounds inhibiting protein kinase, which controls viral protein translation and then screening, the present inventors have discovered that compounds having the structure of the following formula I have excellent anti-viral activity.

Specifically, the present invention relates to an antiviral agent comprising a compound that inhibits protein kinase of host cells. The present invention particularly relates to a preventive or therapeutic agent for viral infection, which comprises a compound having the structure of formula I or a pharmaceutically acceptable salt thereof as an active ingredient. Furthermore, the present invention relates to a preventive or therapeutic agent for viral infection caused by an RNA virus and a method for using the agent.

More specifically, the present invention is characterized as follows.

[1] An antiviral agent comprising a compound that inhibits a protein kinase of a host cell as an active ingredient.

[2] The antiviral agent according to [1] above, wherein the protein kinase is a protein kinase of a host cell, which is activated by viral infection.

[3] The antiviral agent according to [1] or [2] above, wherein the protein kinase is a protein kinase of a host cell, which controls viral protein translation.

[4] The antiviral agent according to any one of [1] to [3] above, wherein the viral infection is caused by an RNA virus.

[5] The antiviral agent according to any one of [1] to [4] above, wherein the viral infection is caused by a hepatitis C virus or an influenza virus.

[6] A preventive or therapeutic agent for RNA virus infection, comprising a compound having the following general formula (I):

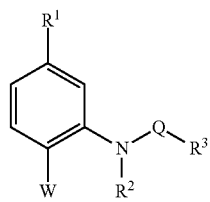

(I)

wherein

R$^1$ represents a halogen atom or a C$_{1-6}$ alkyl group that may be substituted with halogen atom;

R$^2$ represents a hydrogen atom or a C$_{1-6}$ alkyl group;

R$^3$ represents a phenyl or monocyclic heterocyclic group that may be substituted with C$_{1-6}$ alkyl, C$_{1-6}$ alkoxy or halogen atom;

Q represents —C(O)—, —C(S)—, —SO$_2$—, —C(O)NHC(O)—, —C(S)NHC(O)—, or —C(O)NHC(S)—; and W represents a halogen atom or a monocyclic or bicyclic nitrogen-containing heterocyclic group that may be substituted with halogen atom, or a pharmaceutically acceptable salt thereof.

[7] The preventive or therapeutic agent for RNA virus infection according to [6] above, wherein in the formula (I), R$^1$ represents fluorine or a trifluoromethyl group;

R$^2$ represents a hydrogen atom;

R$^3$ represents a phenyl group that may be substituted with methyl, methoxy, or fluorine, or a monocyclic heterocyclic group that may be substituted with methyl;

Q represents —C(O)—, —C(S)—, —C(O)NHC(O)—, or —C(S)NHC(O)—; and

W represents a fluorine atom or a saturated monocyclic or bicyclic heterocyclic group containing one nitrogen atom and 5 to 9 carbon atoms as ring atoms.

[8] The preventive or therapeutic agent for RNA virus infection according to [6] above, wherein the compound of the formula (I) above is a compound selected from the group consisting of:

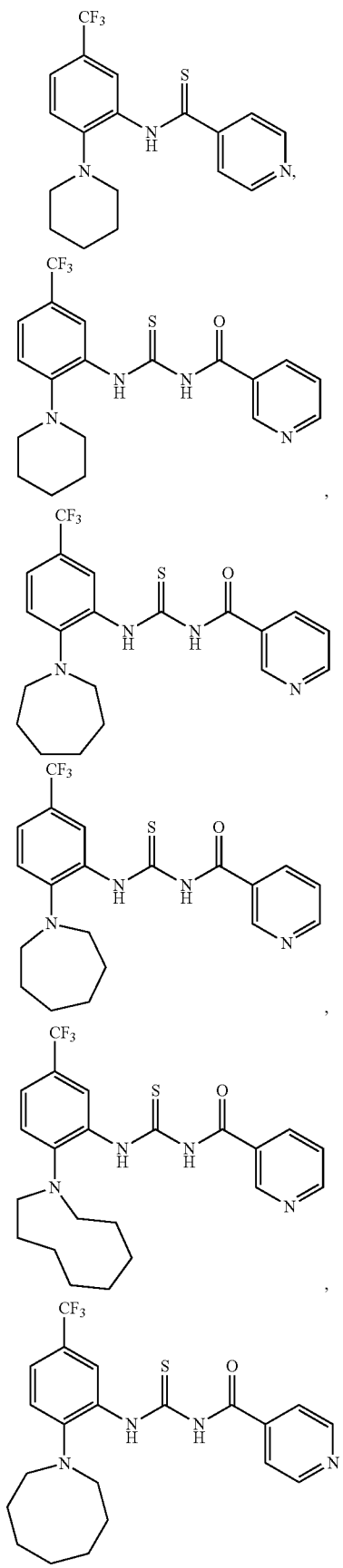

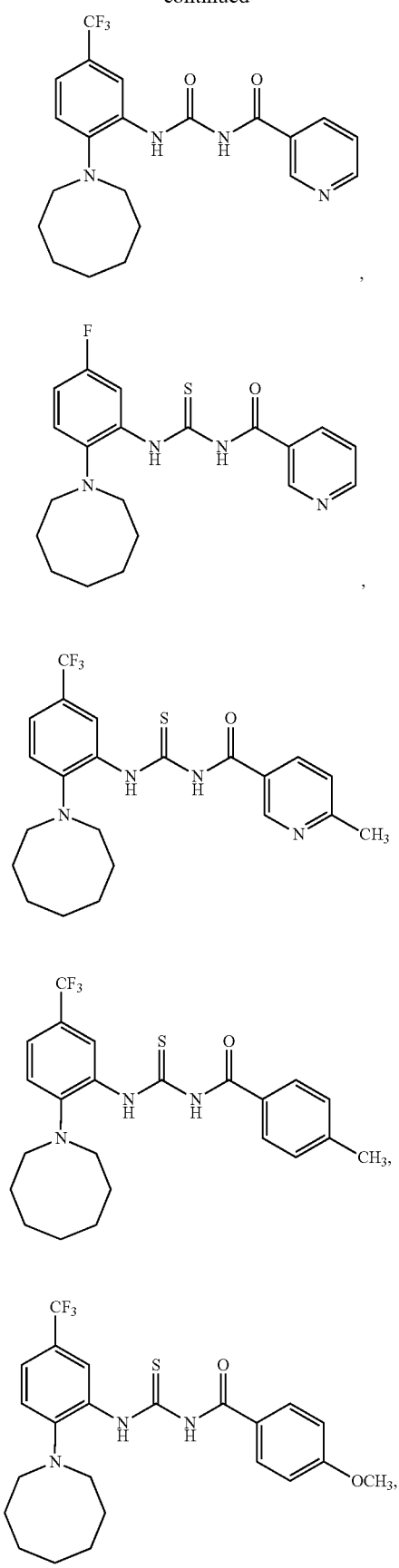
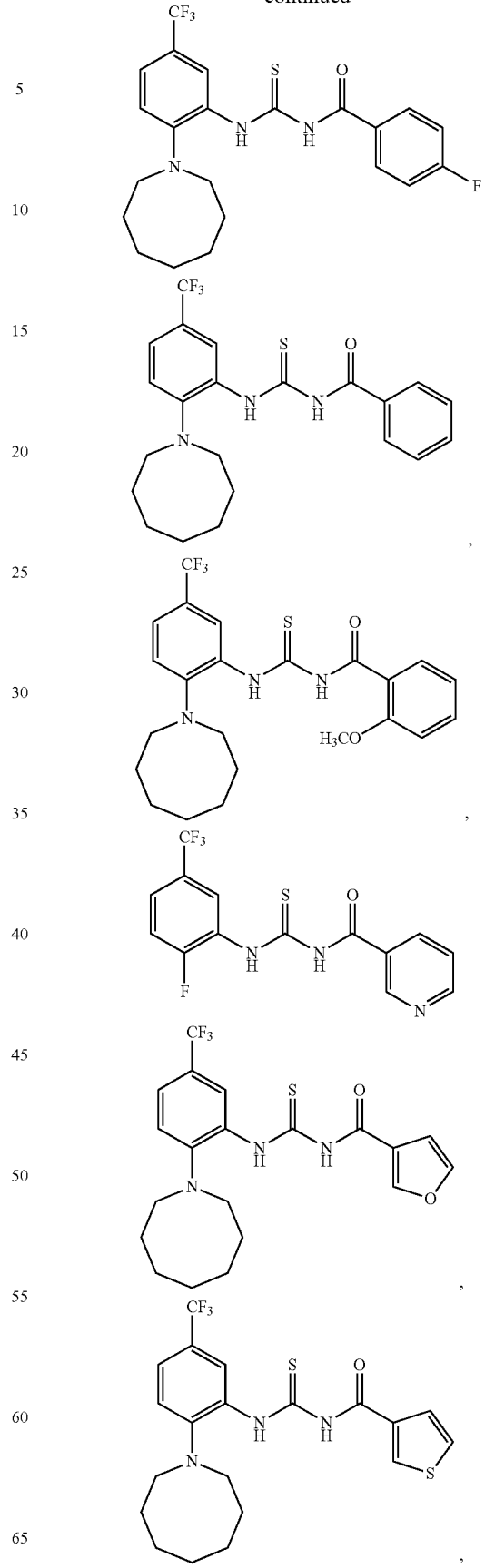

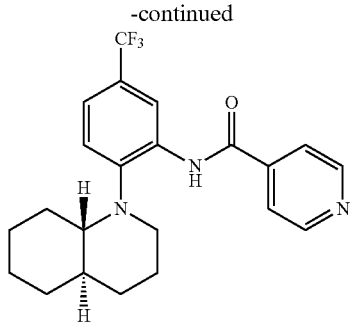

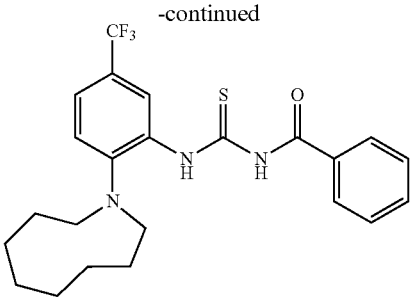

or a pharmaceutically acceptable salt thereof.

[9] The preventive or therapeutic agent for RNA virus infection according to [6] above, wherein in the formula (I), R¹ represents a trifluoromethyl group;

R² represents a hydrogen atom;

R³ represents a phenyl group or a monocyclic heterocyclic group;

Q represents —C(O)—, —C(S)—, or —C(S)NHC(O)—; and

W represents a saturated monocyclic or bicyclic heterocyclic group containing one nitrogen atom and 5 to 9 carbon atoms as ring atoms.

[10] The preventive or therapeutic agent for RNA virus infection according to [6] above, wherein the compound of the formula (I) is a compound selected from the group consisting of:

and

-continued
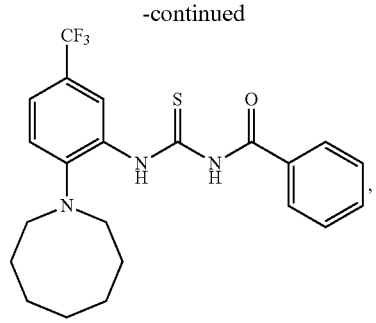
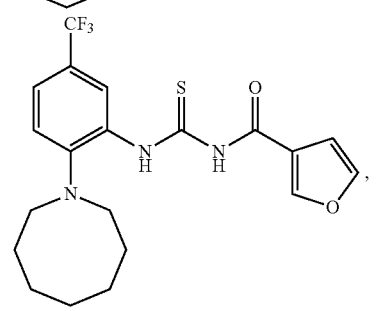
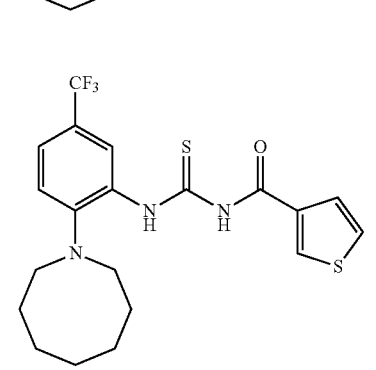
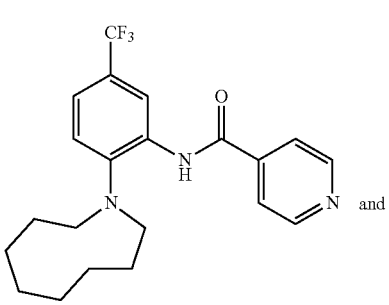
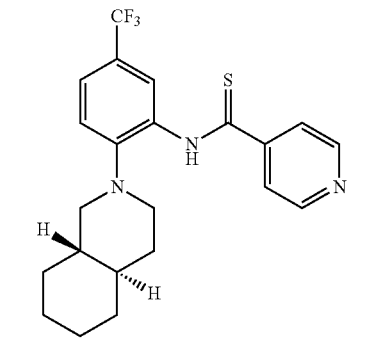
or a pharmaceutically acceptable salt thereof.
[11] A compound selected from the group consisting of:
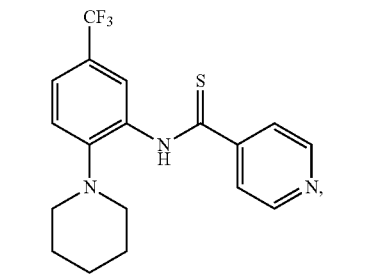
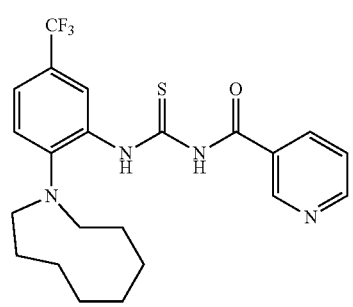
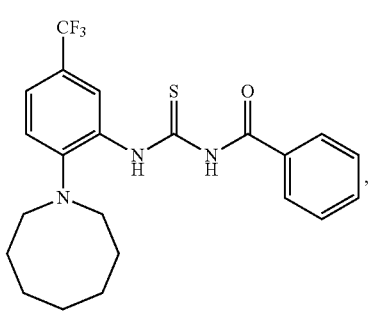
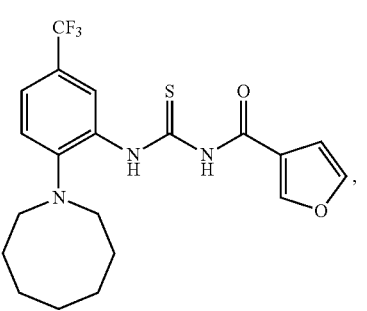

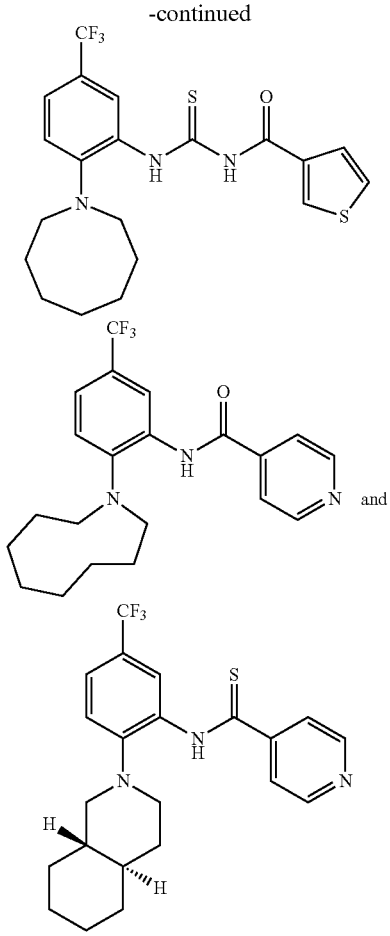

or a pharmaceutically acceptable salt thereof, or a hydrate thereof.

[12] Also, the present invention relates to use of the compound represented by the general formula (I) or a pharmaceutically acceptable salt thereof for production of a preventive or therapeutic agent for RNA virus infection.

[13] Moreover, the present invention relates to a method for treating RNA virus infection, comprising administering an effective dose of the compound represented by the general formula (I), or a pharmaceutically acceptable salt thereof to a patient with RNA virus infection.

Advantage of the Invention

As a result of synthesis of many compounds and screening, the present inventors have discovered that compounds having the structure of formula I have excellent anti-RNA virus activity. These compounds inhibit kinases existing within animal cells. Surprisingly, it has been discovered that these compounds are each effective against a plurality of different types of RNA virus.

Specifically, the present invention provides new options for treatment of RNA virus diseases. In particular, the anti-RNA viral agent according to the present invention is effective against hepatitis C viruses and influenza viruses that cause severe and socially problematic diseases.

BRIEF DESCRIPTION OF THE DRAWINGS

FIG. 1A shows the results of calculating the degrees of HCV expression and replication using LuHCV cells and luciferase activity as an index. From the thus obtained numerical values of luminescence intensity, the mean value for each test compound was calculated at each concentration, and then the luminescence intensity for each test compound was calculated on a percentage basis, with the luminescence intensity of DMSO (used as a control test substance) designated as 100%. Black triangles indicate the result when Compound 2 was used, "x" indicates the result when Compound 5 was used, and "*" indicates the result when Compound 6 was used.

FIG. 1B shows percentages for viable LuHCV cells under the conditions of FIG. 1A, which were calculated on a percentage basis, with total viable cells (upon addition of DMSO used as a control test substance) designated as 100%. Black triangles indicate the result when Compound 2 was used, "x" indicates the result when Compound 5 was used, and "*" indicates the result when Compound 6 was used.

As shown in FIG. 4, when 20 μM Compound 5 was added, proliferation occurred to almost the same extent as in the case of DMSO used as control.

BEST MODE FOR CARRYING OUT THE INVENTION

Figure 2A:
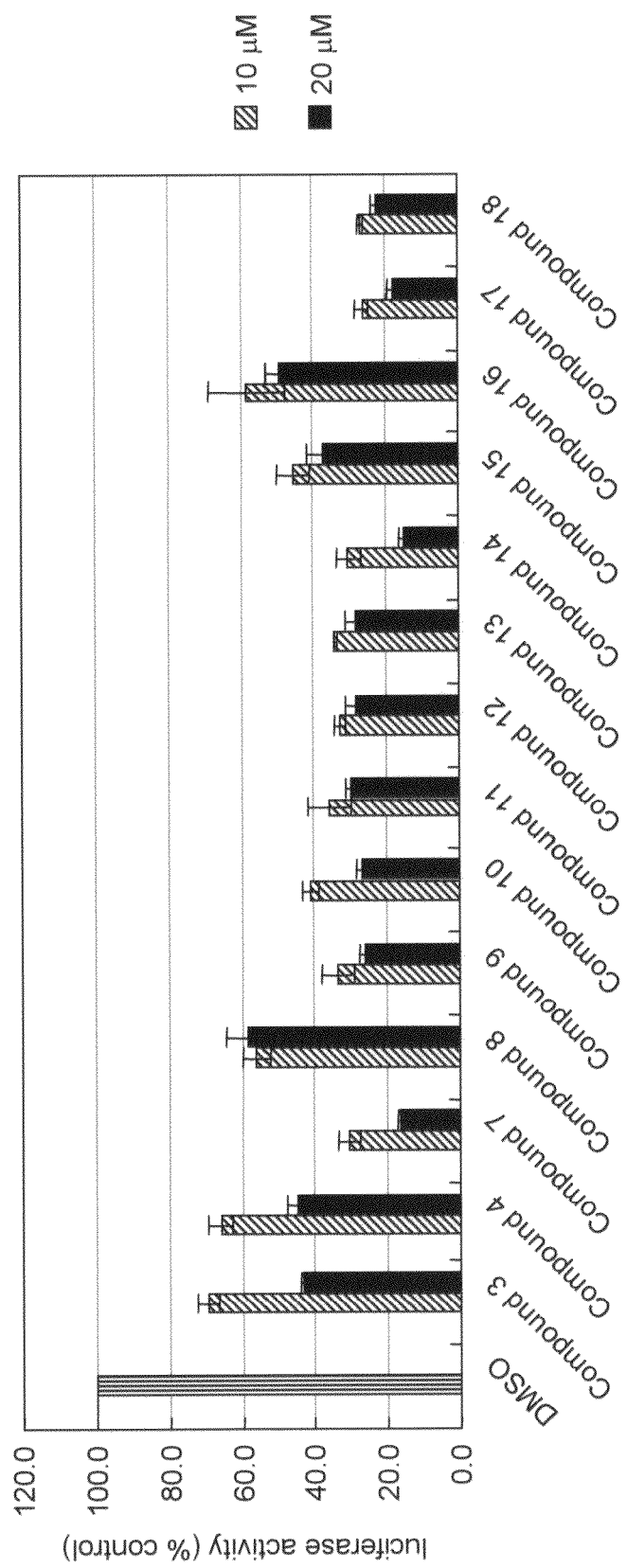
FIG. 2A shows the results of calculating the degrees of HCV expression and replication in the presence or the absence of a test compound via a method similar to that in FIG. 1A using LuHCV cells and luciferase activity as an index. With the luminescence intensity of DMSO (used as a control test substance) designated as 100%, the luminescence intensity for each test compound at each concentration on a percentage basis is shown herein.
Figure 2A:
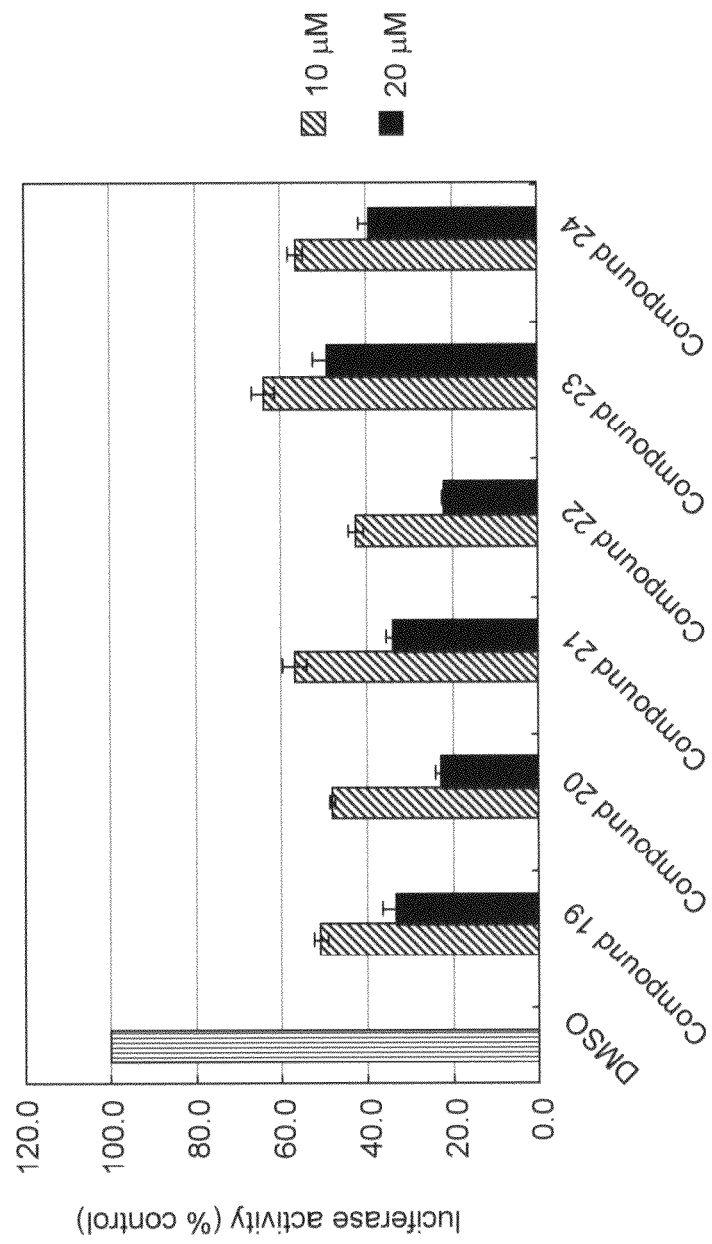

Hereinafter, the present invention is described in detail by describing the significance of terms, symbols, and the like used in the description.

The term "protein kinase of a host cell(s)" as used herein refers to a protein kinase that is intracellularly present in animal cells. In the description, "protein kinase" may also be simply referred to as "kinase." Such kinase in the present invention is particularly a kinase that controls the translation of a viral protein.

A method for evaluation of kinase activity is known in the art. Specifically, for example, such method is described in JP Patent Publication (Kokai) No. 2002-236125 A, JP Patent Publication (Kokai) No. 9-68527 A (1997), and JP Patent Publication (Kokai) No. 2005-112812 A.

The term "$C_{1-6}$ alkyl group" as used herein refers to a $C_{1-6}$ linear or branched alkyl group that is a monovalent group induced by removing any one hydrogen atom from $C_{1-6}$ aliphatic hydrocarbon. Specific examples thereof include a methyl group, an ethyl group, a 1-propyl group, a 2-propyl group, a 2-methyl-1-propyl group, a 2-methyl-2-propyl group, a 1-butyl group, a 2-butyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, and a 2,3-dimethyl-2-butyl group.

The term "$C_{1-6}$ alkoxy group" as used herein refers to an oxy group to which the above-defined "$C_{1-6}$ alkyl group" binds. Specific examples thereof include a methoxy group, an ethoxy group, a 1-propyloxy group, a 2-propyloxy group, a 2-methyl-1-propyloxy group, a 2-methyl-2-propyloxy group, a 1-butyloxy group, a 2-butyloxy group, a 1-pentyloxy group, a 2-pentyloxy group, a 3-pentyloxy group, a 2-methyl-1-butyloxy group, a 3-methyl-1-butyloxy group, a 2-methyl-2-butyloxy group, a 3-methyl-2-butyloxy group, a 2,2-dimethyl-1-propyloxy group, a 1-hexyloxy group, a 2-hexyloxy group, a 3-hexyloxy group, a 2-methyl-1-pentyloxy group, a 3-methyl-1-pentyloxy group, a 4-methyl-1-pentyloxy group, a 2-methyl-2-pentyloxy group, a 3-methyl-2-pentyloxy group, a 4-methyl-2-pentyloxy group, a 2-methyl-3-pentyloxy group, a 3-methyl-3-pentyloxy group, a 2,3-dimethyl-1-butyloxy group, a 3,3-dimethyl-1-butyloxy group, a 2,2-dimethyl-1-butyloxy group, a 2-ethyl-1-butyloxy group, a 3,3-dimethyl-2-butyloxy group, and a 2,3-dimethyl-2-butyloxy group.

The term "halogen atom" as used herein refers to a fluorine atom, a chlorine atom, a bromine atom, or an iodine atom.

The term "halogenated $C_{1-6}$ alkyl group" as used herein refers to a group wherein at least any one hydrogen atom in the above-defined "$C_{1-6}$ alkyl group" is substituted with the above-defined "halogen atom." Examples thereof include a trifluoromethyl group, a difluoromethyl group, and a monofluoromethyl group.

The term "monocyclic heterocyclic group" and the term "monocyclic or bicyclic heterocyclic group" as used herein refer to a group having a cyclic structure that contains a carbon atom and a heteroatom as ring atoms. A heteroatom is generally oxygen, nitrogen, or sulfur.

The term "salt" as used herein is not particularly limited, as long as it forms a salt with a compound according to the present invention and is pharmaceutically acceptable. Examples thereof include an inorganic acid salt, an organic acid salt, an inorganic basic salt, an organic basic salt, and an acid or basic amino-acid salt.

Preferred examples of an inorganic acid salt include hydrochloride, hydrobromate, sulfate, nitrate, and phosphate. Preferred examples of an organic acid salt include acetate, succinate, fumarate, maleate, tartrate, citrate, lactate, stearate, benzoate, methanesulfonate, and p-toluene sulfonate.

Preferred examples of an inorganic basic salt include alkali metal salts such as a sodium salt and a potassium salt, alkali earth metal salts such as a calcium salt and a magnesium salt, an aluminum salt, and an ammonium salt. Preferred examples of an organic basic salt include a diethylamine salt, a diethanolamine salt, a meglumine salt, and a N,N'-dibenzylethylenediamine salt.

Preferred examples of an acid amino-acid salt include aspartate and glutamate. Preferred examples of a basic amino-acid salt include an arginine salt, a lysine salt, and an ornithine salt.

Also, the compounds of the present invention may absorb water, so that adsorbed water becomes attached thereto, or form hydrates when left to stand in air. Such hydrates may also be encompassed as salts of the present invention.

Furthermore, the compounds of the present invention may absorb other kinds of solvent to become solvates. Such a salt is also encompassed in the present invention.

Also, in the description, the term "or" is used non-exclusively. For example, "A, B, or C" merely means that element A, B, or C is at least contained. Specifically, examples thereof include: a case in which 2 or more, or 3, or more of A, B, and C are contained; as well as a case in which an element other than any of these elements is also contained.

Also, compounds listed in the following Table may be represented by Compound Numbers in the description. Each of these compounds may also be denoted as "Compound-," quoting the relevant Compound Number.

The term "antiviral agent" as used herein refers to a drug effective for prevention or treatment of viral infections. The term "anti-RNA viral agent" as used herein refers to a drug effective for prevention and treatment of an infectious disease caused by an RNA virus.

The term "antiviral activity" as used herein is understood to refer to any effects useful as mechanisms for prevention or treatment of viral infections, such as an effect of suppressing viral replication, an effect of decreasing viral infections, and an effect of decreasing or eliminating infecting viruses. The term "anti-RNA viral activity" as used herein is understood to refer to any effects useful as mechanisms for prevention or treatment of RNA virus infections, such as an effect of suppressing RNA virus replication, an effect of decreasing RNA virus infections, and an effect of decreasing or eliminating infection by RNA viruses.

As active ingredients of the preventive or therapeutic agent for an RNA virus infection of the present invention, a compound represented by the following general formula (I) and a pharmaceutically acceptable salt thereof can be used.

General Formula (I):

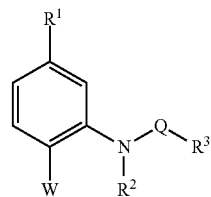

wherein, $R^1$ represents a halogen atom or a $C_{1-6}$ alkyl group that may be substituted with halogen atom;

$R^2$ represents a hydrogen atom or a $C_{1-6}$ alkyl group;

$R^3$ represents a phenyl or monocyclic heterocyclic group that may be substituted with $C_{1-6}$ alkyl, $C_{1-6}$ alkoxy or halogen atom;

Q represents —C(O)—, —C(S)—, —SO$_2$—, —C(O)NHC(O)—, —C(S)NHC(O)—, or —C(O)NHC(S)—; and W represents a halogen atom or a monocyclic or bicyclic nitrogen-containing heterocyclic group that may be substituted with halogen atom.

Further preferably, in the above formula (I), $R^1$ represents fluorine or a trifluoromethyl group;

$R^2$ represents a hydrogen atom;

$R^3$ represents a phenyl group that may be substituted with methyl, methoxy, or fluorine, or a monocyclic heterocyclic group that may be substituted with methyl;

Q represents —C(O)—, —C(S)—, —C(O)NHC(O)—, or —C(S)NHC(O)—; and

W represents a fluorine atom or a saturated monocyclic or bicyclic heterocyclic group containing one nitrogen atom and 5 to 9 carbon atoms as ring atoms.

Further preferably, in the above formula (I), $R^1$ represents a trifluoromethyl group;

$R^2$ represents a hydrogen atom;

$R^3$ represents a phenyl group or a monocyclic heterocyclic group;

Q represents —C(O)—, —C(S)—, or —C(S)NHC(O)—; and

W represents a saturated monocyclic or bicyclic heterocyclic group containing one nitrogen atom and 5 to 9 carbon atoms as ring atoms.

Further more preferably, the compounds of formula (I) are selected from the group consisting of:

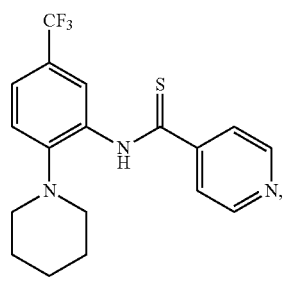

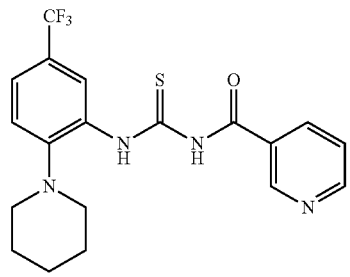

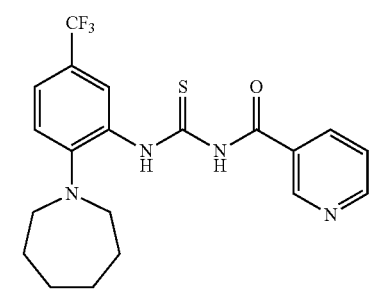

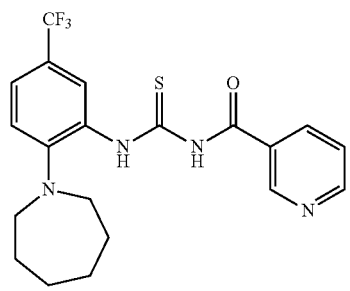

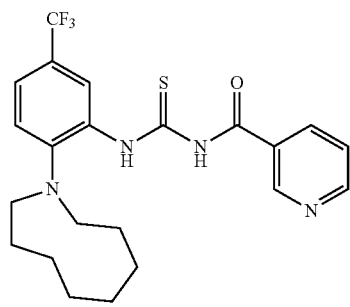

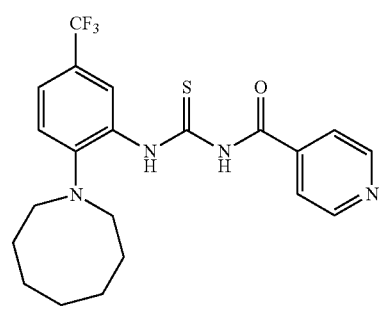

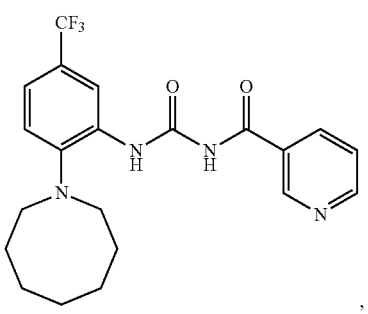
,
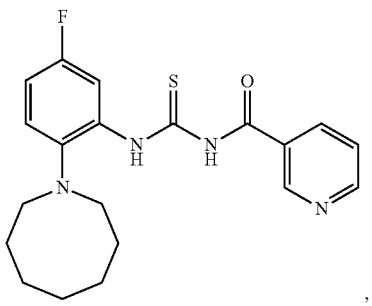
,
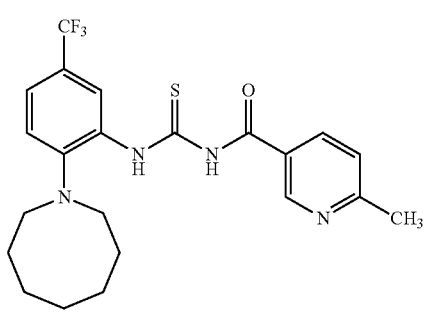
,
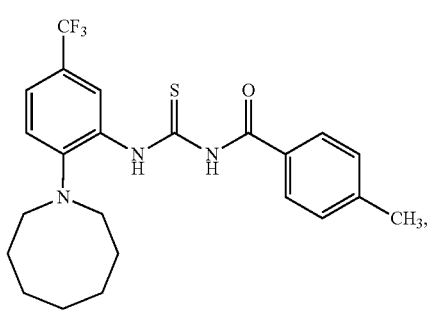
,
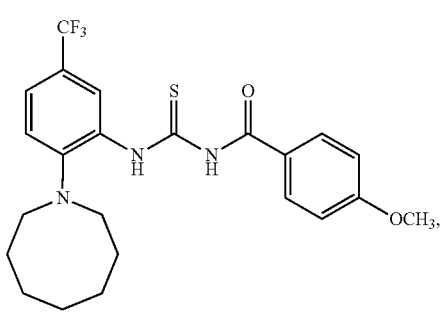
,
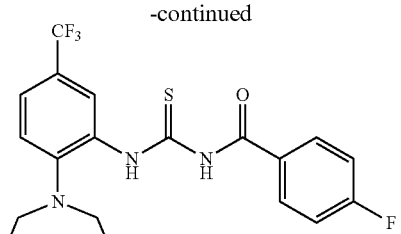
,
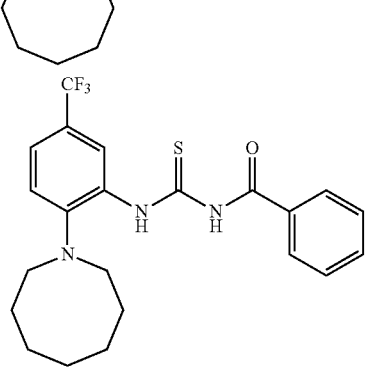
,
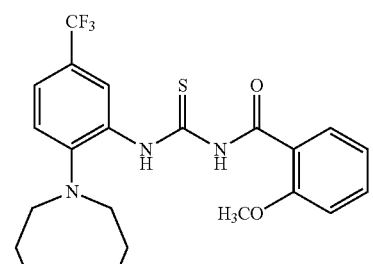
,
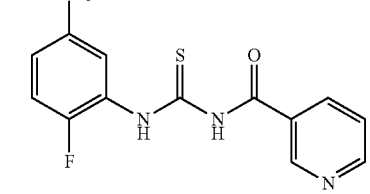
,
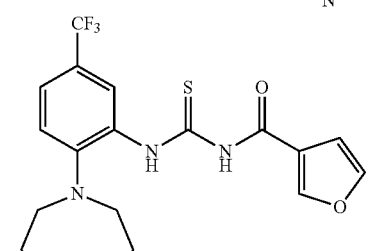
,
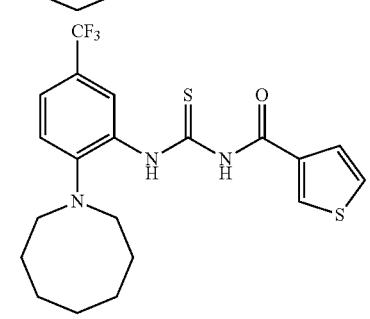
,

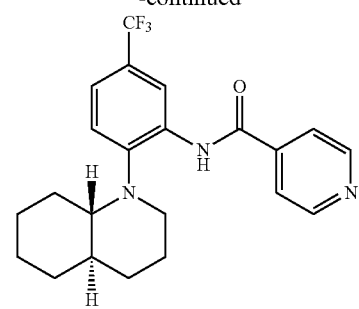
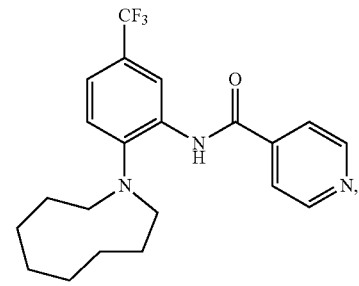
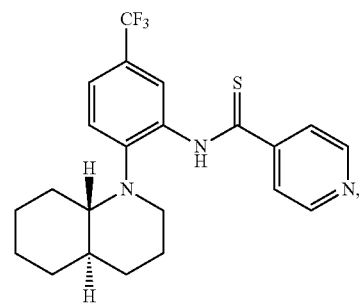
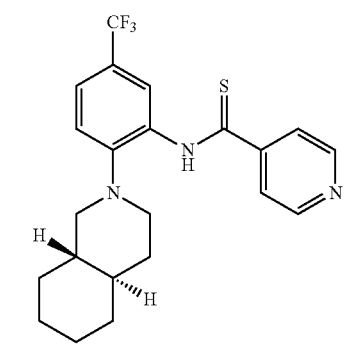
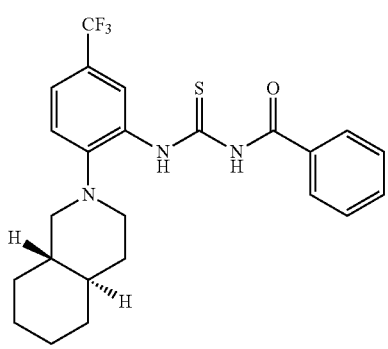
and
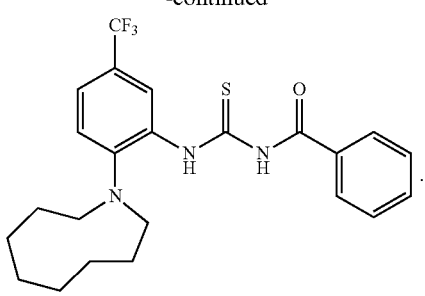
Most preferably, the compound of formula (I) is selected from the group consisting of:
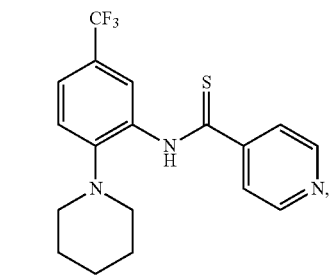
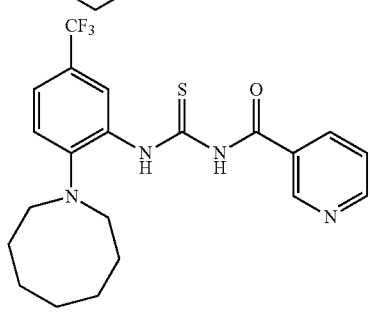
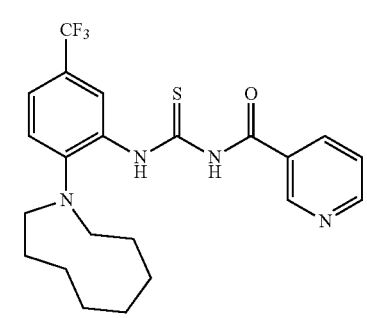
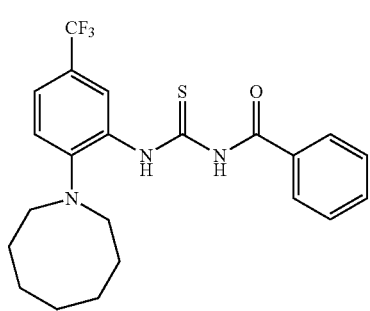
, 21
-continued
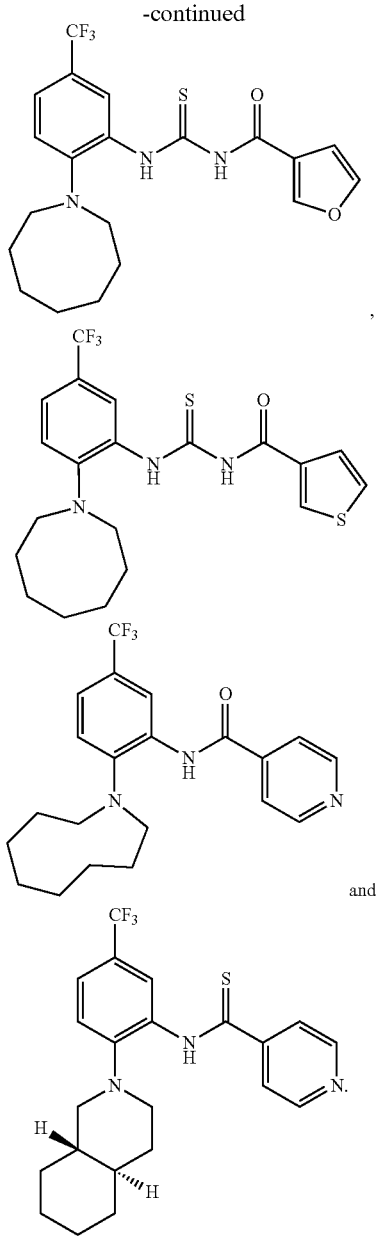
Examples of the specific compound represented by the general formula (I) are as listed below, but the present invention is not limited to the compounds listed below.
| Compound number | Compound structure |
|---|---|
| Compound 2 | 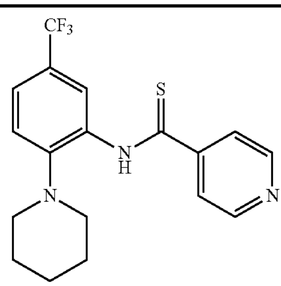 |
22
-continued
| Compound number | Compound structure |
|---|---|
| Compound 3 | 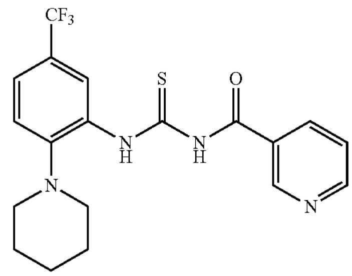 [SMILES: O=C(NC(=S)Nc1cc(C(F)(F)F)ccc1N1CCCCC1)c1cccnc1] |
| Compound 4 | 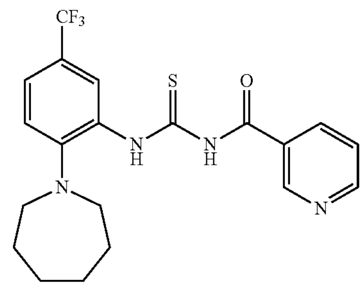 [SMILES: O=C(NC(=S)Nc1cc(C(F)(F)F)ccc1N1CCCCCC1)c1cccnc1] |
| Compound 5 | 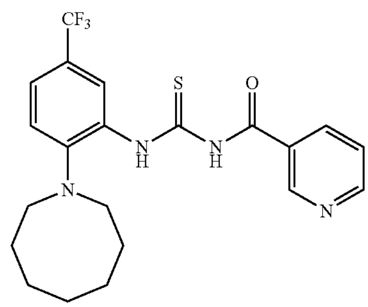 [SMILES: O=C(NC(=S)Nc1cc(C(F)(F)F)ccc1N1CCCCCCC1)c1cccnc1] |
| Compound 6 | 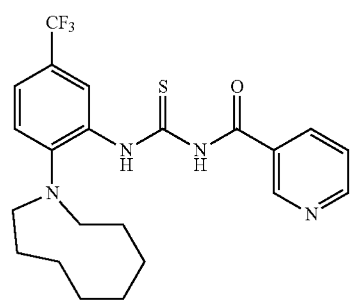 [SMILES: O=C(NC(=S)Nc1cc(C(F)(F)F)ccc1N1CCCCCCCC1)c1cccnc1] |
| Compound 7 | 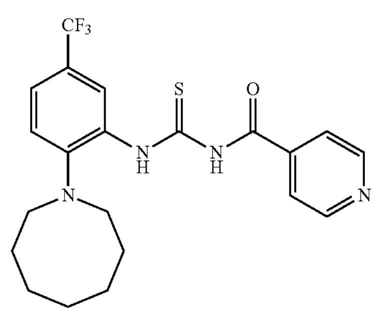 [SMILES: O=C(NC(=S)Nc1cc(C(F)(F)F)ccc1N1CCCCCCC1)c1ccncc1] |

| Compound number | Compound structure |
|---|---|
| Compound 8 | 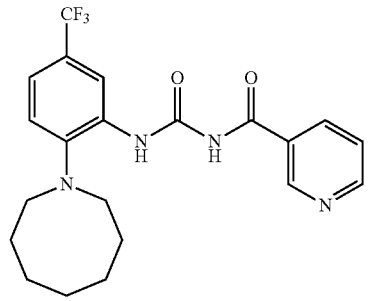 [SMILES: O=C(NC(=O)c1cccnc1)Nc1cc(C(F)(F)F)ccc1N1CCCCCCC1] |
| Compound 9 | 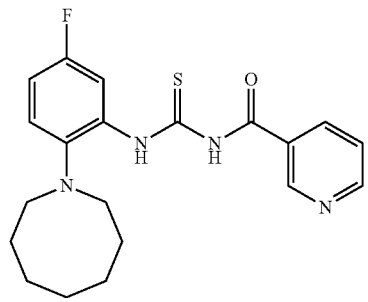 [SMILES: O=C(NC(=S)Nc1cc(F)ccc1N1CCCCCCC1)c1cccnc1] |
| Compound 10 | 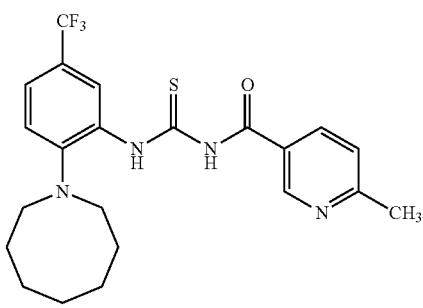 [SMILES: Cc1ccc(C(=O)NC(=S)Nc2cc(C(F)(F)F)ccc2N2CCCCCCC2)cn1] |
| Compound 11 | 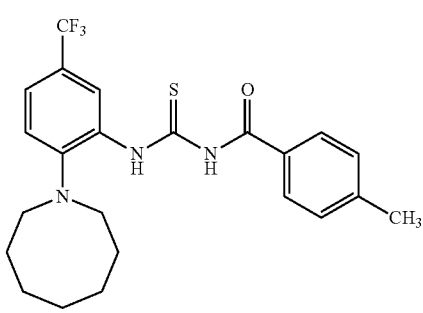 [SMILES: Cc1ccc(C(=O)NC(=S)Nc2cc(C(F)(F)F)ccc2N2CCCCCCC2)cc1] |
| Compound 12 | 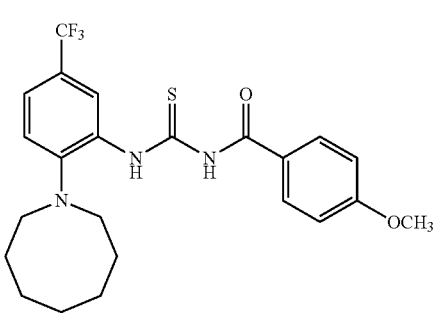 [SMILES: COc1ccc(C(=O)NC(=S)Nc2cc(C(F)(F)F)ccc2N2CCCCCCC2)cc1] |
| Compound number | Compound structure |
|---|---|
| Compound 13 | 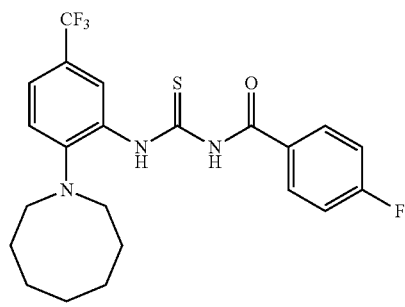 [SMILES: O=C(NC(=S)Nc1cc(C(F)(F)F)ccc1N1CCCCCCC1)c1ccc(F)cc1] |
| Compound 14 | 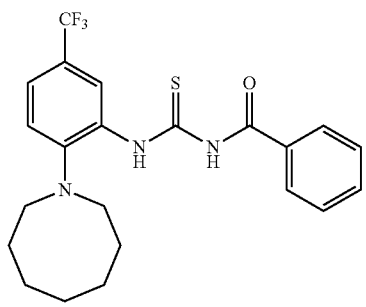 [SMILES: O=C(NC(=S)Nc1cc(C(F)(F)F)ccc1N1CCCCCCC1)c1ccccc1] |
| Compound 15 | 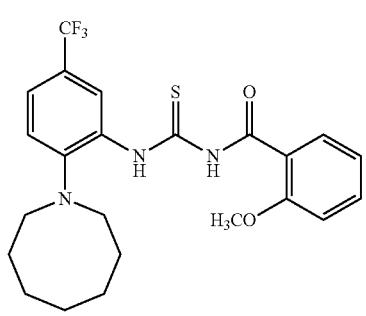 [SMILES: COc1ccccc1C(=O)NC(=S)Nc1cc(C(F)(F)F)ccc1N1CCCCCCC1] |
| Compound 16 | 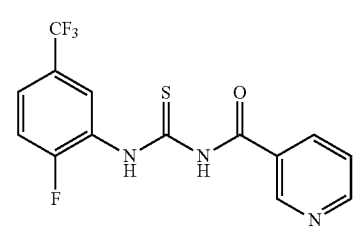 [SMILES: O=C(NC(=S)Nc1cc(C(F)(F)F)ccc1F)c1cccnc1] |
| Compound 17 | 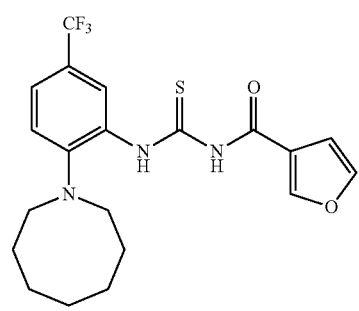 [SMILES: O=C(NC(=S)Nc1cc(C(F)(F)F)ccc1N1CCCCCCC1)c1ccoc1] |

| Compound number | Compound structure |
|---|---|
| Compound 18 | 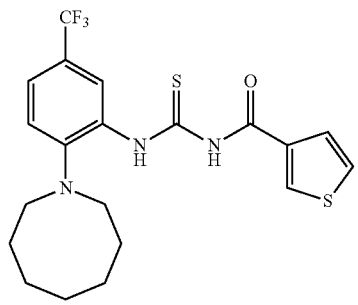 [SMILES: O=C(NC(=S)Nc1cc(C(F)(F)F)ccc1N1CCCCCCC1)c1ccsc1] |
| Compound 19 | 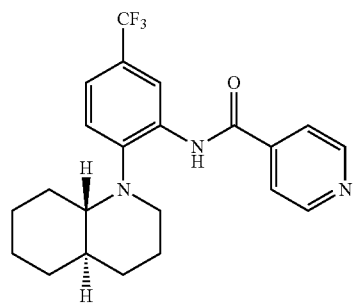 [SMILES: O=C(Nc1cc(C(F)(F)F)ccc1N1CCC[C@H]2CCCC[C@@H]21)c1ccncc1] |
| Compound 20 | 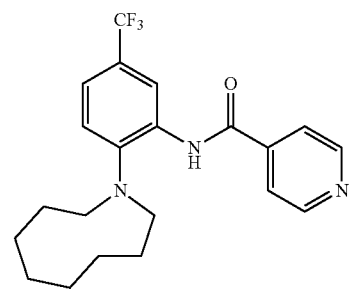 [SMILES: O=C(Nc1cc(C(F)(F)F)ccc1N1CCCCCCCC1)c1ccncc1] |
| Compound 21 | 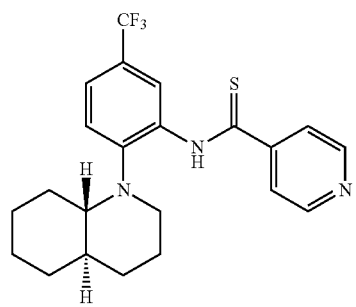 [SMILES: FC(F)(F)c1ccc(N2CCC[C@H]3CCCC[C@@H]32)c(NC(=S)c2ccncc2)c1] |
| Compound 22 | 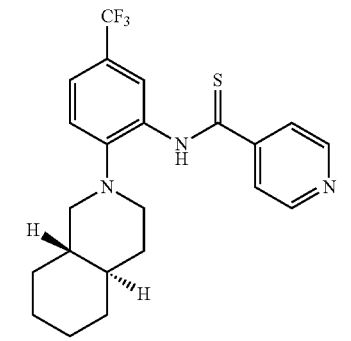 [SMILES: FC(F)(F)c1ccc(N2CC[C@H]3CCCC[C@@H]3C2)c(NC(=S)c2ccncc2)c1] |

| Compound number | Compound structure |
|---|---|
| Compound 23 | 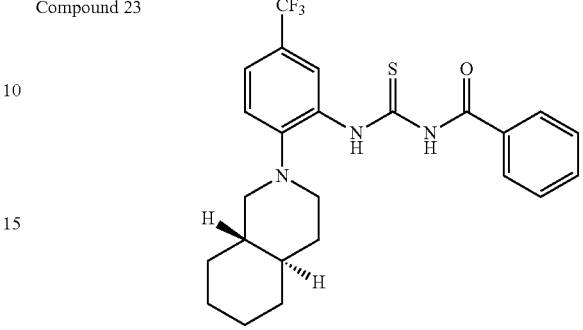 |
| Compound 24 | 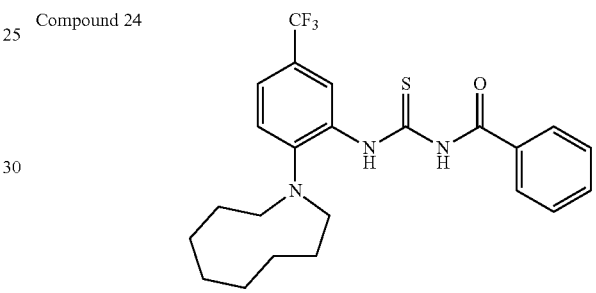 |

Specifically, the present invention relates to an antiviral agent comprising any compound exemplified above, and particularly at least one of the above-exemplified compounds denoted with the following compound numbers: Compound 2, Compound 3, Compound 4, Compound 5, Compound 6, Compound 7, Compound 8, Compound 9, Compound 10, Compound 11, Compound 12, Compound 13, Compound 14, Compound 15, Compound 16, Compound 17, Compound 18, Compound 19, Compound 20, Compound 21, Compound 22, Compound 23, and Compound 24. The present invention further preferably relates to an antiviral agent comprising at least one of the above-exemplified compounds with the following compound numbers: Compound 2, Compound 5, Compound 6, Compound 14, Compound 17, Compound 18, Compound 20, and Compound 22, which are represented by the following structural formulae:

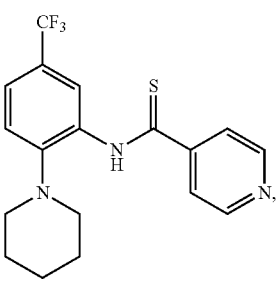

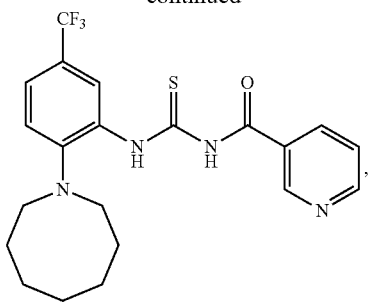

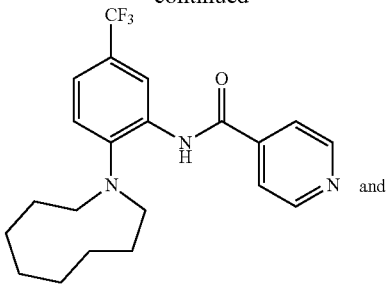 and

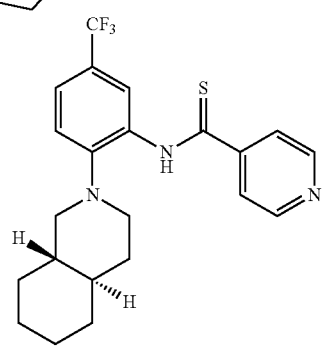

These compounds (aniline derivatives) or pharmaceutically acceptable salts thereof are effective as anti-RNA viral agents.

Examples of viruses against which the compounds of the present invention are used as antiviral agents include, but are not limited to, RNA viruses belonging to the families Flaviviridae and Orthomyxoviridae. Examples of other viruses include, but are not limited to, RNA viruses belonging to the families Retroviridae, Paramyxoviridae, Arenaviridae, Filoviridae, Rhabdoviridae, Bunyaviridae, Coronaviridae, Togaviridae, Reoviridae, Caliciviridae, and Picornaviridae. Preferred examples thereof are human pathogenic RNA viruses. The most preferable examples thereof are hepatitis C virus and influenza viruses.

A representative method for producing the compound represented by the above formula (I) according to the present invention is as described below. In addition, the compound represented by the above formula (I) according to the present invention is also described in International Patent Publication (pamphlet) WO2005/063293, and the content thereof is incorporated herein by reference.

The following $R^1$, $R^2$, $R^3$, $R^4$, $R^5$, $R^6$, Q, and W are as defined in the above formula (I). The term "room temperature" refers to a temperature ranging from about 20° C. to 30° C.

Production method A

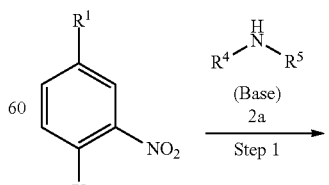

X = F, Cl, Br, OMs, OTs, OTf
W = $HNR^4R^5$

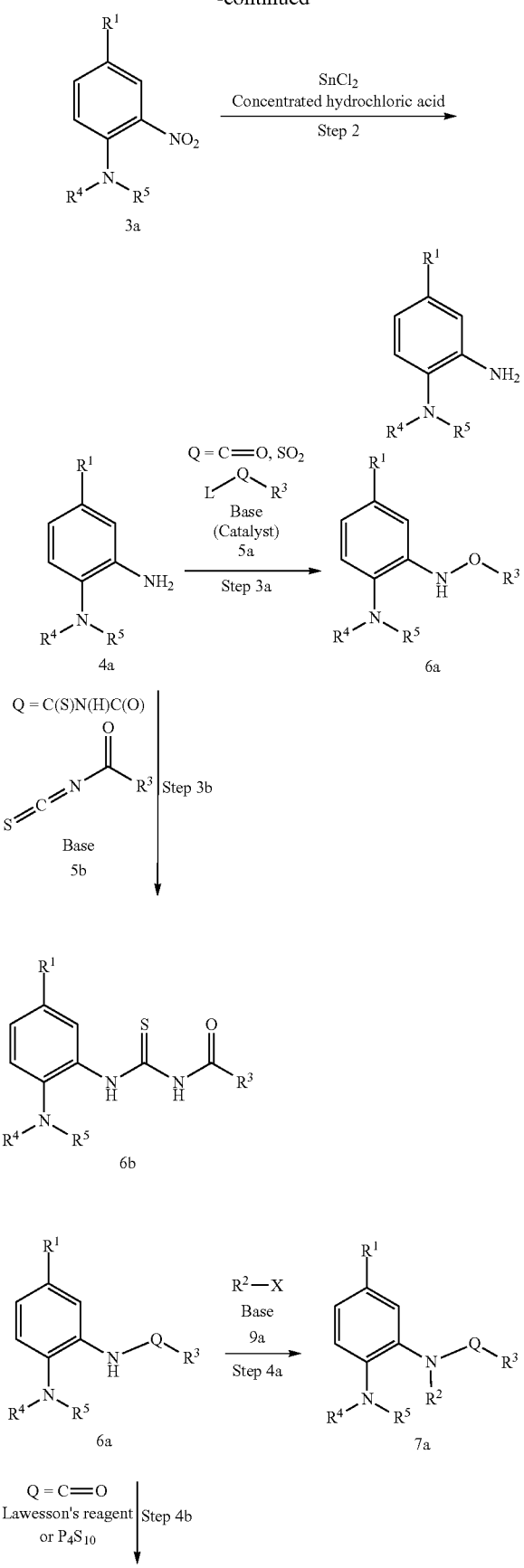

Step 1

Step 1 comprises reacting Compound 1a with Compound 2a, so as to obtain Compound 3a. A nitrobenzene derivative 1a as a raw material is obtained from commercial products or obtained by appropriately inducing functional groups. Hal is a halogen atom serving as a leaving group. Compound 2a is a reagent containing —$NR^5R^6$ to be introduced. X represents a hydrogen atom or the like. One to 2 equivalents of Compound 2a are preferably used. The reaction can be performed in a solvent in the presence of a base.

As bases, triethylamine, diisopropylethylamine, pyridine, 4-(dimethylamino)pyridine, and the like can be used. One to 5 equivalents of base are preferably used. Also, an excess amount (ranging from 1 to 5 equivalents) of X—$NR^5R^6$ can be used as an alternative base.

Examples of a solvent include dimethyl sulfoxide, N,N-dimethylformamide, N-methylpyrrolidone, dioxane, tetrahydrofuran, and toluene.

The reaction can be performed at a reaction temperature ranging from 0° C. to 150° C. and can be preferably performed at room temperature.

Step 2

Step 2 comprises reducing a nitro group of Compound 3a to an amino group, so as to obtain Compound 4a.

A reduction method can be performed, involving contact with concentrated hydrochloric acid or the like in a solvent in the presence of tin chloride or the like. In addition to this example, a general reduction reaction such as catalytic hydrogenation can also be used.

As a reaction solvent, methanol, ethanol, N,N-dimethylformamide, tetrahydrofuran, 1,2-dimethoxyethane, 1,4-dioxane, water, or a mixed solvent of any thereof can be used.

Tin chloride or the like to be used as a reducing agent is preferably used in an amount ranging from 1 to 20 equivalents thereof based on mass ratio. The reaction can be performed at a temperature ranging from 0° C. to 100° C.

In addition, Compound 3a and Compound 4a are commercially available. In such a case, commercial products can be used. In particular, when "W" represents hydrogen or halogen in general formula (I), commercial products can be obtained in many cases.

Step 3a

Step 3a comprises reacting Compound 4a with Compound 5a, so as to obtain Compound 6a. "L" represents a halogen atom or the like.

The reaction can be performed in a solvent in the presence of a base. A catalyst may be added for reaction, if necessary. In this case, 1 to 3 equivalents of Compound 5a are preferably used.

As a reaction solvent, dichloromethane, chloroform, 1,4-dioxane, tetrahydrofuran, toluene, pyridine, N,N-dimethylformamide, N-methylpyrrolidone, or the like can be used.

As a base, triethylamine, diisopropylethylamine, pyridine, 4-(dimethylamino)pyridine, or the like can be used.

Other examples of the reaction that can be used herein are: a general amide bond formation reaction using a condensing agent when "L" is a hydroxyl group and a general amide bond formation reaction when "L" is a succinimidyl group, an imidazolyl group, or the like as a leaving group.

An example of a catalyst is 4-(dimethylamino)pyridine.

The reaction can be performed at a temperature ranging from 0° C. to 100° C.

Step 3b

Step 3b comprises reacting Compound 4a with Compound 5b, so as to obtain Compound 6b.

The reaction can be performed by causing acyl isothiocyanate to act in a solvent in the presence of a base. As acyl isothiocyanate, a commercial product or acyl isothiocyanate appropriately prepared from acyl halide and thiocyanate in a reaction solution can be used intact. One to 5 equivalents of acyl isothiocyanate are preferably used. As thiocyanate, potassium thiocyanate, sodium thiocyanate, ammonium thiocyanate, or the like can be used and 1 to 5 equivalents thereof are preferably used.

Examples of a solvent include acetonitrile, N,N-dimethylformamide, N-methylpyrrolidone, tetrahydrofuran, ethylene glycoldimethyl ether, and 1,4-dioxane.

As a base, triethylamine, diisopropylamine, pyridine, 4-(dimethylamino)pyridine, or the like can be used, for example. One to 5 equivalents of a base are preferably used.

The reaction can be performed at a temperature ranging from 0° C. to 150° C.

Step 4a

Step 4a comprises alkylating (conversion to $R^2$) an amide group portion of Compound 6a, so as to obtain Compound 7a.

The reaction can be performed in a solvent in the presence of a base using an alkylation reagent ($R^2$—X). "X" is a halogen atom or sulfonate serving as a leaving group. One to 5 equivalents of an alkylation reagent ($R^2$—X) are preferably used.

Examples of a solvent include N,N-dimethylformamide, N-methylpyrrolidone, tetrahydrofuran, ethylene glycoldimethyl ether, 1,4-dioxane, acetonitrile, and ether.

As a base, sodium hydride, potassium hydride, lithium hydride, butyllithium, methyllithium, phenyllithium, lithium diisopropylamide, or the like can be used. One to 5 equivalents of a base are preferably used.

The reaction can be performed at a temperature ranging from 0° C. to 150° C.

Step 4b

Step 4b comprises converting a carbonyl group of an amide bond of Compound 6a to a thiocarbonyl group, so as to obtain Compound 7b.

The reaction is performed in a solvent using a thiocarbonylation reagent. As a thiocarbonylation reagent, Lawesson's reagent (2,4-bis(4-methoxyphenyl)-1,3,2,4-dithiadiphosphetane 2,4-disulfide), phosphorus pentasulfide (phosphorus sulfide, $P_4S_{10}$), or the like can be used. One to 5 equivalents of a thiocarbonylation reagent are preferably used.

Examples of a solvent include toluene, benzene, chlorobenzene, xylene, N,N-dimethylformamide, N-methylpyrrolidone, ethylene glycoldimethyl ether, 1,4-dioxane, and tetrahydrofuran.

The reaction can be performed at a temperature ranging from 0° C. to 200° C.

The above examples are typical examples for the method for producing Compound (I) according to the present invention. Raw-material compounds and various reagents to be used in production of the compounds according to the present invention may form salts, hydrates or solvates, may differ depending on starting raw materials, solvents, and the like to be used herein, and are not particularly limited, as long as they do not inhibit the reaction. It goes without saying that solvents to be used herein may differ depending on starting raw materials, reagents, and the like, and they are not particularly limited, as long as they do not inhibit the reaction but dissolve starting materials to some degree. When Compound (I) according to the present invention is obtained in a free form, it can be converted into the state of a salt or a hydrate thereof that the above Compound (I) may form according to a conventional method.

When Compound (I) according to the present invention is obtained as a salt or a hydrate thereof, it can be converted into the above free form of Compound (I) according to a conventional method.

Also, various isomers (e.g., a geometric isomer, an optical isomer based on asymmetric carbon, a rotational isomer, a stereoisomer, and a tautomer) obtained from Compound (I) according to the present invention can be purified and isolated using general separation means, such as recrystallization, a diastereomeric salt method, enzymatic cleavage, or various chromatographies (e.g., thin-layer chromatography, column chromatography, or gas chromatography).

The compounds of the present invention can be prepared as compositions with pharmaceutically acceptable carriers. For example, pharmaceutical compositions can be prepared through application of known preparation techniques. When the pharmaceutical compositions of the present invention are used as antiviral agents (specifically, preventive or therapeutic agents for viral infections) or other medicines, examples of routes for administration thereof include oral administration of tablets, capsules, granules, powders, pills, troches, syrups, or the like and parenteral administration of injection preparations, aerosol agents, suppositories, patches, adhesive skin patches, lotions, liniments, ointments, eye drops, or the like. These preparations are produced by known methods using additives such as excipients, lubricants, binders, disintegrants, stabilizers, taste and flavor corrigents, diluents, or the like.

Examples of excipients include starch such as potato starch, and corn starch, lactose, crystalline cellulose, and calcium hydrogen phosphate.

Examples of coating agents include ethyl cellulose, hydroxypropylcellulose, hydroxypropylmethylcellulose, shellac, talc, carnauba wax, and paraffin.

Examples of binders include polyvinylpyrrolidone, Macrogol, and compounds similar to the above examples of excipients.

Examples of disintegrants include compounds similar to the above examples of excipients and chemically-modified starches and/or celluloses such as croscarmellose sodium, sodium carboxymethyl starch, cross-linked polyvinylpyrrolidone.

Examples of stabilizers include: parahydroxybenzoate esters such as methylparaben and propylparaben; alcohols such as chlorobutanol, benzyl alcohol, and phenyl ethyl alcohol; benzalkonium chloride; phenols such as phenol and cresol; thimerosal; dehydroacetic acid; and sorbic acid.

Examples of taste and flavor corrigents include generally used sweeteners, acidulants, and aroma chemicals.

Also, as a solvent for production of solutions, ethanol, phenol, chlorocresol, purified water, distilled water, or the like can be used.

Examples of surfactants or emulsifiers include polysorbate 80, polyoxyl stearate 40, and Lauromacrogol.

When the pharmaceutical composition of the present invention is used as an antiviral agent, the dose(s) of the compound(s) or a pharmaceutical acceptable salt thereof of the present invention differ depending on symptoms, age, the route of administration, and the like. For example, in the case of oral administration, a dose ranging from 0.01 mg (preferably 0.1 mg)/day as the lower limit to 2000 mg (preferably 500 mg, and more preferably 100 mg)/day as the upper limit is desirably administered to a patient (a warm-blooded animal, and in particular a human) in a single dose or in divided doses, depending on the symptoms. In the case of intravenous administration, a dose ranging from 0.001 mg (preferably 0.01 mg)/day as the lower limit to 500 mg (preferably 50 mg)/day as the upper limit is desirably administered to an adult in a single dose or in divided doses depending on the symptoms.

[Target Viruses]

Examples of viruses against which the compounds of the present invention are used as antiviral agents include, but are not limited to, RNA viruses belonging to the families Flaviviridae and RNA viruses belonging to the family Orthomyxoviridae, as described above. Examples of other target viruses include RNA viruses belonging to the families Retroviridae, Paramyxoviridae, Arenaviridae, Filoviridae, Rhabdoviridae, Bunyaviridae, Coronaviridae, Togaviridae, Reoviridae, Caliciviridae, and Picornaviridae. Preferred examples thereof include human pathogenic RNA viruses. The most preferable viruses are hepatitis C viruses and influenza viruses.

[Viral Infections]

Examples of viral infections against which the compounds of the present invention can be used for prevention and treatment thereof include, but are not limited to, flavivirus infections such as hepatitis C and Japanese encephalitis, orthormyxovirus infections such as influenza, retrovirus infections such as AIDS, paramyxovirus infections such as measles and mumps, togavirus infections such as rubella, and rotavirus infections.

[Therapeutic Methods]

The present invention encompasses a method for preventing or treating a viral infection through administration of a preventive or therapeutic agent for the viral infection according to the present invention. Such preventive or therapeutic agent for a viral infection according to the present invention can be intermittently or continuously administered via oral, transdermal, submucosal, subcutaneous, intramuscular, intravascular, intracerebral, or intraperitoneal administration, so that the in vivo concentration is within the range between 100 nM and 1 mM, for example.

EXAMPLES

The present invention is described in more detail using Examples, but they are given only for illustrative purposes. The present invention is not limited to the Examples. In addition, all publications cited herein are incorporated herein as part of the description.

Column chromatography was carried out using silica gel (MERCK 9385-5B, 70-230 mesh) as described below. Thin-layer chromatography (TLC) was carried out using a glass plate (MERCK 5715, silica gel 60 $F_{254}$) that had been coated with silica gel in advance. The melting point was measured using a micro melting point apparatus YANACO MP-500D or MP-J3 (Yanaco Group). The $^1$H NMR spectrum and $^{13}$C NMR spectrum were measured using a JNM AL-400 nuclear magnetic resonance apparatus (JEOL Ltd.) or MERCURY 300 (Varian). As a solvent for NMR spectrum measurement, $CDCl_3$ or $CD_3OD$ (ISOTEC or CIL) was used. A chemical shift was expressed as a relative value using tetramethylsilane $((CH_3)_4Si)$ as the internal standard (0 ppm), and a coupling constant (J) was denoted with Hz. Abbreviations s, d, t, m, and br represent singlet, doublet, triplet, quartet, multiplet, and broad peak, respectively. Infrared-spectroscopy spectrum (IR) measurement was carried out using an FTIR-8100A or IR Prestige-21 (Shimadzu Corporation). Mass spectroscopy (MS) was carried out using a GCMS-QP5050 (Shimadzu Corporation). The MS molecular ion peak was denoted with integers. Elementary analysis was carried out using an MT-6 (Yanaco Analytical Instruments Inc).

Reference Example 1

Synthesis of Compound 1

A typical method for synthesis of Compound 1 is as follows.

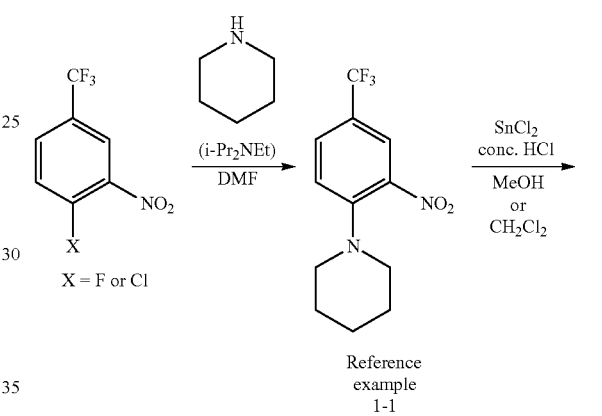

Reference example 1-1

Reference example 1-2

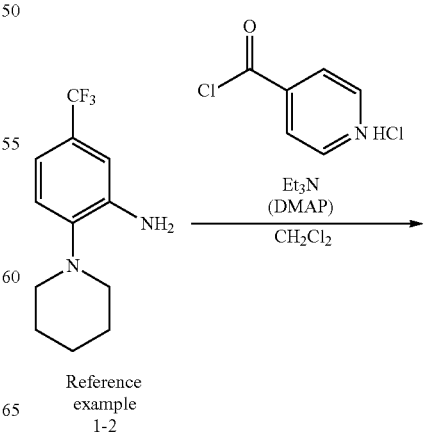

Reference example 1-2

-continued

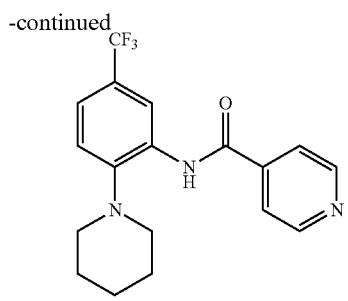

Reference example 1-3
Compound 1

Reference Example 1-1A

Piperidine (220 μL, 2.22 mmol) and N,N-diisopropylethylamine (220 μL, 2.40 mmol) were added sequentially at room temperature to 1 mL of a N,N-dimethylformamide (DMF) solution of 1-fluoro-2-nitro-4-(trifluoromethyl)benzene (427 mg, 2.04 mmol; commercial product). The mixture was stirred for 1 hour. Water was added to the mixture and then the mixture was subjected to extraction with ether (×3). The thus extracted organic layer was washed with brine, dried on $Na_2SO_4$, filtered, and then concentrated under reduced pressure.

The residue was purified by silica gel column chromatography (40 g, hexane/ethyl acetate=10/1), so that 1-[2-nitro-4-(trifluoromethyl)phenyl]piperidine (561 mg, 2.04 mmol, quant.) was obtained as orange solid.

The results of TLC and $^1$H NMR ($CDCl_3$, 400 MHz) are as follows: TLC $R_f$ 0.47 (hexane/acetone=16/1); $^1$H NMR ($CDCl_3$, 400 MHz) δ1.61-1.68 (m, 2H, $CH_2$), 1.72 (tt, 4H, J=5.3, 5.3 Hz, $2CH_2$), 3.13 (t, 4H, J=5.3 Hz, $2CH_2$), 7.13 (d, 1H, J=8.8 Hz, aromatic), 7.61 (dd, 1H, J=2.0, 8.8 Hz, aromatic), 8.03 (d, 1H, J=2.0 Hz, aromatic).

Reference Example 1-2A

Concentrated hydrochloric acid (2.00 mL, 24.0 mmol) and anhydrous tin dichloride (2.50 g, 13.1 mmol) were added sequentially at 0° C. to a methanol (10 mL) solution of 1-[2-nitro-4-(trifluoromethyl)phenyl]piperidine (559 mg, 2.03 mmol) obtained in Reference example 1-1A. The mixture was left to room temperature and then stirred for 17.5 hours. An aqueous saturated solution of sodium bicarbonate was added to the mixture. The mixture was subjected to extraction with ethyl acetate (×3). The thus obtained organic layer was washed with brine, dried on $Na_2SO_4$, filtered, and then concentrated under reduced pressure. The residue was purified by silica gel column chromatography (50 g, hexane/ethyl acetate=14/1), so that 2-(1-piperidinyl)-5-(trifluoromethyl) aniline (448 mg, 1.83 mmol, 90.4%) was obtained as light yellow solid.

The results of TLC and $^1$H NMR ($CDCl_3$, 400 MHz) are as follows. TLC $R_f$ 0.30 (hexane/acetone=18/1); $^1$H NMR ($CDCl_3$, 400 MHz) δ 1.59-1.60 (m, 2H, $CH_2$), 1.71 (tt, 4H, J=5.4, 5.4 Hz, $2CH_2$), 2.85 (brs, 4H, $2CH_2$), 4.09 (brs, 2H, $NH_2$), 6.92 (d, 1H, J=1.9 Hz, aromatic), 6.97 (dd, 1H, J=1.9, 8.4 Hz, aromatic), 7.01 (d, 1H, J=8.4 Hz, aromatic).

Reference Example 1-3A

Isonicotinoyl chloride hydrochloride (151 mg, 0.850 mmol; commercial product), triethylamine (450 μL, 3.23 mmol), and 4-(dimethylamino)pyridine in a catalyst amount were added sequentially at 0° C. to a dichloromethane (5 mL) solution of 2-(1-piperidinyl)-5-(trifluoromethyl)aniline (173 mg, 0.708 mmol) obtained in Reference example 1-2A. The mixture was left to room temperature and then stirred for 19.5 hours. Water was added to the mixture and then the mixture was subjected to extraction with ethyl acetate (×3). The thus obtained organic layer was washed with an aqueous saturated solution of sodium bicarbonate, dried on $Na_2SO_4$, filtered, and then concentrated under reduced pressure. The residue was purified by silica gel column chromatography (10 g, hexane/ethyl acetate=1.5/1) and recrystallization (hexane), so that N-[2-(1-piperidinyl)-5-(trifluoromethyl)phenyl] isonicotinamide (Compound 1) (83.8 mg, 0.240 mmol, 33.9%) was obtained as colorless solid.

The results of the melting point, TLC, $^1$H NMR ($CDCl_3$, 400 MHz), and IR are as follows.

Melting point 96-98° C.; TLC $R_f$ 0.40 (hexane/ethyl acetate=1/1); $^1$H NMR ($CDCl_3$, 400 MHz) δ1.67-1.68 (m, 2H, $CH_2$), 1.78 (tt, 4H, J=5.5, 5.5 Hz, $2CH_2$), 2.88 (t, 4H, J=5.5 Hz, $2CH_2$), 7.29 (d, 1H, J=8.2 Hz, aromatic), 7.40 (dd, 1H, J=1.8, 8.2 Hz, aromatic), 7.76 (dd, 2H, J=2.0, 4.4 Hz, aromatic), 8.86 (dd, 2H, J=2.0, 4.4 Hz, aromatic), 8.87 (d, 1H, J=1.8 Hz, aromatic), 9.53 (s, 1H, NH); IR (KBr, $cm^{-1}$) 497, 586, 648, 682, 750, 887, 881, 898, 918, 931, 1026, 1074, 1122, 1167, 1246, 1336, 1379, 1408, 1441, 1462, 1531, 1556, 1587, 1682, 2818, 2851, 2941, 3323.

Reference Example 1-1B

Piperidine (5.50 mL, 55.5 mmol; commercial product) was added at 0° C. to a N,N-dimethylformamide (DMF) (7 mL) solution of 1-chloro-2-nitro-4-(trifluoro-methyl)benzene (5.00 g, 22.4 mmol; commercial product). The mixture was stirred for 40 minutes. Water was added to the mixture. The mixture was then extracted with ethyl acetate (×3). The thus obtained organic layer was washed with saturated sodium chloride solution, dried using anhydrous sodium sulfate, filtered, and then concentrated under reduced pressure. The residue was purified by silica gel column chromatography (200 g, hexane/ethyl acetate=8/1), so that 1-[2-nitro-4-(trifluoromethyl)phenyl]-piperidine (6.13 g, quant.) was obtained as orange solid.

Reference Example 1-2B

Concentrated hydrochloric acid (12.2 mL, 146 mmol) and anhydrous tin dichloride (12.7 g, 67.2 mmol) were added sequentially at 0° C. to a dichloromethane (10 mL) solution of 1-[2-nitro-4-(trifluoromethyl)phenyl]piperidine (6.13 g, 22.4 mmol) obtained in Reference example 1-1B. The mixture was stirred for 7 hours. Water was added to the mixture and then the mixture was subjected to extraction with ethyl acetate (×3). The thus obtained organic layer was washed with saturated sodium chloride solution, dried using anhydrous sodium sulfate, filtered, and then concentrated under reduced pressure. The residue was purified by silica gel column chromatography (200 g, hexane/ethyl acetate=15/1), so that 2-(1-piperidinyl)-5-(trifluoromethyl)aniline (4.55 g, 83.0%) was obtained as light yellow solid.

Reference Example 1-3B

Isonicotinoyl chloride hydrochloride (6.48 g, 36.4 mmol; commercial product) and triethylamine (5.57 mL, 54.6 mmol) were added sequentially at 0° C. to a dichloromethane (10 mL) solution of 2-(1-piperidinyl)-5-(trifluoromethyl)

aniline (4.45 g, 18.2 mmol) obtained in Reference example 1-2B. The mixture was stirred for 0.5 hours. Water was added to the mixture and then the mixture was subjected to extraction with ethyl acetate (×3). The thus obtained organic layer was washed with saturated sodium chloride solution, dried using anhydrous sodium sulfate, filtered, and then concentrated under reduced pressure. The residue was purified by silica gel column chromatography (200 g, hexane/ethyl acetate=1/1) and recrystallization (hexane), so that N-[2-(1-piperidinyl)-5-(trifluoromethyl)phenyl]isonicotinamide (Compound 1) (5.49 g, 86.3%) was obtained as colorless solid.

The results of the melting point, TLC, $^1$H NMR (CDCl$_3$, 400 MHz), and IR are as follows.

Melting point 108-109° C.; TLC R$_f$ 0.27 (hexane/ethyl acetate=1/1); $^1$H NMR (CDCl$_3$, 400 MHz) δ1.61-1.62 (m, 2H, CH$_2$), 1.68 (tt, 4H, J=5.0, 5.0 Hz, 2CH$_2$), 2.87 (t, 4H, J=5.0 Hz, 2CH$_2$), 7.32 (d, 1H, J=7.8 Hz, aromatic), 7.51 (dd, 1H, J=1.6, 7.8 Hz, aromatic), 7.71 (dd, 2H, J=1.6, 6.4 Hz, aromatic), 8.76 (dd, 2H, J=1.6, 6.4 Hz, aromatic), 9.58 (d, 1H, J=1.6 Hz, aromatic), 10.5 (s, 1H, NH); IR (KBr, cm$^{-1}$) 741, 826, 891, 1013, 1076, 1125, 1167, 1233, 1271, 1335, 1377, 1410, 1437, 1462, 1526, 1591, 1616, 2820, 2851, 2938, 3163.

Reference Example 2

Synthesis of Compound 2

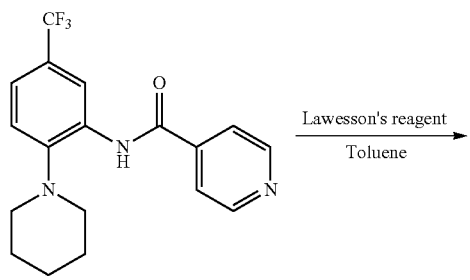

Reference example 1-3
Compound 1

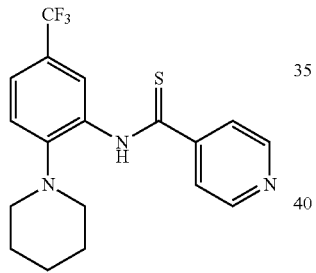

Reference example 2
Compound 2

Lawesson's reagent (328 mg, 0.811 mmol; commercial product) was added to a toluene (2.5 mL) solution of N-[2-(1-piperidinyl)-5-(trifluoromethyl)phenyl]-isonicotinamide (Compound 1) (528 mg, 1.51 mmol) obtained in Reference example 1-3. The mixture was stirred under reflux at 100° C. for 12 hours. After the mixture was left to room temperature, a 2 M aqueous sodium hydroxide solution was added to the mixture, so as to make it alkaline. The mixture was further subjected to backward extraction with a 12 M aqueous sodium hydroxide solution (×3). Hydrochloric acid (2 M) was added to the thus obtained aqueous layer, so as to make it acidic. Then the mixture was subjected to extraction with ether (×3). The thus obtained organic layer was washed with saturated sodium chloride solution, dried using anhydrous sodium sulfate, filtered, and then concentrated under reduced pressure. The residue was purified by silica gel column chromatography (50 g, hexane/ethyl acetate=1/1), so that N-[2-(1-piperidinyl)-5-(trifluoromethyl)phenyl]isonicotinthioamide (Compound 2) (186 mg, 33.7%) was obtained as a colorless solid.

Reference Example 3

Synthesis of Compound 3

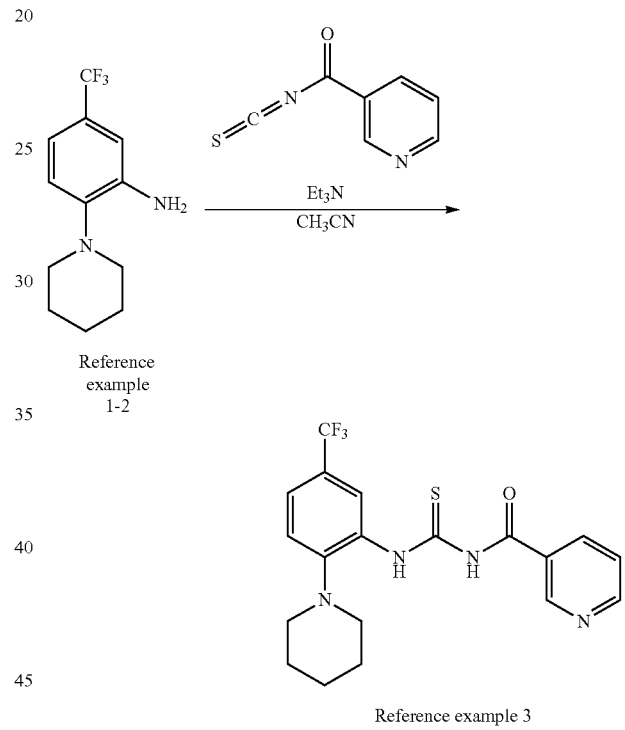

Reference example 3
Compound 3

An acetonitrile (15 mL) solution of potassium thiocyanate (commercial product) (198 mg, 2.04 mmol) and nicotinoyl chloride hydrochloride (272 mg, 1.53 mmol; commercial product) was stirred at 80° C. for 1 hour. The mixture was left to room temperature. 2-(1-Piperidinyl)-5-(trifluoromethyl) aniline (250 mg, 1.02 mmol) obtained in Reference example 1-2 and triethylamine (285 μL, 2.04 mmol) were added sequentially to the mixture. The mixture was stirred at 50° C. for 1 hour. The mixture was poured into an aqueous saturated sodium bicarbonate solution and then the mixture was subjected to extraction with dichloromethane (×3). The thus obtained organic layer was washed with water, dried using anhydrous sodium sulfate, filtered, and then concentrated under reduced pressure. The residue was purified by silica gel column chromatography (30 g, hexane/ethyl acetate/dichloromethane=6/3/4), so that 1-nicotinoyl-3-[2-(1-piperidinyl)-5-(trifluoromethyl)phenyl]thiourea (Compound 3) (70.7 mg, 30.1%) was obtained as light yellow solid.

The results of the melting point, TLC, ¹H NMR (CD₃OD, 400 MHz), and IR are as follows.

Melting point 155-156° C.; TLC R_f 0.21 (hexane/ethyl acetate/dichloromethane=4/3/3); ¹H NMR (CDCl₃, 300 MHz) δ1.61 (m, 2H, J=5.3 Hz, CH₂), 1.81 (m, 4H, J=5.3 Hz, 2CH₂), 2.89 (t, 4H, J=5.3 Hz, 2CH₂), 7.24 (d, 1H, J=8.4 Hz, aromatic), 7.47 (dd, 1H, J=2.4, 8.4 Hz, aromatic), 7.52 (dd, 1H, J=4.8, 8.0 Hz, aromatic), 8.23 (ddd, 1H, J=1.7, 1.7, 8.0 Hz, aromatic), 8.89 (dd, 1H, J=1.7, 4.8 Hz, aromatic), 9.09 (br s, 2H, aromatic, NH), 9.18 (d, 1H, J=2.4 Hz, aromatic), 12.9 (br s, 1H, NH); IR (KBr, cm⁻¹) 644, 704, 731, 804, 826, 883, 908, 1026, 1078, 1123, 1165, 1204, 1221, 1271, 1298, 1335, 1439, 1479, 1531, 1587, 1614, 1678, 2814, 2855, 2940.

Reference Example 4

Synthesis of Compound 4

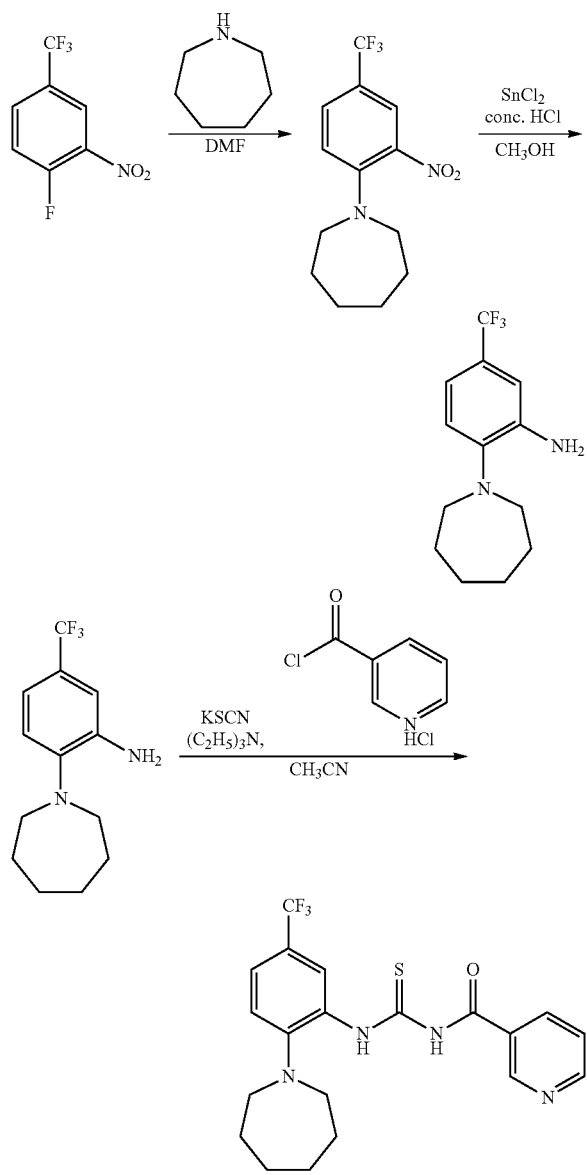

Compound 4

Hexamethyleneimine (673 µL, 5.98 mmol) was added at 0° C. to a N,N-dimethylformamide (4 mL) solution of 1-fluoro-2-nitro-4-(trifluoromethyl)benzene (500 mg, 2.39 mmol; commercial product). The mixture was left to room temperature and then stirred for 1 hour. Water was added to the mixture, and then the mixture was subjected to extraction three times with ethyl acetate. The extracted organic mixture was washed with saturated sodium chloride solution, dried on anhydrous sodium sulfate, subjected to suction filtration, and then concentrated under reduced pressure. The residue was purified by silica gel column chromatography (hexane/ethyl acetate=10/1), so that 1-[2-Nitro-4-(trifluoromethyl)phenyl] hexamethyleneimine (696 mg, quant.) was obtained as orange oil.

The results of TLC and ¹H NMR (CDCl₃, 400 MHz) are as follows. TLC R_f 0.38 (hexane/ethyl acetate=10/1); ¹H NMR (CDCl₃, 400 MHz) δ 1.58-1.61 (m, 4H, 2CH₂), 1.84 (s, 4H, 2CH₂), 3.31 (t, 4H, J=5.6 Hz, 2CH₂), 7.11 (d, 1H, J=9.2 Hz, aromatic), 7.53 (d, 1H, J=9.2 Hz, aromatic), 7.98 (s, 1H, aromatic).

12 N HCl (0.94 mL, 11.3 mmol) and SnCl₂ (1.15 g, 6.06 mmol) were added sequentially at 0° C. to a methanol (5 mL) solution of 1-[2-nitro-4-(trifluoromethyl)-phenyl]hexamethyleneimine (500 mg, 1.73 mmol). The mixture was left to room temperature and then stirred for 2 hours. An aqueous saturated solution of sodium bicarbonate was added to the mixture, followed by suction filtration. The mixture was subjected to extraction three times with ethyl acetate. The thus extracted organic mixture was washed with saturated sodium chloride solution, dried on anhydrous sodium sulfate, subjected to suction filtration, and then concentrated under reduced pressure. The residue was purified by silica gel column chromatography (hexane/ethyl acetate=15/1), so that 2-(azacycloheptan-1-yl)-5-(trifluoromethyl)aniline (356 mg, 79.8%) was obtained as orange oil.

The results of TLC and ¹H NMR (CDCl₃, 400 MHz) are as follows. TLC R_f 0.38 (hexane/ethyl acetate=10/1); ¹H NMR (CDCl₃, 400 MHz) δ 1.72-1.79 (m, 8H, 4CH₂), 3.04 (t, 4H, J=6.0 Hz, 2CH₂), 4.09 (s, 2H, NH₂), 6.92 (d, 1H, J=1.2 Hz, aromatic), 6.93 (dd, 1H, J=1.2, 8.0 Hz, aromatic), 7.05 (d, 1H, J=8.0 Hz, aromatic).

Nicotinoyl chloride hydrochloride (356 mg, 2.00 mmol) was added to an acetonitrile solution (15 mL) of potassium thiocyanate (97.2 mg, 1.00 mmol) and then the mixture was stirred at 70° C. for 40 minutes. The organic mixture was left to room temperature. An acetonitrile (5 mL) solution of 2-(azacycloheptan-1-yl)-5-(trifluoromethyl)aniline (258 mg, 1.00 mmol) and triethylamine (279 µL, 2.00 mmol) were added sequentially. The reaction solution was heated to 50° C. and then stirred for 1 hour. The organic mixture was left to room temperature and then water was added to the solution. The mixture was subjected to extraction three times with ethyl acetate, washed with saturated sodium chloride solution, dried on anhydrous sodium sulfate, subjected to suction filtration, and then concentrated under reduced pressure. The residue was purified by silica gel column chromatography (hexane/ethyl acetate=2/1), so that N-nicotinoyl-N'[2-(azacycloheptan-1-yl)-5-(trifluoromethyl)phenyl]thiourea (Compound 4) (406 mg, 96.1%) was obtained as yellow solid.

The results of the melting point, TLC, ¹H NMR (CDCl₃, 400 MHz), and IR are as follows.

Melting point 42-45° C.; TLC R_f 0.43 (hexane/ethyl acetate=1/1); ¹H NMR (CDCl₃, 400 MHz) δ 1.72-1.74 (m, 4H, 2CH₂), 1.79-1.83 (m, 4H, 2CH₂), 3.18 (t, 4H, J=5.6 Hz, 2CH₂), 7.22 (d, 1H, J=8.4 Hz, aromatic), 7.44 (d, 1H, J=8.4 Hz, aromatic), 7.50 (m, 1H, aromatic), 8.20-8.23 (m, 1H, aromatic), 8.68 (s, 1H, aromatic), 8.89 (dd, 1H, J=1.6, 4.6 Hz, aromatic), 9.06 (s, 1H, NH), 9.17 (m, 1H, aromatic), 12.5 (s, 1H, NH); IR (KBr, cm$^{-1}$) 704, 739, 824, 876, 893, 1024, 1078, 1121, 1163, 1196, 1217, 1265, 1331, 1389, 1420, 1439, 1477, 1533, 1589, 1614, 1676, 2855, 2930, 3150.

Reference Example 5

Synthesis of Compound 5

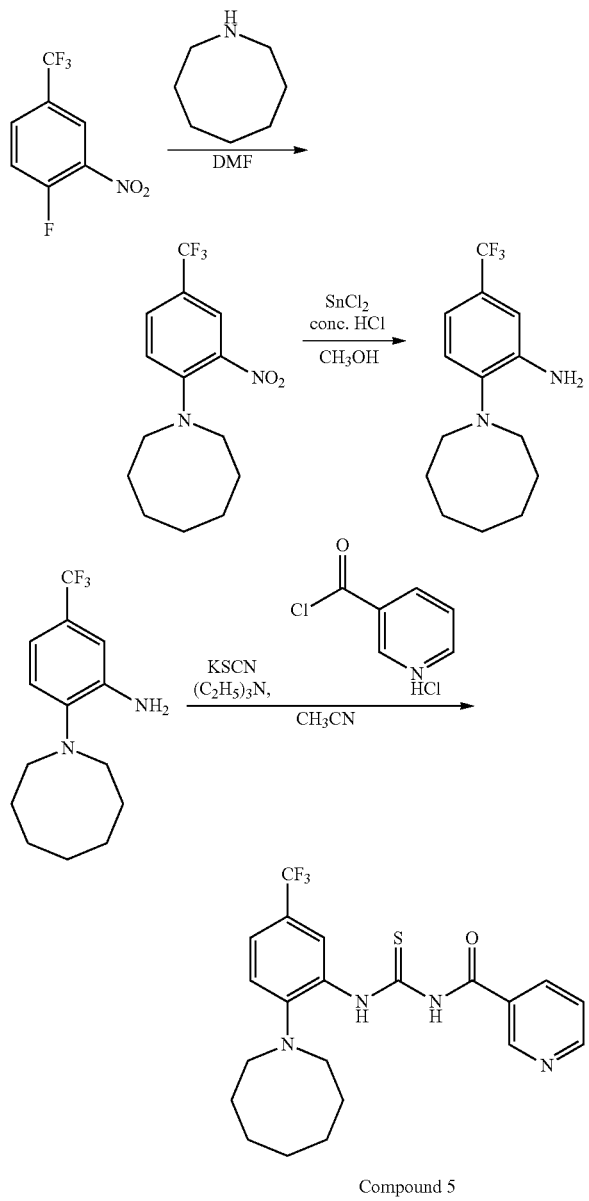

Compound 5

Heptamethyleneimine (760 μL, 5.98 mmol) was added at 0° C. to a N,N-dimethylformamide (4 mL) solution of 1-fluoro-2-nitro-4-(trifluoromethyl)benzene (550 mg, 2.63 mmol; commercial product). The mixture was left to room temperature and then stirred for 1 hour. Water was added to the mixture and then the mixture was subjected to extraction three times with ethyl acetate. The thus extracted organic mixture was washed with saturated sodium chloride solution, dried on anhydrous sodium sulfate, subjected to suction filtration, and then concentrated under reduced pressure. The residue was purified by silica gel column chromatography (hexane/ethyl acetate=10/1), so that 1-[2-nitro-4-(trifluoromethyl)phenyl]heptamethyleneimine (794 mg, quant.) was obtained as orange oil.

The results of TLC and $^1$H NMR (CDCl$_3$, 400 MHz) are as follows. TLC R$_f$ 0.44 (hexane/ethyl acetate=10/1); $^1$H NMR (CDCl$_3$, 400 MHz) δ 1.53 (m, 6H, 3CH$_2$), 1.77 (m, 4H, 2CH$_2$), 3.40 (t, 4H, J=5.8 Hz, 2CH$_2$), 7.14 (d, 1H, J=9.0 Hz, aromatic), 7.54 (d, 1H, J=9.0 Hz, aromatic), 7.90 (s, 1H, aromatic).

12N HCl (890 μL, 10.7 mmol) and SnCl$_2$ (1.10 g, 5.78 mmol) were added sequentially at 0° C. to a methanol (6 mL) solution of 1-[2-nitro-4-(trifluoromethyl)-phenyl]heptamethyleneimine (500 mg, 1.65 mmol). The mixture was left to room temperature and then stirred for 1 hour. An aqueous saturated solution of sodium bicarbonate was added to the mixture, followed by suction filtration. The mixture was subjected to extraction three times with ethyl acetate. The thus extracted organic mixture was washed with saturated sodium chloride solution, dried on anhydrous sodium sulfate, subjected to suction filtration, and then concentrated under reduced pressure.

The residue was purified by silica gel column chromatography (hexane/ethyl acetate=15/1), so that 2-(azacyclooctan-1-yl)-5-(trifluoromethyl)aniline (323 mg, 71.7%) was obtained as orange oil.

The results of TLC and $^1$H NMR (CDCl$_3$, 400 MHz) are as follows. TLC R$_f$ 0.44 (hexane/ethyl acetate=10/1); $^1$H NMR (CDCl$_3$, 400 MHz) δ 1.69-1.80 (br s, 10H, 5CH$_2$), 2.98-3.10 (br s, 4H, 2CH$_2$), 4.21 (s, 2H, NH$_2$), 6.94-6.96 (m, 2H, aromatic), 7.12 (d, 1H, J=8.3 Hz, aromatic).

Nicotinoyl chloride hydrochloride (356 mg, 2.00 mmol) was added to an acetonitrile solution (15 mL) of potassium thiocyanate (97.2 mg, 1.00 mmol). The mixture was stirred at 70° C. for 40 minutes. The organic mixture was left to room temperature. An acetonitrile (5 mL) solution of 2-(azacyclooctan-1-yl)-5-(trifluoromethyl)aniline (272 mg, 1.00 mmol) and triethylamine (278 μL, 2.00 mmol) were added sequentially and then the reaction solution was stirred at room temperature for 1 hour. The organic mixture was left to room temperature and then water was added thereto. The mixture was subjected to extraction three times with ethyl acetate, washed with saturated sodium chloride solution, dried on anhydrous sodium sulfate, subjected to suction filtration, and then concentrated under reduced pressure. The residue was purified by silica gel column chromatography (hexane/ethyl acetate=2/1), so that N-nicotinoyl-N'-[2-(azacyclooctan-1-yl)-5-(trifluoromethyl)phenyl]thiourea (Compound 5) (405 mg, 92.8%) was obtained as yellow solid.

The results of the melting point, TLC, $^1$H NMR (CDCl$_3$, 400 MHz), and IR are as follows.

Melting point; 102-105° C.; TLC R$_f$ 0.45 (hexane/ethyl acetate=1/1); $^1$H NMR (CDCl$_3$, 400 MHz) δ 1.65-1.76 (m, 10H, 5CH$_2$), 2.98-3.10 (m, 4H, 2CH$_2$), 7.22 (d, 1H, J=8.8 Hz, aromatic), 7.44 (d, 1H, J=8.4 Hz, aromatic), 7.50-7.53 (m, 1H, aromatic), 8.21 (m, 1H, aromatic), 8.28 (s, 1H, aromatic), 8.89 (d, 1H, J=4.8 Hz, aromatic), 9.11 (s, 1H, NH), 9.17 (d, 1H, J=2.4 Hz, aromatic), 12.1 (s, 1H, NH); $^{13}$C NMR (CDCl$_3$, 100 MHz) δ 25.3 (2C), 27.0, 27.4 (2C), 53.7 (2C), 120.5, 122.6 (q, J=32.8 Hz), 123.8, 124.5 (d, J=4.1 Hz), 124.6 (d, J=4.1 Hz), 125.5, 127.8, 129.5, 135.4, 148.8, 150.5, 154.2, 165.1, 178.4; IR (KBr, cm$^{-1}$) 610, 702, 739, 806, 858, 891, 962, 1024, 1082, 1117, 1165, 1206, 1271, 1333, 1395, 1420, 1530, 1589, 1616, 1676, 2851, 2924, 3156; MS (EI) m/z 436 (M$^+$).

Reference Example 6

Synthesis of Compound 6

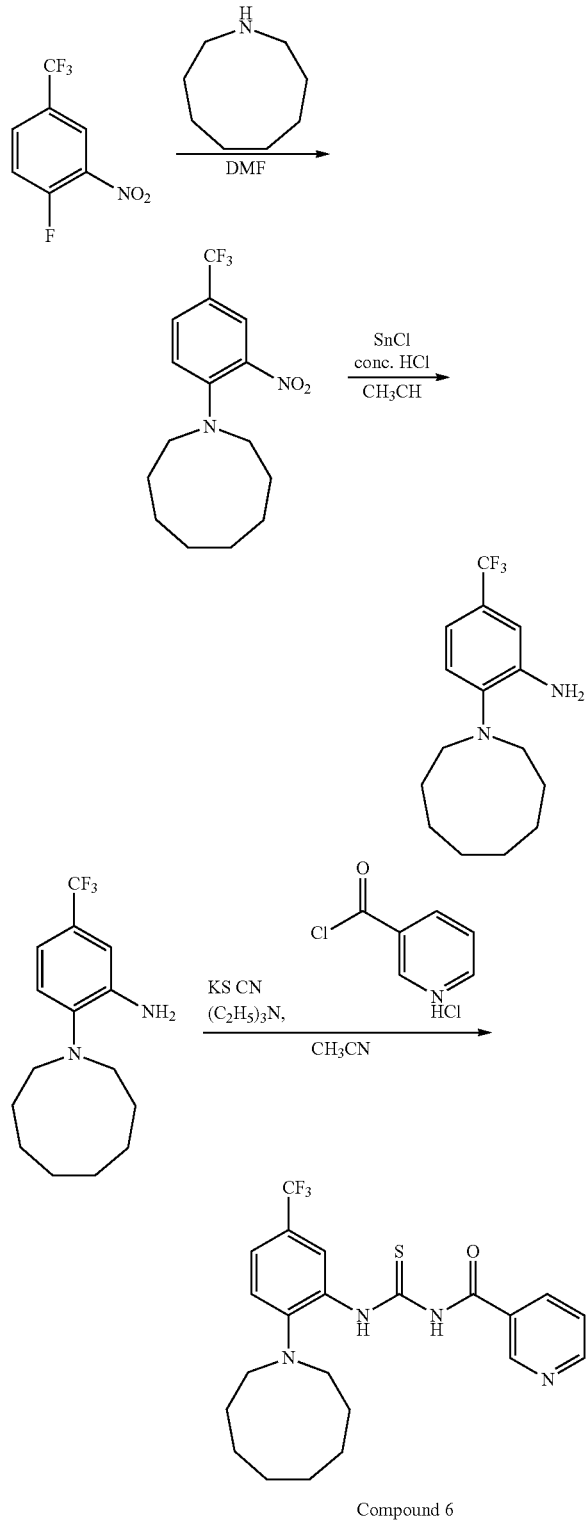

Compound 6

Octamethyleneimine (855 µL, 5.98 mmol) was added at 0° C. to a N,N-dimethylformamide (4 mL) solution of 1-fluoro-2-nitro-4-(trifluoromethyl)benzene (500 mg, 2.39 mmol; commercial product). The mixture was left to room temperature and then stirred for 1.5 hours. Water was added to the mixture, and then the mixture was subjected to extraction three times with ethyl acetate. The thus extracted organic mixture was washed with saturated sodium chloride solution, dried on anhydrous sodium sulfate, subjected to suction filtration, and then concentrated under reduced pressure. The residue was purified by silica gel column chromatography (hexane/ethyl acetate=10/1), so that 1-[2-nitro-4-(trifluoromethyl)phenyl]octamethyleneimine (771 mg, quant.) was obtained as orange oil.

The results of TLC and $^1$H NMR (CDCl$_3$, 400 MHz) are as follows. TLC R$_f$ 0.42 (hexane/ethyl acetate=10/1); $^1$H NMR (CDCl$_3$, 400 MHz) δ 1.47-1.60 (m, 8H, 4CH$_2$), 1.70-1.76 (m, 4H, 2CH$_2$), 3.44 (t, 4H, J=4.0 Hz, 2CH$_2$), 7.19 (d, 1H, J=8.0 Hz, aromatic), 7.56 (d, 1H, J=8.0 Hz, aromatic), 7.89 (s, aromatic).

12 N HCl (860 µL, 10.3 mmol) and SnCl$_2$ (1.05 g, 5.53 mmol) were added sequentially at 0° C. to a methanol (6 mL) solution of 1-[2-nitro-4-(trifluoromethyl)-phenyl]octamethyleneimine (500 mg, 1.58 mmol). The mixture was left to room temperature and then stirred for 2 hours. An aqueous saturated solution of sodium bicarbonate was added to the mixture, followed by suction filtration. The mixture was subjected to extraction three times with ethyl acetate. The thus extracted organic mixture was washed with saturated sodium chloride solution, dried on anhydrous sodium sulfate, subjected to suction filtration, and then concentrated under reduced pressure. The residue was purified by silica gel column chromatography (hexane/ethyl acetate=15/1), so that 2-(azacyclononan-1-yl)-5-(trifluoromethyl)aniline (200 mg, 44.2%) was obtained as orange oil.

The results of TLC and $^1$H NMR (CDCl$_3$, 400 MHz) are as follows. TLC R$_f$ 0.30 (hexane/ethyl acetate=10/1); $^1$H NMR (CDCl$_3$, 400 MHz) δ 1.61-1.71 (m, 12H, 6CH$_2$), 3.01 (t, 4H, J=5.2 Hz, 2CH$_2$), 4.25 (s, 2H, NH$_2$), 6.93-6.97 (m, 2H, aromatic), 7.18 (d, 1H, J=8.0 Hz, aromatic).

Nicotinoyl chloride hydrochloride (125 mg, 0.700 mmol) was added to an acetonitrile solution (6 mL) of potassium thiocyanate (34.0 mg, 0.350 mmol) and then the mixture was stirred at 70° C. for 40 minutes. The organic mixture was left to room temperature. An acetonitrile (2 mL) solution of 2-(azacyclononan-1-yl)-5-(trifluoro-methyl)aniline (100 mg, 0.349 mmol) and triethylamine (97.6 µL, 0.700 mmol) were added sequentially, followed by 1 hour of stirring at room temperature. The organic mixture was left to room temperature and then water was added thereto. The mixture was subjected to extraction three times with ethyl acetate, washed with saturated sodium chloride solution, dried on anhydrous sodium sulfate, subjected to suction filtration, and then concentrated under reduced pressure. The residue was purified by silica gel column chromatography (hexane/ethyl acetate=2/1), so that N-nicotinoyl-N'-[2-(azacyclononan-1-yl)-5-(trifluoromethyl)phenyl]thiourea (Compound 6) (146 mg, 92.9%) was obtained as a yellow solid.

The results of the melting point, TLC, $^1$H NMR (CDCl$_3$, 400 MHz), and IR are as follows.

Melting point 57-59° C.; TLC R$_f$ 0.52 (hexane/ethyl acetate=1/1); $^1$H NMR (CDCl$_3$, 400 MHz) δ 1.58 (m, 4H, 2CH$_2$), 1.67 (m, 8H, 4CH$_2$), 3.31 (m, 4H, 2CH$_2$), 7.22 (d, 1H, J=8.4 Hz, aromatic), 7.46 (dd, 1H, J=1.9, 8.4 Hz, aromatic), 7.52 (dd, 1H, J=5.0, 7.8 Hz, aromatic), 7.97 (d, 1H, J=1.9 Hz, aromatic), 8.20 (ddd, 1H, J=1.6, 2.0, 7.8 Hz, aromatic), 8.90 (dd, 1H, J=1.6, 5.0 Hz, aromatic), 9.12 (s, 1H, NH), 9.16 (d, 1H, J=2.0 Hz, aromatic) 11.9 (s, 1H, NH); $^{13}$C NMR (CDCl$_3$, 100 MHz) δ 24.3 (2C), 26.6 (2C), 27.4 (2C), 53.5 (2C), 120.0, 122.3 (q, J=32.8 Hz), 123.8, 125.0 (d, J=4.1 Hz), 125.5, 126.5 (d, J=4.1 Hz), 127.8, 129.2, 135.4, 148.8, 150.5, 154.2, 165.3, 179.4; IR (KBr, cm$^{-1}$) 610, 702, 741, 816, 887, 1024, 1084, 1117, 1165, 1219, 1271, 1333, 1395, 1420, 1526, 1589, 1616, 1674, 2853, 2924, 3155; MS (EI) m/z 450 (M$^+$).

Reference Example 7

Synthesis of Compound 7

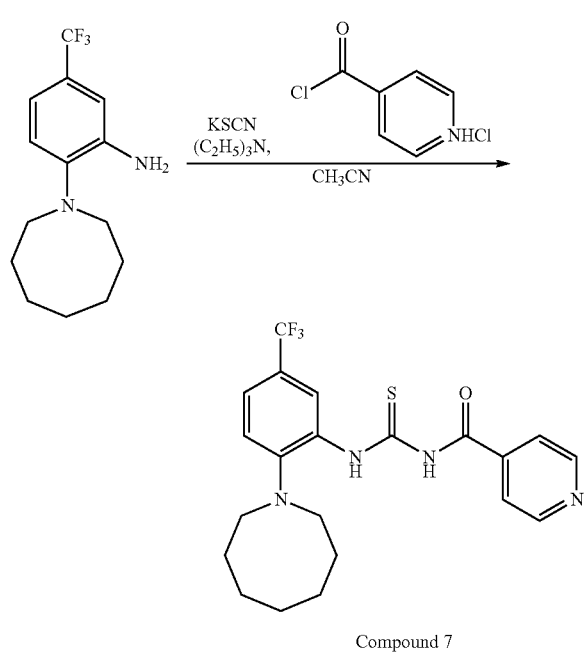

Compound 7

Isonicotinoyl chloride hydrochloride (261 mg, 1.47 mmol) was added to an acetonitrile solution (15 mL) of potassium thiocyanate (70.9 mg, 0.730 mmol) and then the mixture was stirred at 70° C. for 40 minutes. The organic mixture was left to room temperature. An acetonitrile solution (5 mL) of 2-(azacyclooctan-1-yl)-5-(trifluoromethyl)aniline (200 mg, 0.730 mmol) and triethylamine (205 μL, 1.47 mmol) were added sequentially. The reaction solution was heated to 50° C. and then stirred for 1 hour. The organic mixture was left to room temperature and then water was added to the solution. The mixture was subjected to extraction three times with ethyl acetate, washed with saturated sodium chloride solution, dried on anhydrous sodium sulfate, subjected to suction filtration, and then concentrated under reduced pressure. The residue was purified by silica gel column chromatography (hexane/ethyl acetate=1/1), so that (N-isonicotinoyl-N'-[2-(azacyclooctan-1-yl)-5-(trifluoromethyl)phenyl]thiourea (Compound 7) (149 mg, 46.8%) was obtained as yellow solid.

The results for the melting point, TLC, $^1$H NMR (CDCl$_3$, 400 MHz), and IR are as follows.

Melting point 136-139° C.; TLC R$_f$ 0.33 (hexane/ethyl acetate=1/1); $^1$H NMR (CDCl$_3$, 400 MHz) δ 1.65 (m, 6H, 3CH$_2$), 1.75 (m, 4H, 2CH$_2$), 3.29 (t, 4H, J=5.4 Hz, 2CH$_2$), 7.23 (d, 1H, J=8.7 Hz, aromatic), 7.45 (dd, 1H, J=1.7, 8.7 Hz, aromatic), 7.75 (d, 2H, J=6.0 Hz, aromatic), 8.31 (d, 1H, J=1.7 Hz, aromatic), 8.90 (d, 2H, J=6.0 Hz, aromatic), 9.11 (s, 1H, NH), 12.1 (s, 1H, NH); IR (KBr, cm$^{-1}$) 608, 656, 679, 702, 737, 756, 804, 839, 962, 1082, 1117, 1165, 1206, 1271, 1333, 1395, 1437, 1524, 1616, 1680, 2853, 2924, 3154; MS (EI) m/z 436 (M$^+$); Anal. Calcd for C$_{21}$H$_{23}$F$_3$N$_4$OS, C, 57.78; H, 5.31; N, 12.84. Found, C, 57.74; H, 5.42; N, 12.54.

Reference Example 8

Synthesis of Compound 8

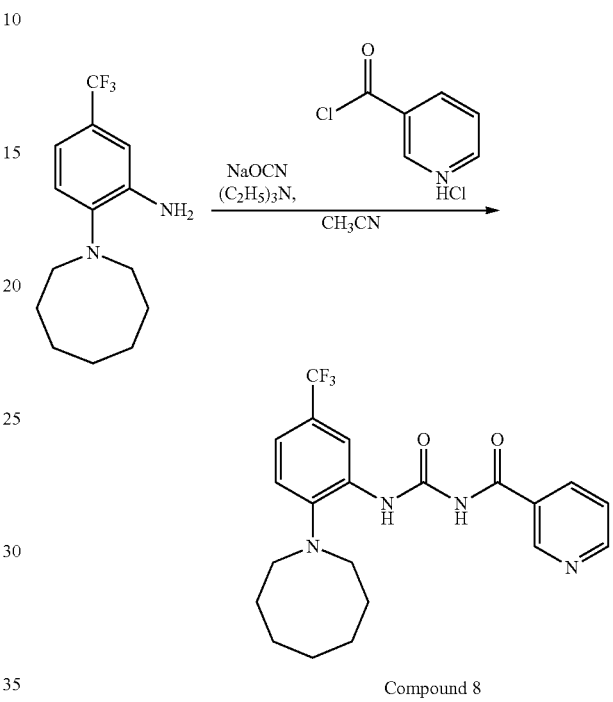

Compound 8

Nicotinoyl chloride hydrochloride (130 mg, 0.730 mmol) was added to an acetonitrile solution (5 mL) of sodium cyanate (47.5 mg, 0.730 mmol) and then the mixture was stirred at 70° C. for 1.5 hours. The organic mixture was left to room temperature. An acetonitrile solution (5 mL) of 2-(azacyclooctan-1-yl)-5-(trifluoromethyl)aniline (100 mg, 0.367 mmol) and triethylamine (103 μL, 0.730 mmol) were added sequentially. The reaction solution was heated to 50° C. and then stirred for 4 hours. The organic mixture was left to room temperature and then water was added to the solution. The mixture was subjected to extraction three times with ethyl acetate, washed with saturated sodium chloride solution, dried on anhydrous sodium sulfate, subjected to suction filtration, and then concentrated under reduced pressure. The residue was purified by silica gel column chromatography (hexane/ethyl acetate=2/1), so that N-nicotinoyl-N'-[2-(azacyclooctan-1-yl)-5-(trifluoro-methyl)phenyl]urea (Compound 8) (80.1 mg, 51.9%) was obtained as colorless solid.

The results of the melting point, TLC, $^1$H NMR (CDCl$_3$, 400 MHz), and IR are as follows.

Melting point 193-196° C.; TLC R$_f$ 0.15 (hexane/ethyl acetate=2/1); $^1$H NMR (CDCl$_3$, 400 MHz) δ 1.73-1.79 (m, 10H, 5CH$_2$), 3.22 (t, 4H, J=5.1 Hz, 2CH$_2$), 7.30 (d, 1H, J=8.2 Hz, aromatic), 7.36 (dd, 1H, J=1.9, 8.5 Hz, aromatic), 7.45 (dd, 1H, J=4.8, 8.0 Hz, aromatic), 8.36-8.39 (m, 2H, aromatic), 8.85 (dd, 1H, J=1.6, 4.8 Hz, aromatic), 9.24 (d, 1H, J=2.2 Hz aromatic), 9.96 (s, 1H, NH), 11.3 (s, 1H, NH); IR (KBr, cm$^{-1}$) 573, 677, 718, 754, 826, 895, 1026, 1078, 1121, 1167, 1217, 1277, 1333, 1435, 1472, 1539, 1585, 1611, 1686, 2853, 2924, 3140; MS (EI) m/z 420 (M+); Anal. Calcd for C$_{21}$H$_{23}$F$_3$N$_4$O$_2$, C, 59.99; H, 5.51; N, 13.33. Found, C, 59.84; H, 5.64; N, 13.03.

Reference Example 9

Synthesis of Compound 9

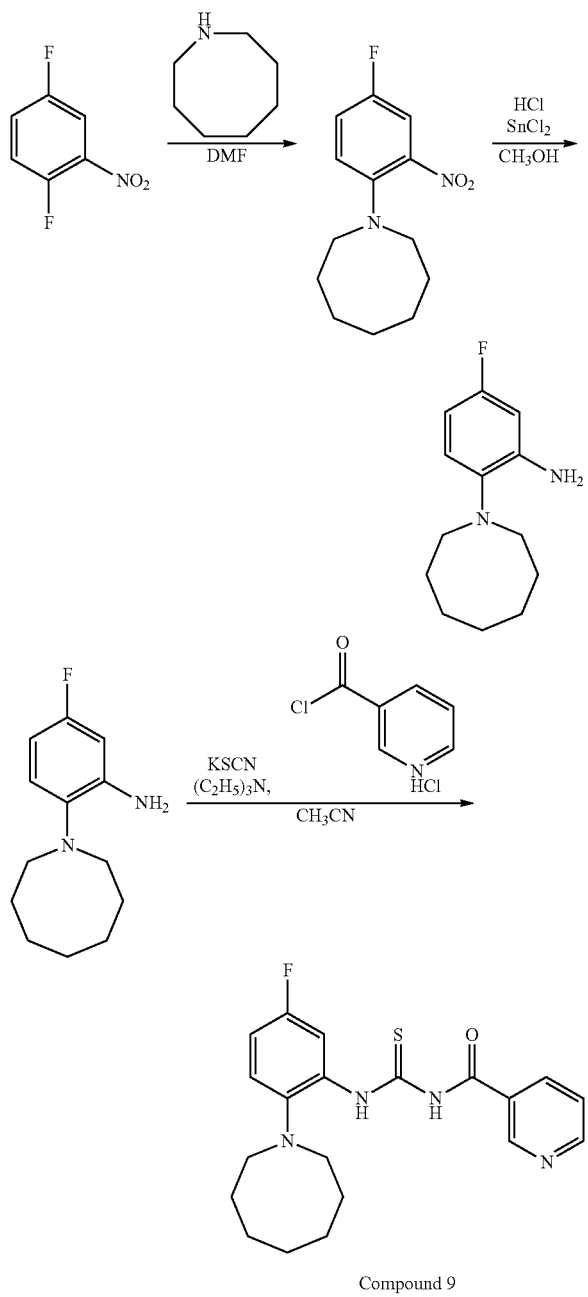

Compound 9

Heptamethyleneimine (1.84 mL, 14.5 mmol) was added at 0° C. to a N,N-dimethylformamide (2.5 mL) solution of 2,5-difluoronitorobenzene (1.00 g, 6.29 mmol; commercial product). The mixture was left to room temperature and stirred for 2 hours. Water was added to the mixture and then the mixture was subjected to extraction three times with ethyl acetate. The thus extracted organic mixture was washed with saturated sodium chloride solution, dried on anhydrous sodium sulfate, subjected to suction filtration, and then concentrated under reduced pressure. The residue was purified by silica gel column chromatography (hexane/ethyl acetate=10/1), so that 1-(4-fluoro-2-nitro-phenyl)heptamethyleneimine (quant.) was obtained as orange oil.

The results of TLC and $^1$H NMR (CDCl$_3$, 400 MHz) are as follows. TLC R$_f$ 0.57 (hexane/ethyl acetate=10/1); $^1$H NMR (CDCl$_3$, 400 MHz) δ 1.54-1.73 (m, 10H, 5CH$_2$), (t, 4H, J=5.8 Hz, 2CH$_2$), 7.12-7.14 (m, 2H, aromatic), 7.34-7.37 (m, 1H, aromatic).

12 N HCl (3.22 mL, 38.6 mmol) and SnCl$_2$ (3.95 g, 20.8 mmol) were added sequentially at 0° C. to a methanol (10 mL) solution of 1-(4-fluoro-2-nitro-phenyl)heptamethyleneimine (1.50 g, 5.95 mmol). The mixture was left to room temperature and then stirred overnight. An aqueous saturated water of sodium bicarbonate was added to the mixture, followed by suction filtration. The mixture was subjected to extraction three times with ethyl acetate. The thus extracted organic mixture was washed with saturated sodium chloride solution, dried on anhydrous sodium sulfate, subjected to suction filtration, and then concentrated under reduced pressure. The residue was purified by silica gel column chromatography (hexane/ethyl acetate=10/1), so that 5-fluoro-2-(azacyclooctan-1-yl)aniline (478 mg, 36.1%) was obtained as yellow oil.

The results of TLC and $^1$H NMR (CDCl$_3$, 400 MHz) are as follows. TLC R$_f$ 0.45 (hexane/ethyl acetate=10/1); $^1$H NMR (CDCl$_3$, 400 MHz) δ 1.71 (s, 10H, 5CH$_2$), 2.95 (s, 4H, 2CH$_2$), 4.23 (s, 2H, NH$_2$), 6.35-6.43 (m, 2H, aromatic), 7.12 (dd, 1H, J=6.0, 8.7 Hz, aromatic).

Nicotinoyl chloride hydrochloride (320 mg, 1.80 mmol) was added to an acetonitrile solution (10 mL) of potassium thiocyanate (87.5 mg, 0.900 mmol). The mixture was stirred at 70° C. for 1 hour. The organic mixture was left to room temperature. An acetonitrile (5 mL) solution of 2-(azacyclooctan-1-yl)-5-fluoroaniline (200 mg, 0.900 mmol) and triethylamine (251 µL, 1.80 mmol) were added sequentially. The reaction solution was heated to 50° C. and then stirred for 4 hours. The organic mixture was left to room temperature and then water was added to the solution. The mixture was subjected to extraction three times with ethyl acetate, washed with saturated sodium chloride solution, dried on anhydrous sodium sulfate, subjected to suction filtration, and then concentrated under reduced pressure. The residue was purified by silica gel column chromatography (hexane/ethyl acetate=2/1), so that N-nicotinoyl-N'-[2-(azacyclooctan-1-yl)-5-(trifluoromethyl)phenyl]thiourea (Compound 9) (117 mg, 33.6%) was obtained as yellow solid.

The results of the melting point, TLC, $^1$H NMR (CDCl$_3$, 400 MHz), and IR are as follows.

Melting point 122-124° C.; TLC R$_f$ 0.30 (hexane/ethyl acetate=1/1); $^1$H NMR (CDCl$_3$, 400 MHz) δ 1.75 (m, 10H, 5CH$_2$), 3.11 (t, 4H, J=5.4 Hz, 2CH$_2$), 6.92 (ddd, 1H, J=0.9, 3.1, 10.4 Hz, aromatic), 7.22 (dd, 1H, J=5.5, 8.7 Hz, aromatic), 7.51 (dd, 1H, J=0.9, 4.8 Hz, aromatic), 8.21 (ddd, 1H, J=1.7, 2.4, 8.7 Hz, aromatic), 8.47 (dd, 1H, J=2.8, 10.4 Hz, aromatic), 8.88 (dd, 1H, J=1.7, 5.5 Hz, aromatic), 9.03 (s, 1H, NH), 9.16 (d, 1H, J=2.4 Hz, aromatic), 12.7 (s, 1H, NH); IR (KBr, cm$^{-1}$) 704, 737, 816, 862, 908, 1024, 1096, 1150, 1198, 1269, 1288, 1346, 1420, 1477, 1530, 1591, 1680, 2849, 2920, 3150; MS (EI) m/z 386 (M+); Anal. Calcd for $C_{20}H_{23}FN_4OS$, C, 62.15; H, 6.00; N, 14.50. Found, C, 61.76; H, 6.04; N, 14.27.

Reference Example 10

Synthesis of Compound 10

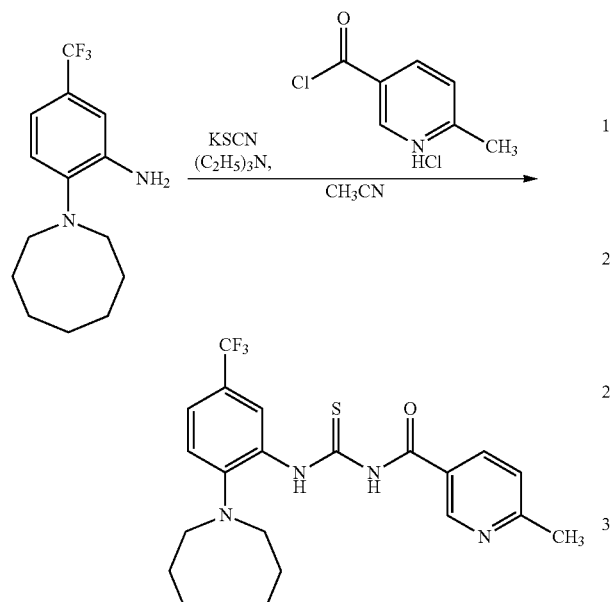

Compound 10

N,N-dimethylformamide (3 drops) and thionyl chloride (643 μL, 8.81 mmol) were added sequentially to a toluene solution (5 mL) of 6-methylnicotinoic acid (252 mg, 1.84 mmol), followed by 4 hours of stirring at 60° C. The organic mixture was left to room temperature and then concentrated under reduced pressure. The thus obtained residue was suspended in acetonitrile (5 mL). Potassium thiocyanate (178 mg, 1.84 mmol) was added to the suspension, followed by 1 hour of stirring at 60° C. The organic mixture was left to room temperature. 2-(Azacyclooctan-1-yl)-5-(trifluoromethyl)aniline (200 mg, 0.734 mmol) and triethylamine (256 μL, 1.84 mmol) were added sequentially. The reaction solution was stirred overnight at room temperature. Water was added to the solution. The thus obtained organic mixture was subjected to extraction three times with ethyl acetate, washed with saturated sodium chloride solution, dried on anhydrous sodium sulfate, filtered, and then concentrated under reduced pressure. The residue was purified by silica gel column chromatography (20 g, hexane/ethyl acetate=2/1), so that N-(6-methylnicotinoyl)-N'-[2-(azacyclo-octan-1-yl)-5-(trifluoromethyl)phenyl]thiourea (Compound 10) (19.2 mg, 5.81%) was obtained as red solid.

The results of the melting point, TLC, $^1$H NMR (CDCl$_3$, 400 MHz), and IR are as follows.

Melting point 57-60° C.; TLC R$_f$ 0.26 (hexane/ethyl acetate=2/1); $^1$H NMR (CDCl$_3$, 400 MHz) δ 1.73-1.76 (m, 10H, 5CH$_2$), 2.69 (s, 3H, CH$_3$), 3.31 (t, 4H, J=5.8 Hz, 2CH$_2$), 7.21 (d, 1H, J=8.5 Hz, aromatic), 7.35 (d, 1H, J=8.0 Hz, aromatic), 7.44 (dd, 1H, J=2.2, 8.5 Hz, aromatic), 8.10 (dd, 1H, J=2.4, 8.0 Hz, aromatic), 8.25 (d, 1H, J=2.2 Hz, aromatic), 9.05 (d, 1H, J=2.4 Hz, aromatic), 9.18 (s, 1H, NH), 12.2 (s, 1H, NH); IR (KBr, cm$^{-1}$) 754, 893, 1024, 1082, 1119, 1167, 1206, 1271, 1333, 1375, 1437, 1489, 1533, 1597, 1614, 1674, 2853, 2924, 3150; MS (EI) m/z 450 (M+).

Reference Example 11

Synthesis of Compound 11

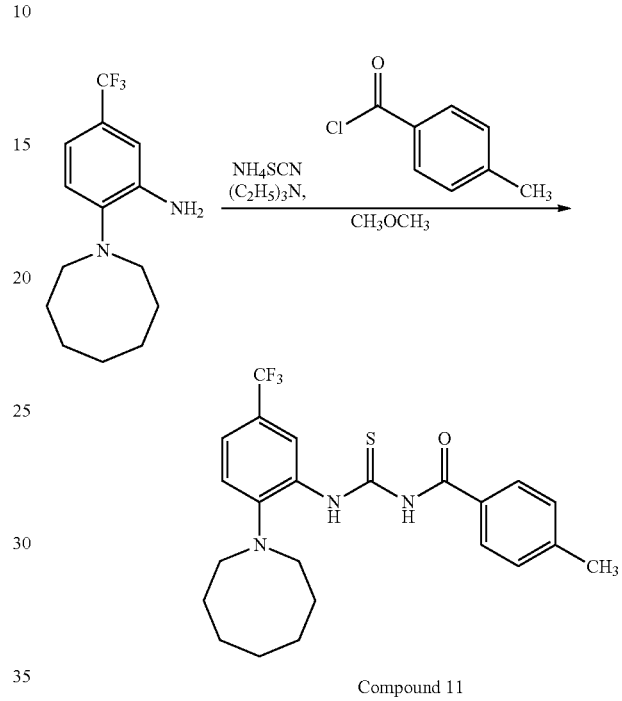

Compound 11

4-Methoxybenzoyl chloride (96.5 μL, 0.730 mmol) was added to an acetone solution (5 mL) of ammonium thiocyanate (55.6 mg, 0.730 mmol), followed by 1 hour of stirring at 60° C. The organic mixture was left to room temperature. 2-(Azacyclooctan-1-yl)-5-(trifluoromethyl)aniline (100 mg, 0.367 mmol) and triethylamine (102 μL, 0.730 mmol) were added sequentially. The reaction solution was stirred at room temperature for 5 hours. Water was added to the solution. The mixture was subjected to extraction three times with ethyl acetate, washed with saturated sodium chloride solution, dried on anhydrous sodium sulfate, subjected to suction filtration, and then concentrated under reduced pressure. The residue was purified by silica gel column chromatography (hexane/ethyl acetate=10/1), so that N-(6-methylbenzoyl)-N'-[2-(azacyclooctan-1-yl)-5-(trifluoromethyl)phenyl]tiourea (Compound 11) (80.4 mg, 48.7%) was obtained as colorless solid.

The results of the melting point, TLC, $^1$H NMR (CDCl$_3$, 400 MHz), and IR are as follows.

Melting point 39-44° C.; TLC R$_f$ 0.25 (hexane/ethyl acetate=10/1); $^1$H NMR (CDCl$_3$, 400 MHz) δ 1.64-1.75 (m, 10H, 5CH$_2$), 2.46 (s, 3H, CH$_3$), 3.31 (t, 4H, J=5.8 Hz, 2CH$_2$), 7.19 (d, 1H, J=8.5 Hz, aromatic), 7.34-7.36 (AA'BB', 2H, aromatic), 7.43 (dd, 1H, J=2.2, 8.5 Hz, aromatic), 8.08-8.11 (AA'BB', 2H, aromatic), 8.21 (d, 1H, J=2.2 Hz, aromatic), 9.13 (s, 1H, NH), 12.3 (s, 1H, NH); $^{13}$C NMR (CDCl$_3$, 100 MHz) δ 21.7, 25.3 (2C), 27.0, 27.4 (2C), 53.7 (2C), 120.2, 122.3 (q, J=32.8 Hz), 124.4 (d, J=3.3 Hz), 125.0 (d, J=3.3 Hz), 125.6, 127.6 (2C), 128.7, 129.5, 129.9 (2C), 144.9, 150.5, 166.5, 178.9; IR (KBr, cm$^{-1}$) 608, 746, 831, 891, 1080, 1119, 1165, 1206, 1263, 1333, 1395, 1452, 1499, 1524, 1611, 1670, 2851, 2924, 3140; MS (EI) m/z 449 (M+); Anal. Calcd for $C_{23}H_{26}F_3N_3OS$, C, 61.45; H, 5.83; N, 9.35. Found, C, 61.51; H, 5.83; N, 9.50.

Reference Example 12

Synthesis of Compound 12

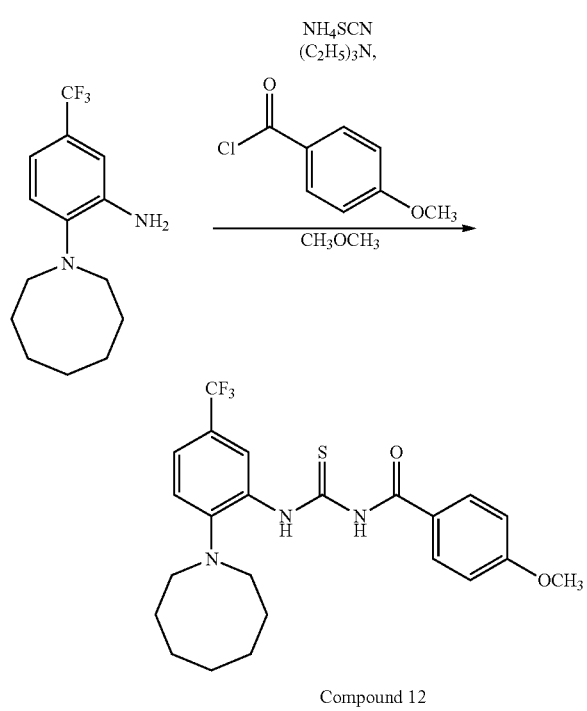

Compound 12

4-Methylbenzoyl chloride (125 mg, 0.730 mmol) was added to an acetone solution (5 mL) of ammonium thiocyanate (55.6 mg, 0.730 mmol), followed by 1 hour of stirring at 60° C. The organic mixture was left to room temperature. 2-(Azacyclooctan-1-yl)-5-(trifluoromethyl)aniline (100 mg, 0.367 mmol) and triethylamine (102 μL, 0.730 mmol) were added sequentially. The reaction solution was stirred at room temperature for 5 hours. Water was added to the solution. The mixture was subjected to extraction three times with ethyl acetate, washed with saturated sodium chloride solution, dried on anhydrous sodium sulfate, subjected to suction filtration, and then concentrated under reduced pressure. The residue was purified by silica gel column chromatography (hexane/ethyl acetate=5/1), so that N-(4-methoxybenzoyl)-N'-[2-(azacyclooctan-1-yl)-5-(trifluoromethyl)phenyl]thiourea (Compound 12) (77.8 mg, 45.5%) was obtained as colorless solid.

The results of the melting point, TLC, $^1$H NMR (CDCl$_3$, 400 MHz), and IR are as follows.

Melting point 39-44° C.; TLC $R_f$ 0.33 (hexane/ethyl acetate=5/1); $^1$H NMR (CDCl$_3$, 400 MHz) δ 1.61-1.75 (m, 10H, 5CH$_2$), 3.32 (t, 4H, J=5.8 Hz, 2CH$_2$), 3.91 (s, 3H, OCH$_3$), 7.01-7.03 (AA'BB', 2H, aromatic), 7.19 (d, 1H, J=8.7 Hz, aromatic), 7.42 (dd, 1H, J=2.2, 8.7 Hz, aromatic), 7.88-7.90 (AA'BB', 2H, aromatic), 8.20 (d, 1H, J=2.2 Hz, aromatic), 9.09 (s, 1H, NH), 12.3 (s, 1H, NH); IR (KBr, cm$^{-1}$) 611, 702, 739, 764, 814, 843, 891, 1028, 1080, 1117, 1173, 1206, 1261, 1333, 1395, 1499, 1533, 1576, 1605, 1668, 2847, 2926, 3142; Anal. Calcd for $C_{23}H_{26}F_3N_3O_2S$, C, 59.34; H, 5.63; N, 9.03. Found, C, 59.00; H, 5.57; N, 8.96.

Reference Example 13

Synthesis of Compound 13

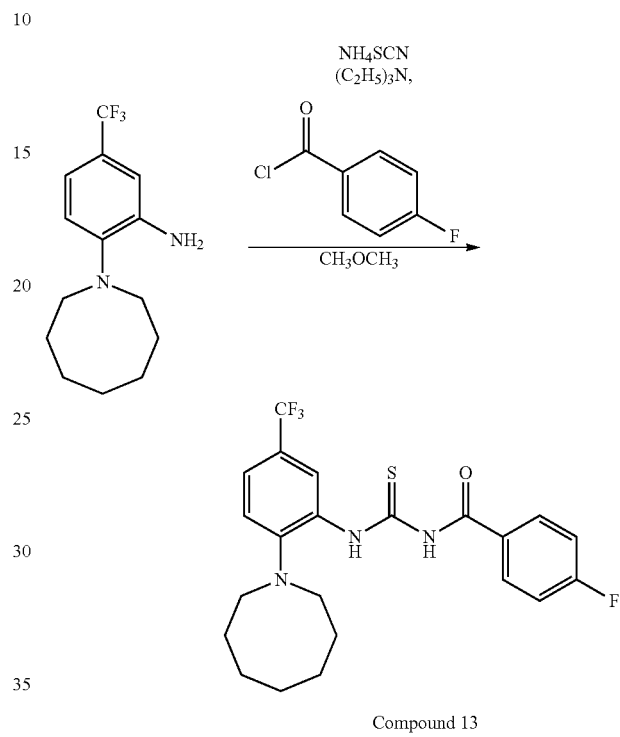

Compound 13

4-Fluorobenzoyl chloride (86.3 μL, 0.730 mmol) was added to an acetone solution (5 mL) of ammonium thiocyanate (55.6 mg, 0.730 mmol), followed by 1 hour of stirring at 60° C. The organic mixture was left to room temperature. 2-(Azacyclooctan-1-yl)-5-(trifluoromethyl)aniline (100 mg, 0.367 mmol) and triethylamine (102 μL, 0.730 mmol) were added sequentially. The reaction solution was stirred at room temperature for 5 hours. Water was added to the solution. The mixture was subjected to extraction three times with ethyl acetate, washed with saturated sodium chloride solution, dried on anhydrous sodium sulfate, subjected to suction filtration, and then concentrated under reduced pressure. The residue was purified by silica gel column chromatography (hexane/ethyl acetate=10/1), so that N-(4-fluorobenzoyl)-N'-[2-(azacyclooctan-1-yl)-5-(trifluoromethyl)phenyl]thiourea (Compound 13) (93.9 mg, 56.4%) was obtained as colorless solid.

The results of the melting point, TLC, $^1$H NMR (CDCl$_3$, 400 MHz), and IR are as follows.

Melting point 95-97° C.; TLC $R_f$ 0.29 (hexane/ethyl acetate=10/1); $^1$H NMR (CDCl$_3$, 400 MHz) δ 1.65-1.75 (m, 10H, 5CH$_2$), 3.31 (t, 4H, J=5.5 Hz, 2CH$_2$), 7.19-7.22 (m, 2H, aromatic), 7.24 (s, 1H, aromatic), 7.43 (dd, 1H, J=2.2, 8.5 Hz, aromatic), 7.95 (dd, 2H, J=5.1, 8.9 Hz, aromatic), 8.24 (d, 1H, J=2.2 Hz, aromatic), 9.01 (s, 1H, NH), 12.2 (s, 1H, NH); IR (KBr, cm$^{-1}$) 604, 700, 762, 816, 849, 891, 1080, 1119, 1161, 1206, 1240, 1263, 1333, 1345, 1499, 1530, 1603, 1672, 2853, 2924, 3154; Anal. Calcd for $C_{22}H_{23}F_4N_3OS$, C, 58.27; H, 5.11; N, 9.27. Found, C, 58.49; H, 5.28; N, 9.40.

Reference Example 14

Synthesis of Compound 14

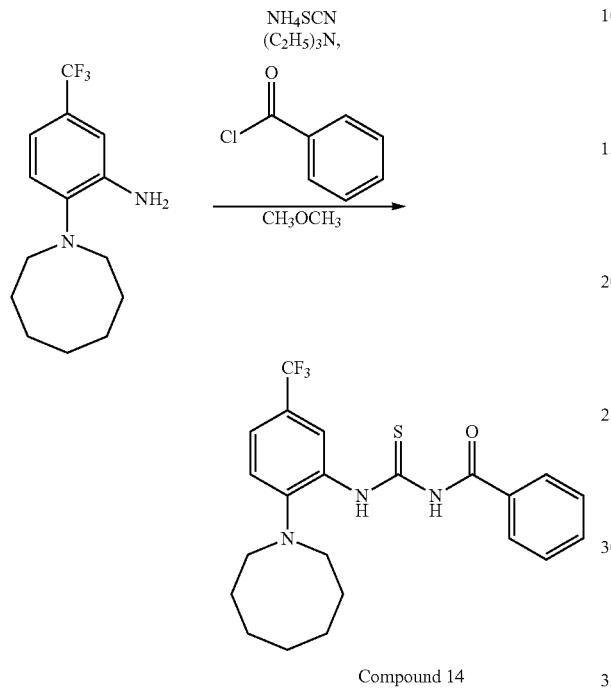

Compound 14

Benzoyl chloride (84.7 µL, 0.730 mmol) was added to an acetone solution (5 mL) of ammonium thiocyanate (55.6 mg, 0.730 mmol), followed by 1.5 hours of stirring at 60° C. The organic mixture was left to room temperature. 2-(Azacyclooctan-1-yl)-5-(trifluoromethyl)aniline (100 mg, 0.367 mmol) and triethylamine (102 µL, 0.730 mmol) were added sequentially. The reaction solution was stirred at room temperature overnight. Water was added to the solution. The mixture was subjected to extraction three times with ethyl acetate, washed with saturated sodium chloride solution, dried on anhydrous sodium sulfate, subjected to suction filtration, and then concentrated under reduced pressure. The residue was purified by silica gel column chromatography (hexane/ethyl acetate=8/1), so that N-benzoyl-N'-[2-(azacyclooctan-1-yl)-5-(trifluoromethyl)phenyl]thiourea (Compound 14) (95.2 mg, 59.6%) was obtained as colorless solid.

The results of the melting point, TLC, $^1$H NMR (CDCl$_3$, 400 MHz), and IR are as follows.

Melting point 92-93° C.; TLC $R_f$ 0.20 (hexane/ethyl acetate=10/1); $^1$H NMR (CDCl$_3$, 400 MHz) δ 1.65-1.76 (m, 10H, 5CH$_2$), 3.31 (t, 4H, J=5.8 Hz, 2CH$_2$), 7.20 (d, 1H, J=8.7 Hz, aromatic), 7.43 (dd, 1H, J=2.0, 8.7 Hz, aromatic), 7.54-7.58 (m, 2H, aromatic), 7.65-7.69 (m, 1H, aromatic), 7.92 (d, 2H, J=7.5 Hz, aromatic), 8.23 (d, 1H, J=2.0 Hz, aromatic), 9.16 (s, 1H, NH), 12.3 (s, 1H, NH); $^{13}$C NMR (CDCl$_3$, 100 MHz) δ 25.3 (2C), 27.1, 27.4 (2C), 53.7 (2C), 120.3, 122.5 (q, J=33.6 Hz), 124.4 (d, J=3.3 Hz), 124.9 (d, J=3.3 Hz), 125.5, 127.5 (2C), 129.2 (2C), 129.5, 131.6, 133.8, 150.6, 166.5, 178.8; IR (KBr, cm$^{-1}$) 606, 656, 689, 708, 806, 1080, 1117, 1148, 1165, 1206, 1263, 1333, 1395, 1449, 1489, 1518, 1578, 1616, 1672, 2851, 2924, 3146; MS (EI) m/z 435 (M$^+$); Anal. Calcd for $C_{22}H_{24}F_3N_3OS$, C, 60.67; H, 5.55; N, 9.65. Found, C, 60.30; H, 5.61; N, 9.54.

Reference Example 15

Synthesis of Compound 15

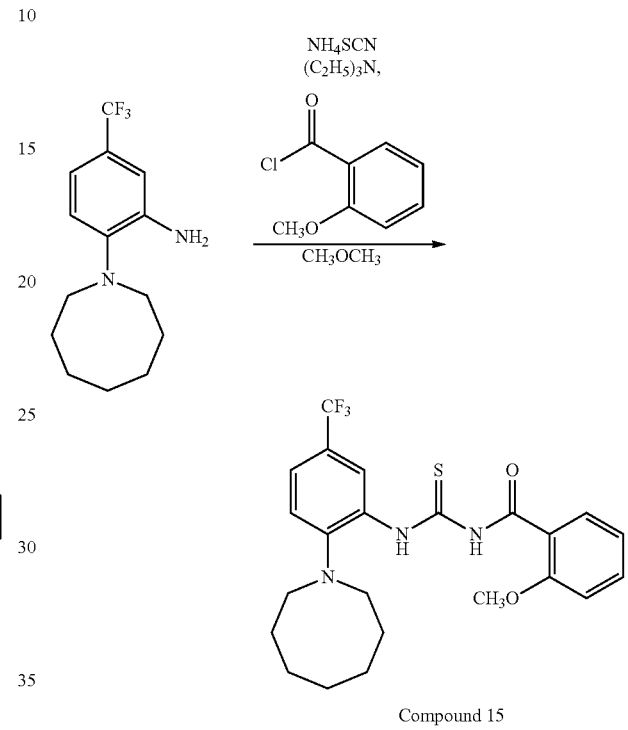

Compound 15

2-Methoxybenzoyl chloride (109 µL, 0.730 mmol) was added to an acetone solution (5 mL) of ammonium thiocyanate (55.6 mg, 0.730 mmol), followed by 1 hour of stirring at 60° C. The organic mixture was left to room temperature. 2-(Azacyclooctan-1-yl)-5-(trifluoromethyl)aniline (100 mg, 0.367 mmol) and triethylamine (102 µL, 0.730 mmol) were added sequentially. The reaction solution was stirred at room temperature overnight. Water was added to the solution. The mixture was subjected to extraction three times with ethyl acetate, washed with saturated sodium chloride solution, dried on anhydrous sodium sulfate, subjected to suction filtration, and then concentrated under reduced pressure. The residue was purified by silica gel column chromatography (hexane/ethyl acetate=5/1), so that N-(2-methoxybenzoyl)-N'-[2-(azacyclooctan-1-yl)-5-(trifluoromethyl)phenyl]thiourea (Compound 15) (51.5 mg, 30.1%) was obtained as colorless solid.

The results of the melting point, TLC, $^1$H NMR (CDCl$_3$, 400 MHz), and IR are as follows.

Melting point 30-31° C.; TLC $R_f$ 0.30 (hexane/ethyl acetate=5/1); $^1$H NMR (CDCl$_3$, 400 MHz) δ 1.64-1.75 (m, 10H, 5CH$_2$), 3.31-3.34 (m, 4H, 2CH$_2$), 4.11 (s, 3H, OCH$_3$), 7.07 (d, 1H, J=8.8 Hz, aromatic), 7.17 (d, 1H, J=8.5 Hz, aromatic), 7.17 (d, 1H, J=7.7 Hz, aromatic), 7.41 (dd, 1H, J=1.7, 8.8 Hz, aromatic), 7.61 (ddd, 1H, J=1.7, 7.7, 8.5 Hz, aromatic), 8.19 (d, 1H, J=1.7 Hz, aromatic), 8.22 (dd, 1H, J=1.7, 7.7 Hz, aromatic), 11.2 (s, 1H, NH), 12.4 (s, 1H, NH); IR (KBr, cm$^{-1}$) 600, 615, 648, 698, 756, 814, 858, 891, 964, 1018, 1084, 1117, 1163, 1248, 1290, 1331, 1395, 1512, 1578, 1603, 1614, 1663, 2849, 2924, 3136, 3316; Anal. Calcd for $C_{23}H_{26}F_3N_3O_2S$, C, 59.34; H, 5.63; N, 9.03. Found, C, 60.23; H, 5.93; N, 8.64.

Reference Example 16

Synthesis of Compound 16

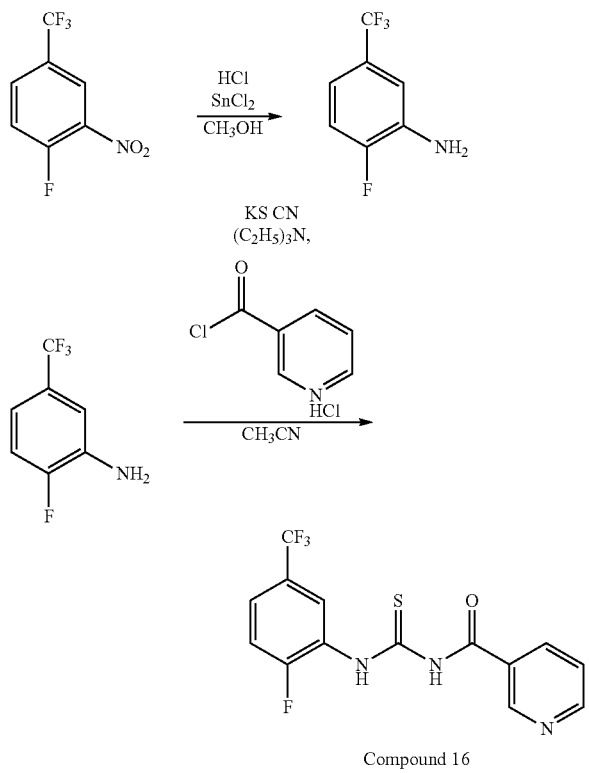

Compound 16

12 N HCl (3.89 mL, 46.6 mmol) and $SnCl_2$ (4.76 g, 25.1 mmol) were added sequentially at 0° C. to a methanol (5 mL) solution of 1-fluoro-2-nitro-4-(trifluoromethyl)benzene (1.50 g, 7.17 mmol). The mixture was left to room temperature and then stirred overnight. A saturated aqueous solution of sodium bicarbonate was added to the mixture, followed by suction filtration. The mixture was subjected to extraction three times with ethyl acetate. The thus extracted organic mixture was washed with saturated sodium chloride solution, dried on anhydrous sodium sulfate, subjected to suction filtration, and then concentrated under reduced pressure. The residue was purified by silica gel column chromatography (hexane/ethyl acetate=10/1), so that 2-fluoro-5-(trifluoromethyl)aniline (942 mg, 73.4%) was obtained as orange oil.

The results of TLC and $^1H$ NMR ($CDCl_3$, 400 MHz) are as follows. TLC $R_f$ 0.37 (hexane/ethyl acetate=10/1); $^1H$ NMR ($CDCl_3$, 400 MHz) δ 3.90 (s, 2H, $NH_2$), 6.96-7.26 (m, 3H, aromatic).

Nicotinoyl chloride hydrochloride (199 mg, 1.12 mmol) was added to an acetone solution (5 mL) of ammonium thiocyanate (85.3 mg, 1.12 mmol), followed by 1 hour of stirring at 60° C. The organic mixture was left to room temperature. 2-Fluoro-5-(trifluoromethyl)aniline (100 mg, 0.558 mmol) and triethylamine (155 μL, 1.12 mmol) were added sequentially. The reaction solution was stirred at room temperature overnight. Water was added. The mixture was subjected to extraction three times with ethyl acetate, washed with saturated sodium chloride solution, dried on anhydrous sodium sulfate, subjected to suction filtration, and then concentrated under reduced pressure. The residue was purified by silica gel column chromatography (hexane/ethyl acetate=2/1), so that N-nicotinoyl-N'-[2-fluoro-5-(trifluoro-methyl)phenyl]thiourea (Compound 16) (128 mg, 66.8%) was obtained as colorless solid.

The results of the melting point, TLC, $^1H$ NMR ($CDCl_3$, 400 MHz), and IR are as follows.

Melting point 163-165° C.; TLC $R_f$ 0.31 (hexane/ethyl acetate=2/1); $^1H$ NMR ($CDCl_3$, 400 MHz) δ 7.32 (t, 1H, J=9.2 Hz, aromatic), 7.51-7.57 (m, 3H, aromatic), 8.23 (ddd, 1H, J=1.7, 2.2, 8.1 Hz, aromatic), 8.92 (d, 1H, J=2.4 Hz, aromatic), 9.17 (d, 1H, J=2.4 Hz, aromatic), 9.20 (s, 1H, NH), 12.7 (s, 1H, NH); IR (KBr, $cm^{-1}$) 702, 729, 800, 887, 901, 1030, 1070, 1107, 1121, 1148, 2265, 1202, 1265, 1281, 1310, 1335, 1349, 1422, 1443, 1483, 1551, 1607, 1668, 3007, 3181.

Reference Example 17

Synthesis of Compound 17

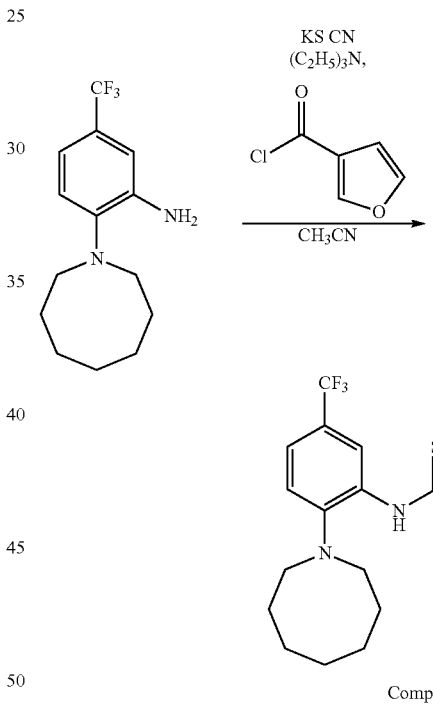

Compound 17

Thionyl chloride (130 μL, 1.78 mmol) was added to a dichloromethane solution (5 mL) of 3-furancarboxylic acid (100 mg, 0.892 mmol), followed by overnight stirring at 60° C. The organic mixture was left to room temperature and then concentrated under reduced pressure. The thus obtained residue was suspended in acetonitrile (5 mL) and then potassium thiocyanate (95.4 mg, 0.982 mmol) was added thereto, followed by 1 hour of stirring at 60° C. The organic mixture was left to room temperature and then 2-(azacyclooctan-1-yl)-5-(trifluoromethyl)aniline (100 mg, 0.367 mmol) was added to the solution. The reaction solution was stirred overnight at room temperature. Water was added. The thus obtained organic mixture was subjected to extraction three times with ethyl acetate, washed with saturated sodium chloride solution, dried on anhydrous sodium sulfate, filtered, and then concentrated under reduced pressure. The residue was purified by silica gel column chromatography (hexane/ethyl acetate=10/1), so that N-(3-franyl)-N'-[2-(azacyclooctan-1-yl)-5-(trifluoromethyl)phenyl]thiourea (Compound 17) (quant.) was obtained as yellow solid.

The results of the melting point, TLC, $^1$H NMR (CDCl$_3$, 400 MHz), and IR are as follows.

Melting point 42-45° C.; TLC R$_f$ 0.24 (hexane/ethyl acetate=10/1); $^1$H NMR (CDCl$_3$, 400 MHz) δ 1.73-1.74 (br s, 10H, 5CH$_2$), 3.29-3.32 (m, 4H, 2CH$_2$), 6.77 (d, 1H, J=1.2 Hz, aromatic), 7.18 (d, 1H, J=8.5 Hz, aromatic), 7.42 (dd, 1H, J=1.2, 8.5 Hz, aromatic), 7.55 (s, 1H, aromatic), 8.16 (s, 1H, aromatic), 8.18 (s, 1H, aromatic), 8.78 (s, 1H, NH), 12.1 (s, 1H, NH); $^{13}$C NMR (CDCl$_3$, 100 MHz) δ 25.2 (2C), 26.9, 27.3 (2C), 53.5 (2C), 108.1, 120.0, 120.7, 122.1 (q, J=33.6 Hz), 124.4 (d, J=4.1 Hz), 125.1 (d, J=4.1 Hz), 125.5, 129.1, 144.8, 147.1, 150.3, 161.7, 178.7; IR (KBr, cm$^{-1}$) 602, 698, 754, 818, 853, 874, 891, 970, 1018, 1082, 1117, 1163, 1207, 1263, 1331, 1395, 1454, 1526, 1570, 1616, 1674, 2853, 2926, 3138; MS (EI) m/z 425 (M$^+$); Anal. Calcd for C$_{20}$H$_{22}$F$_3$N$_3$O$_2$S, C, 56.46; H, 5.21; N, 9.88. Found, C, 56.12; H, 5.20; N, 9.72.

Reference Example 18

Synthesis of Compound 18 residue was purified by silica gel column chromatography (hexane/ethyl acetate=10/1), so that N-(thiofuran-3-yl)-N'-[2-(azacyclooctan-1-yl)-5-(trifluoromethyl)phenyl]thiourea (Compound 18) (157 mg, 96.9%) was obtained as yellow solid.

The results of the melting point, TLC, $^1$H NMR (CDCl$_3$, 400 MHz), and IR are as follows.

Melting point 134-137° C.; TLC R$_f$ 0.22 (hexane/ethyl acetate=10/1); $^1$H NMR (CDCl$_3$, 400 MHz) δ 1.66-1.75 (m, 10H, 5CH$_2$), 3.30-3.33 (m, 4H, 2CH$_2$), 7.19 (d, 1H, J=8.7 Hz, aromatic), 7.42 (dd, 1H, J=1.7, 8.7 Hz, aromatic), 7.47 (dd, 1H, J=2.9, 5.1 Hz, aromatic), 7.53 (dd, 1H, J=1.4, 5.1 Hz, aromatic), 8.15 (dd, 1H, J=1.4, 2.9 Hz, aromatic), 8.20 (d, 1H, J=1.7 Hz, aromatic), 8.98 (s, 1H, NH), 12.2 (s, 1H, NH); $^{13}$C NMR (CDCl$_3$, 100 MHz) δ 25.2 (2C), 26.9, 27.3 (2C), 53.5 (2C), 120.1, 122.2 (q, J=33.6 Hz), 124.4 (d, J=3.3 Hz), 125.0 (d, J=3.3 Hz), 125.5, 126.0, 127.8, 129.2, 131.8, 134.5, 150.3, 161.6, 178.8; IR (KBr, cm$^{-1}$) 745, 814, 1082, 1117, 1146, 1165, 1209, 1263, 1333, 1396, 1412, 1523, 1616, 1668, 2851, 2926, 3111; MS (EI) m/z 441 (M$^+$).

Reference Example 19

Synthesis of Compound 19

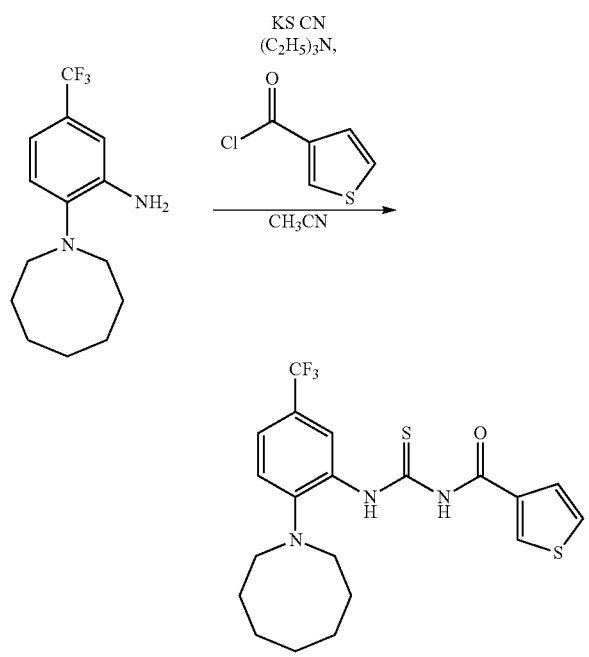

Compound 18

3-Thiophenecarbonyl chloride (135 mg, 0.920 mmol) was added to a dichloromethane solution (5 mL) of potassium thiocyanate (98.2 mg, 1.01 mmol), followed by overnight stirring at 60° C. The organic mixture was left to room temperature. 2-(Azacyclooctan-1-yl)-5-(trifluoromethyl)aniline (100 mg, 0.367 mmol) was added. The reaction solution was stirred at room temperature overnight. Water was added. The mixture was subjected to extraction three times with ethyl acetate, washed with saturated sodium chloride solution, dried on anhydrous sodium sulfate, subjected to suction filtration, and then concentrated under reduced pressure. The

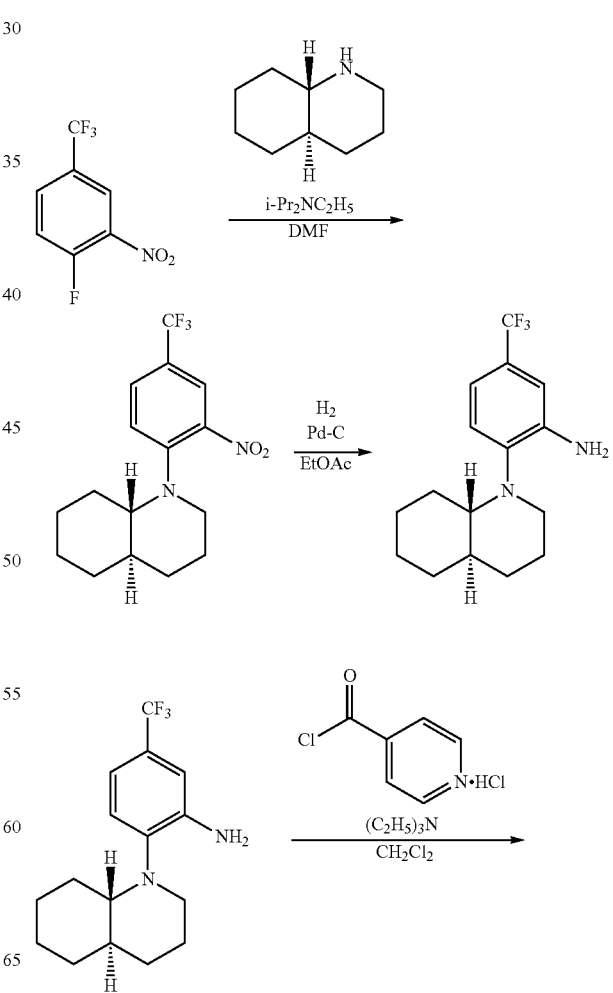

-continued

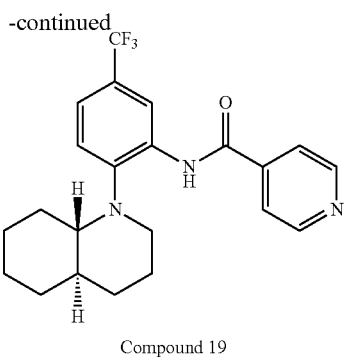

Compound 19

Trans-decahydroquinoline (1.84 g, 13.2 mmol; commercial product) and N,N-diisopropylethylamine (2.51 mL, 14.4 mmol) were added sequentially at room temperature to a N,N-dimethylformamide (DMF) (6.0 mL) solution of 1-fluoro-2-nitro-4-(trifluoromethyl)benzene (2.50 g, 12.0 mmol; commercial product). The mixture was stirred at room temperature for 19 hours. The mixture was poured into water. The mixture was subjected to extraction with ether (×3). The thus extracted organic layer was washed with water (×3) and then with brine (×1), dried on $Na_2SO_4$, filtered, and then concentrated under reduced pressure.

The residue was purified by silica gel column chromatography (220 g, hexane/diethyl ether=50/1), so that 4-(trans-2-azabicyclo[4.4.0]decan-2-yl)-3-nitro-benzotrifluoride (3.57 g, 10.9 mmol, 91.8%) was obtained as orange oil.

The results of TLC, $^1$H NMR ($CDCl_3$, 300 MHz), and IR are as follows. TLC $R_f$ 0.71 (hexane/ethyl acetate=9/1); $^1$H NMR ($CDCl_3$, 300 MHz) δ 0.85-1.53 (m, 7H, $3CH_2$, CH), 1.58-1.88 (m, 6H, $3CH_2$), 2.50 (ddd, 1H, J=3.3, 9.0, 11.1 Hz, CH), 2.63 (ddd, 1H, J=3.0, 11.1, 11.1 Hz, CH), 3.12-3.26 (m, 1H, CH), 7.49 (d, 1H, J=8.4 Hz, aromatic), 7.73 (dd, 1H, J=2.0, 8.4 Hz, aromatic), 7.82 (d, 1H, J=2.0 Hz, aromatic); IR (KBr, $cm^{-1}$) 687, 800, 831, 844, 881, 899, 995, 1074, 1096, 1134, 1175, 1229, 1256, 1265, 1285, 1325, 1368, 1449, 1541, 1622, 2805, 2857, 2930.

In argon atmosphere, palladium-carbon (10% Pd) (palladium/charcoal activated (10% Pd)) (100 mg; commercial product) was added at room temperature to an ethyl acetate (25 mL) solution of 4-(trans-2-azabicyclo[4.4.0]decan-2-yl)-3-nitrobenzo-trifluoride (2.94 g, 8.95 mmol). In hydrogen atmosphere, the solution was stirred at room temperature for 10 hours. After substitution with argon, dichloromethane (60 mL) was added to the solution. After 30 minutes of stirring at room temperature, palladium-carbon was removed by filtration, and then the resultant was concentrated under reduced pressure.

The residue was purified by silica gel column chromatography (110 g, hexane/diethyl ether=50/1), so that 2-(trans-2-azabicyclo[4.4.0]decan-2-yl)-5-(trifluoro-methyl)aniline (2.63 g, 8.82 mmol, 98.4%) was obtained as colorless solid.

The results of TLC, $^1$H NMR ($CDCl_3$, 300 MHz), and IR are as follows. TLC $R_f$ 0.50 (hexane/ethyl acetate=9/1); $^1$H NMR ($CDCl_3$, 300 MHz) δ 0.80-0.98 (m, 1H, CH), 1.02-1.42 (m, 5H, $2CH_2$, CH), 1.56-1.77 (m, 7H, $3CH_2$, CH), 2.41 (ddd, 1H, J=2.9, 8.4, 11.3 Hz, CH), 2.47-2.56 (m, 1H, CH), 2.84-2.95 (m, 1H, CH), 4.30-4.40 (br s, 2H, $NH_2$), 6.91-6.97 (m, 2H, aromatic), 7.10 (d, 1H, J=8.7 Hz, aromatic); IR (KBr, $cm^{-1}$) 471, 498, 652, 667, 743, 814, 866, 883, 932, 995, 1059, 1088, 1121, 1163, 1217, 1242, 1285, 1335, 1375, 1441, 1512, 1566, 1593, 1614, 2801, 2855, 2924, 3368, 3474.

Triethylamine (605 μL, 4.34 mmol) and isonicotinoyl chloride hydrochloride (commercial product) (385 mg, 2.16 mmol) were added sequentially at 0° C. to a dichloromethane (9 mL) solution of 2-(trans-2-azabicyclo[4.4.0]decan-2-yl)-5-(trifluoromethyl)aniline (430 mg, 1.44 mmol). The mixture was left to room temperature and then stirred for 23 hours. The mixture was then poured into water. The mixture was subjected to extraction with dichloromethane (×3). The thus extracted organic layer was washed with water (×1), dried on $Na_2SO_4$, filtered, and then concentrated under reduced pressure.

The residue was purified by silica gel column chromatography (50 g, hexane/ethyl acetate=4/1), so that N-[2-(trans-2-azabicyclo[4.4.0]decan-2-yl)-5-(trifluoromethyl)phenyl] isonicotinamide (Compound 19) (574 mg, 1.42 mmol, 98.7%) was obtained as colorless solid.

The results of the melting point, TLC, $^1$H NMR ($CDCl_3$, 300 MHz), and IR are as follows.

Melting point 128-131° C.; TLC $R_f$ 0.44 (hexane/ethyl acetate=2/1); $^1$H NMR ($CDCl_3$, 300 MHz) δ 0.78-0.96 (m, 1H, CH), 1.06-1.55 (m, 6H, $3CH_2$), 1.56-1.78 (m, 4H, $2CH_2$), 1.78-1.96 (m, 2H, $CH_2$), 2.51 (ddd, 1H, J=3.5, 8.9, 11.8 Hz, CH), 2.73 (ddd, 1H, J=2.6, 11.8, 11.8 Hz, CH), 2.83-2.94 (m, 1H, CH), 7.36 (d, 1H, J=8.3 Hz, aromatic), 7.40 (dd, 1H, J=1.9, 8.3 Hz, aromatic), 7.73-7.80 (AA'BB', 2H, aromatic), 8.85-8.89 (AA'BB', 2H, aromatic), 8.93 (d, 1H, J=1.9 Hz, aromatic), 10.2-10.3 (br s, 1H, NH); IR (KBr, $cm^{-1}$) 509, 586, 602, 652, 685, 733, 839, 901, 918, 930, 995, 1070, 1101, 1123, 1165, 1242, 1333, 1366, 1408, 1443, 1528, 1591, 1612, 1682, 2855, 2928, 3292.

Reference Example 20

Synthesis of Compound 20

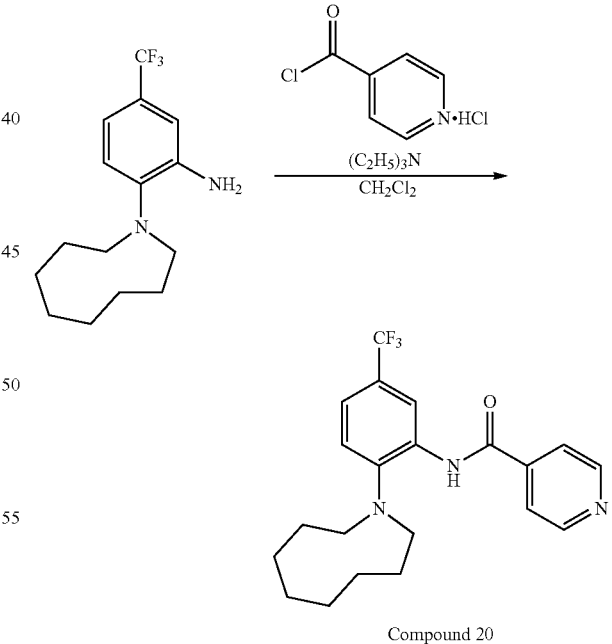

Compound 20

Triethylamine (560 μL, 4.02 mmol) and isonicotinoyl chloride hydrochloride (commercial product) (356 mg, 2.00 mmol) were added sequentially at 0° C. to a dichloromethane (7 mL) solution of 2-(azacyclononan-1-yl)-5-(trifluoromethyl)aniline (381 mg, 1.33 mmol). The mixture was left to room temperature and then stirred for 14 hours. The mixture was poured into water and then subjected to extraction with dichloromethane (×3). The thus extracted organic layer was washed with water (×1), dried on Na$_2$SO$_4$, filtered, and then concentrated under reduced pressure.

The residue was purified by silica gel column chromatography (30 g, hexane/ethyl acetate=2/1), so that W[2-(azacyclononan-1-yl)-5-(trifluoromethyl)-phenyl]isonicotinamide (Compound 20) (392 mg, 1.00 mmol, 75.3%) was obtained as colorless solid.

The results of the melting point, TLC, $^1$H NMR (CDCl$_3$, 300 MHz), and IR are as follows.

Melting point 113-115° C.; TLC R$_f$ 0.27 (hexane/ethyl acetate=2/1); $^1$H NMR (CDCl$_3$, 300 MHz) δ 1.53-1.70 (br s, 12H, 6CH$_2$), 2.99-3.08 (br s, 4H, 2CH$_2$), 7.40 (dd, 1H, J=1.2, 8.8 Hz, aromatic), 7.45 (dd, 1H, J=8.8 Hz, aromatic), 7.71-7.76 (AA'BB', 2H, aromatic), 8.79-8.86 (m, 3H, aromatic), 9.50-9.60 (br s, 1H, NH); IR (KBr, cm$^{-1}$) 664, 677, 694, 735, 754, 833, 903, 920, 1123, 1163, 1242, 1333, 1408, 1437, 1462, 1526, 1555, 1587, 1614, 1682, 2849, 2928, 3323.

Melting point 147-148° C.; TLC R$_f$ 0.36 (hexane/dichloromethane/ethyl acetate=3/3/1); $^1$H NMR (CDCl$_3$, 300 MHz) δ 0.74-0.92 (m, 1H, CH), 1.06-1.40 (m, 5H, 2CH$_2$, CH), 1.42-1.54 (m, 1H, CH), 1.56-1.75 (m, 4H, 2CH$_2$), 1.75-1.90 (m, 2H, CH$_2$), 2.47-2.59 (m, 1H, CH), 2.75 (ddd, 1H, J=2.4, 12.0, 12.0 Hz, CH), 2.83-2.93 (m, 1H, CH), 7.43 (d, 1H, J=8.2 Hz, aromatic), 7.53 (d, 1H, J=8.2 Hz, aromatic), 7.68-7.80 (AA'BB', 2H, aromatic), 8.73-8.83 (AA'BB', 2H, aromatic), 9.96 (s, 1H, aromatic), 11.5-11.7 (br s, 1H, NH); IR (KBr, cm$^{-1}$) 650, 733, 760, 826, 895, 995, 1013, 1070, 1125, 1167, 1229, 1273, 1285, 1333, 1366, 1408, 1449, 1526, 1589, 2855, 2928, 3171.

Reference Example 22

Synthesis of Compound 22

Reference Example 21

Synthesis of Compound 21

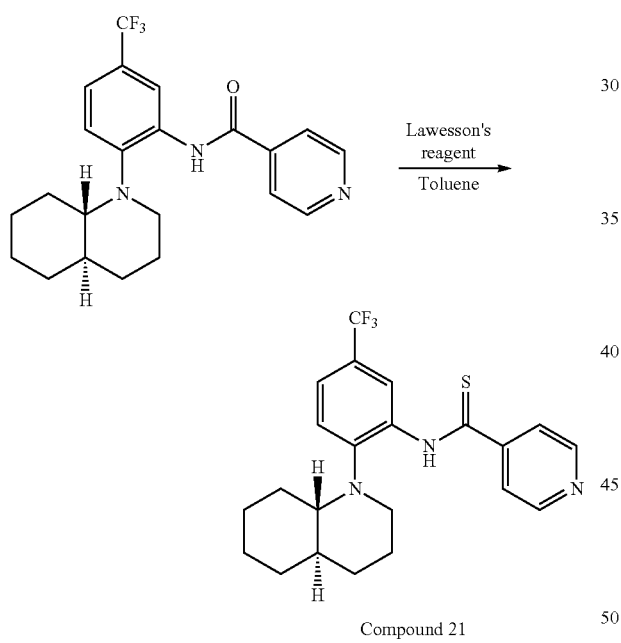

Compound 21

Lawesson's reagent (82.9 mg, 205 μmol; commercial product) was added at room temperature to a toluene (5 mL) solution of N-[2-(trans-2-azabicyclo[4.4.0]decan-2-yl)-5-(trifluoromethyl)phenyl]isonicotinamide (138 mg, 342 μmol obtained in [Reference example 19]. The mixture was stirred at 120° C. for 7 hours. After stirring, the mixture was left to room temperature and then concentrated under reduced pressure.

The residue was purified by silica gel column chromatography (8 g, hexane/dichloromethane/ethyl acetate=4/3/1), so that N-[2-(trans-2-azabicyclo[4.4.0]-decan-2-yl)-5-(trifluoromethyl)phenyl]isonicotinthioamide (Compound 21) (85.3 mg, 203 μmol, 59.4%) was obtained as yellow solid.

The results for the melting point, TLC, $^1$H NMR (CDCl$_3$, 300 MHz), and IR are as follows.

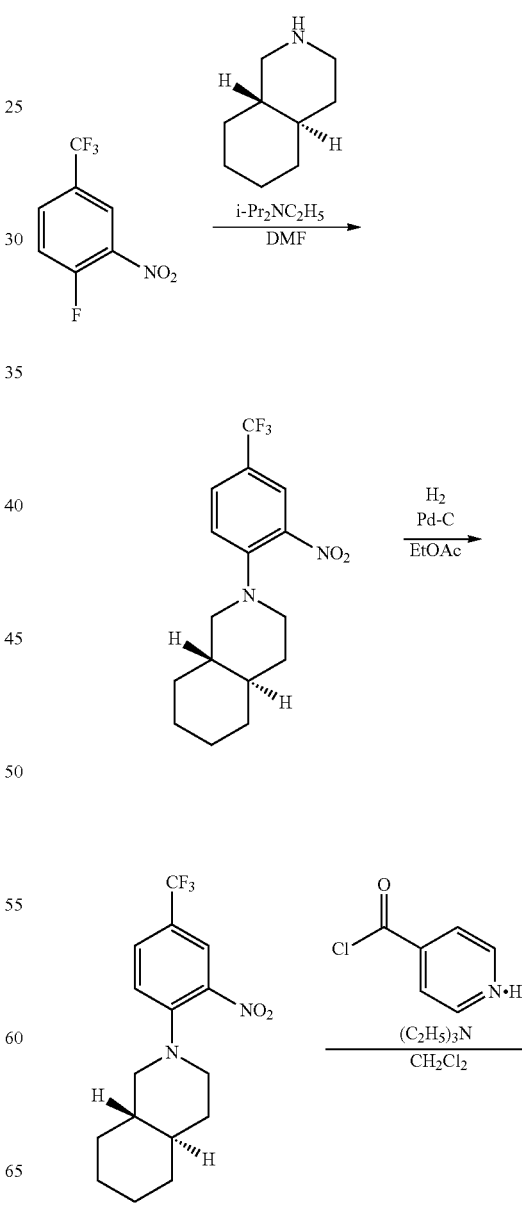

-continued

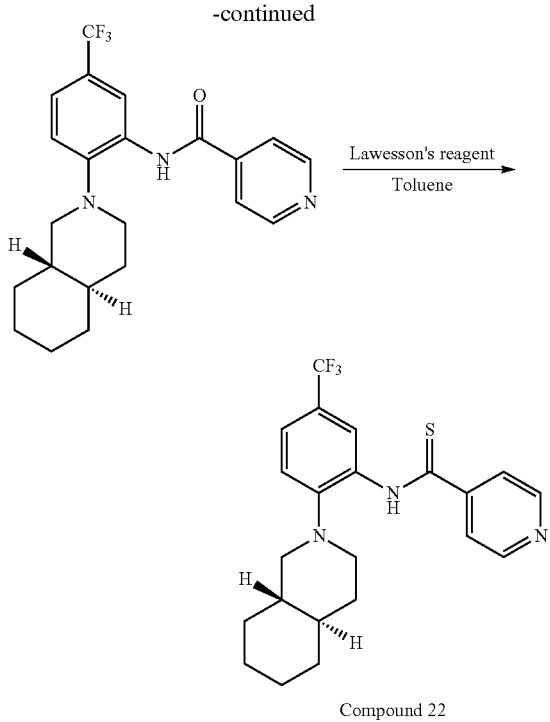

Compound 22

Trans-decahydroisoquinoline (1.58 mL, 10.6 mmol; commercial product) and N,N-diisopropylethylamine (2.00 mL, 11.5 mmol) were added sequentially at room temperature to a N,N-dimethylformamide (DMF) (5.0 mL) solution of 1-fluoro-2-nitro-4-(trifluoromethyl)benzene (2.00 g, 9.56 mmol; commercial product). The mixture was stirred at room temperature for 24 hours. The mixture was poured into water and then the mixture was subjected to extraction with ether (×3). The thus extracted organic layer was washed with water (×3) and then with brine (×1), dried on $Na_2SO_4$, filtered, and then concentrated under reduced pressure.

The residue was purified by silica gel column chromatography (50 g, hexane/diethyl ether=50/1), so that 4-(trans-3-azabicyclo[4.4.0]decan-3-yl)-3-nitrobenzotrifluoride (3.06 g, 9.32 mmol, 97.4%) was obtained as orange oil.

The results of TLC, $^1$H NMR ($CDCl_3$, 300 MHz), and IR are as follows. TLC $R_f$ 0.56 (hexane/ethyl acetate=9/1); $^1$H NMR ($CDCl_3$, 300 MHz) δ 0.90-1.18 (m, 3H, $CH_2$, CH), 1.18-1.63 (m, 6H, $3CH_2$), 1.63-1.72 (m, 1H, CH), 1.72-1.84 (m, 2H, $CH_2$), 2.64 (dd, 1H, J=11.3, 12.3 Hz, CH), 3.00 (ddd, 1H, J=2.8, 12.6, 12.6 Hz, CH), 3.14 (ddd, 1H, J=2.4, 3.7, 12.3 Hz, CH), 3.35 (dddd, 1H, J=2.4, 2.4, 4.5, 12.6 Hz, CH), 7.13 (d, 1H, J=8.8 Hz, aromatic), 7.60 (dd, 1H, J=1.7, 8.8 Hz, aromatic), 8.04 (d, 1H, J=1.7 Hz, aromatic); IR (KBr, cm$^{-1}$) 642, 683, 791, 824, 885, 907, 972, 1086, 1123, 1159, 1177, 1206, 1217, 1242, 1263, 1300, 1325, 1391, 1447, 1508, 1533, 1560, 1624, 2851, 2922, 3447.

In argon atmosphere, palladium-carbon (10% Pd) (palladium/charcoal activated (10% Pd)) (100 mg; commercial product) was added at room temperature to an ethyl acetate (17 mL) solution of 4-(trans-3-azabicyclo[4.4.0]decan-3-yl)-3-nitrobenzo-trifluoride (2.93 g, 8.92 mmol). In hydrogen atmosphere, the solution was stirred at room temperature for 22.5 hours. After substitution with argon, dichloromethane (200 mL) was added to the resultant. After 30 minutes of stirring at room temperature, palladium-carbon was removed by filtration, and then the resultant was concentrated under reduced pressure.

The residue was purified by silica gel column chromatography (100 g, hexane/diethyl ether=50/1), so that 2-(trans-3-azabicyclo[4.4.0]decan-3-yl)-5-(trifluoro-methyl)aniline (2.58 g, 8.65 mmol, 96.9%) was obtained as colorless solid.

The results of TLC, $^1$H NMR ($CDCl_3$, 300 MHz), and IR are as follows. TLC $R_f$ 0.50 (hexane/ethyl acetate=9/1); $^1$H NMR ($CDCl_3$, 300 MHz) δ 0.93-1.15 (m, 3H, $CH_2$, CH), 1.20-1.50 (m, 4H, $2CH_2$), 1.53-1.63 (m, 1H, CH), 1.63-1.84 (m, 4H, $2CH_2$), 2.28 (dd, 1H, J=11.2, 11.2 Hz, CH), 2.61 (ddd, 1H, J=2.5, 11.9, 11.9 Hz, CH), 3.01 (ddd, 1H, J=2.1, 3.5, 11.2 Hz, CH), 3.17 (dddd, 1H, J=2.1, 2.1, 4.1, 11.9 Hz, CH), 3.98-4.12 (br s, 2H, $NH_2$), 6.92 (d, 1H, J=1.8 Hz, aromatic), 6.96 (d, 1H, J=1.8, 8.2 Hz, aromatic), 7.01 (d, 1H, J=7.0 Hz, aromatic); IR (KBr, cm$^{-1}$) 656, 669, 741, 818, 874, 895, 935, 972, 1121, 1152, 1169, 1200, 1217, 1236, 1254, 1294, 1335, 1381, 1439, 1460, 1514, 1568, 1593, 1612, 2783, 2851, 2920, 3331, 3428.

Triethylamine (1.10 mL, 7.89 mmol) and isonicotinoyl chloride hydrochloride (2.10 g, 11.8 mmol; commercial product) were added sequentially at 0° C. to a dichloromethane (14 mL) solution of 2-(trans-3-azabicyclo[4.4.0]decan-3-yl)-5-(trifluoromethyl)aniline (784 mg, 2.63 mmol). The mixture was left to room temperature and then stirred for 20 hours. The mixture was poured into water and then subjected to extraction with dichloromethane (×3). The thus extracted organic layer was washed with water (×1), dried on $Na_2SO_4$, filtered, and then concentrated under reduced pressure.

The residue was purified by silica gel column chromatography (50 g, hexane/ethyl acetate=7/2), so that N-[2-(trans-3-azabicyclo[4.4.0]decan-3-yl)-5-(trifluoromethyl)phenyl] isonicotinamide (574 mg, 1.42 mmol, 98.7%) was obtained as a colorless solid.

The results of TLC, $^1$H NMR ($CDCl_3$, 300 MHz), and IR are as follows. TLC $R_f$ 0.27 (hexane/ethyl acetate=3/1); $^1$H NMR ($CDCl_3$, 300 MHz) δ 0.98-1.22 (m, 3H, $CH_2$, CH), 1.28-1.50 (m, 4H, $2CH_2$), 1.52-1.62 (m, 1H, CH), 1.70-1.86 (m, 4H, $2CH_2$), 2.50 (dd, 1H, J=11.1, 11.1 Hz, CH), 2.77 (ddd, 1H, J=2.2, 11.8, 11.8 Hz, CH), 2.89 (ddd, 1H, J=1.9, 3.5, 11.1 Hz, CH), 3.04 (dddd, 1H, J=1.8, 1.8, 3.9, 11.8 Hz, CH), 7.29 (d, 1H, J=8.2 Hz, aromatic), 7.39 (dd, 1H, J=1.4, 8.2 Hz, aromatic), 7.73-7.78 (AA'BB', 2H, aromatic), 8.84-8.89 (m, 3H, aromatic), 9.45-9.55 (br s, 1H, NH); IR (KBr, cm$^1$) 658, 687, 735, 750, 837, 881, 899, 918, 930, 970, 1072, 1101, 1123, 1167, 1219, 1246, 1333, 1381, 1408, 1441, 1530, 1587, 1614, 1682, 2853, 2922, 3321.

Lawesson's reagent (158 mg, 391 μmol; commercial product) was added at room temperature to a toluene (10.0 mL) solution of N-[2-(trans-3-azabicyclo[4.4.0]decan-3-yl)-5-(trifluoromethyl)phenyl]isonicotinamide (261 mg, 647 mmol). The mixture was stirred at 120° C. for 14 hours. After stirring, the mixture was left to room temperature and then concentrated under reduced pressure.

The residue was purified by silica gel column chromatography (30 g, hexane/dichloromethane/ethyl acetate=4/3/1), so that N-[2-(trans-3-azabicyclo[4.4.0]decan-3-yl)-5-(trifluoromethyl)phenyl]isonicotinthioamide (Compound 22) (173 mg, 412 μmol, 63.7%) was obtained as yellow solid.

The results of the melting point, TLC, $^1$H NMR ($CDCl_3$, 300 MHz), and IR are as follows.

Melting point 128-129° C.; TLC $R_f$ 0.53 (hexane/dichloromethane/ethyl acetate=3/5/2); $^1$H NMR ($CDCl_3$, 300 MHz) δ 0.94-1.14 (m, 2H, $CH_2$), 1.16-1.38 (m, 4H, $2CH_2$), 1.47-1.57 (m, 1H, CH), 1.65-1.84 (m, 5H, $2CH_2$, CH), 2.50 (dd, 1H, J=11.1, 11.1 Hz, CH), 2.79 (ddd, 1H, J=2.5, 12.1, 12.1 Hz, CH), 2.81-2.91 (m, 1H, CH), 2.96-3.08 (m, 1H, CH), 7.32 (d, 1H, J=8.0 Hz, aromatic), 7.51 (d, 1H, J=8.0 Hz, aromatic), 7.65-7.80 (AA'BB', 2H, aromatic), 8.70-8.85 (AA'BB', 2H, aromatic), 9.58 (s, 1H, aromatic), 10.4-10.6 (br s, 1H, NH); IR (KBr, cm$^{-1}$) 652, 733, 826, 891, 970, 1011, 1076, 1123, 1167, 1217, 1238, 1275, 1333, 1410, 1437, 1458, 1528, 1591, 1616, 2853, 2922, 3171.

Reference Example 23

Synthesis of Compound 23

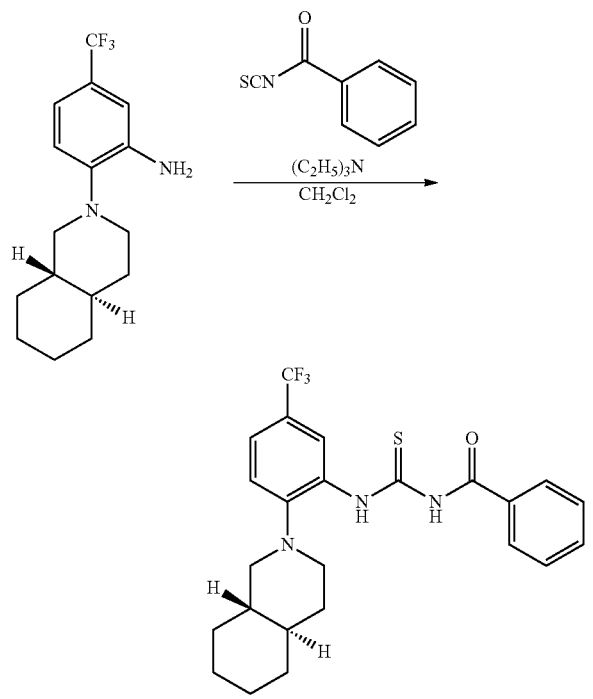

Compound 23

In argon atmosphere, triethylamine (280 μL, 2.01 mmol) and benzoyl isothiocyanate (165 μL, 1.23 mmol; commercial product) were added sequentially at room temperature to a dichloromethane (5 mL) solution of 2-(trans-3-azabicyclo[4.4.0]decan-3-yl)-5-(trifluoromethyl)aniline (2.99 mg, 1.00 mmol). The mixture was stirred at 50° C. for 3 hours. After stirring, the mixture was left to room temperature and then poured into water. The mixture was subjected to extraction with dichloromethane (×3). The thus extracted organic layer was washed with water (×1), dried on Na$_2$SO$_4$, filtered, and then concentrated under reduced pressure.

The residue was purified by silica gel column chromatography (30 g, hexane/ethyl acetate=15/1), so that 1-benzoyl-3-[2-(trans-3-azabicyclo[4.4.0]decan-3-yl)-5-(trifluoromethyl)phenyl]thiourea (Compound 23) (158 mg, 342 μmol, 34.2%) was obtained as colorless solid.

The results of the melting point, TLC, $^1$H NMR (CDCl$_3$, 300 MHz), and IR are as follows.

Melting point 147-149° C.; TLC R$_f$ 0.31 (hexane/ethyl acetate=9/1); $^1$H NMR (CDCl$_3$, 300 MHz) δ 0.92-1.21 (br s, 3H, CH$_2$, CH), 1.22-1.40 (m, 2H, CH$_2$), 1.50-1.82 (m, 7H, 3CH$_2$, CH), 2.47 (dd, 1H, J=10.9, 10.9 Hz, CH), 2.69 (ddd, 1H, J=3.5, 11.2, 11.2 Hz, CH), 2.95 (ddd, 1H, J=2.0, 3.3, 10.9 Hz, CH), 3.08-3.17 (m, 1H, CH), 7.21 (d, 1H, J=8.3 Hz, aromatic), 7.44 (dd, 1H, J=2.1, 8.3 Hz, aromatic), 7.53-7.62 (m, 2H, aromatic), 7.63-7.72 (m, 1H, aromatic), 7.89-7.95 (m, 2H, aromatic), 9.00-9.15 (br s, 2H, aromatic, NH), 12.9-13.0 (br s, 1H, NH); IR (KBr, cm$^{-1}$) 646, 662, 689, 706, 735, 826, 881, 893, 910, 970, 1076, 1121, 1152, 1213, 1254, 1298, 1333, 1381, 1447, 1487, 1516, 1535, 1580, 1616, 1676, 2814, 2849, 2922, 3084.

Reference Example 24

Synthesis of Compound 24

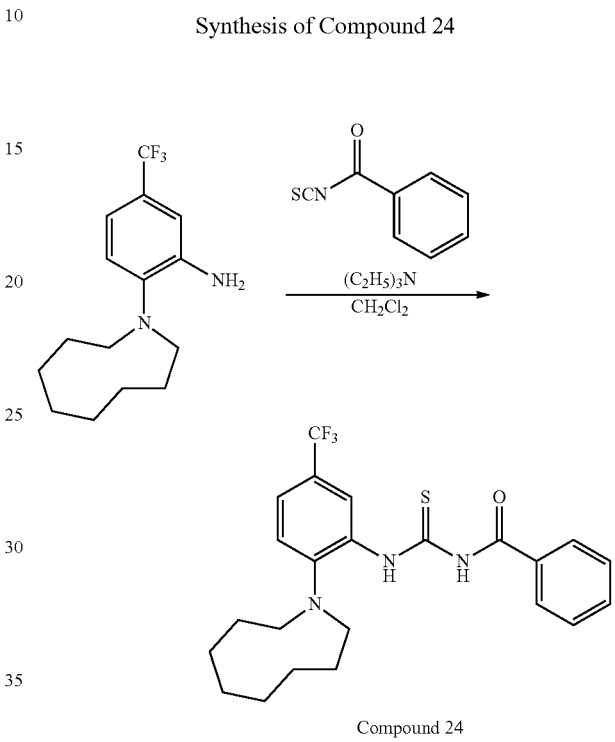

Compound 24

In argon atmosphere, triethylamine (280 μL, 2.01 mmol) and benzoyl isothiocyanate (165 μL, 1.23 mmol; commercial product) were added sequentially at room temperature to a dichloromethane (5 mL) solution of 2-(azacyclononan-1-yl)-5-(trifluoromethyl)aniline (287 mg, 1.00 mmol). The mixture was stirred at 50° C. for 3 hours. After stirring, the mixture was left to room temperature and then poured into water. The mixture was subjected to extraction with dichloromethane (×3). The thus extracted organic layer was washed with water (×1), dried on Na$_2$SO$_4$, filtered, and then concentrated under reduced pressure.

The residue was purified by silica gel column chromatography (30 g, hexane/ethyl acetate=10/1), so that 1-benzoyl-3-[2-(azacyclononan-1-yl)-5-(trifluoro-methyl)phenyl]thiourea (Compound 24) (88.7 mg, 197 μmol, 19.7%) was obtained as colorless solid.

The results of the melting point, TLC, $^1$H NMR (CDCl$_3$, 300 MHz), and IR are as follows.

Melting point 65-67° C.; TLC R$_f$ 0.19 (hexane/ethyl acetate=9/1); $^1$H NMR (CDCl$_3$, 300 MHz) δ 1.20-1.35 (br s, 4H, 2CH$_2$), 1.51-1.75 (br s, 8H, 4CH$_2$), 3.22-3.40 (br s, 4H, 2CH$_2$), 7.20 (d, 1H, J=8.7 Hz, aromatic), 7.45 (dd, 1H, J=2.0, 8.7 Hz, aromatic), 7.52-7.61 (m, 2H, aromatic), 7.63-7.72 (m, 1H, aromatic), 7.87-7.98 (m, 3H, aromatic), 9.05-9.25 (br s, 1H, NH), 12.0-12.2 (br s, 1H, NH); IR (KBr, cm$^{-1}$) 604, 654, 733, 814, 908, 1084, 1117, 1155, 1267, 1333, 1395, 1449, 1518, 1616, 1672, 2851, 2922, 3150.

Example 1A

Screening for Compound Having Anti-HCV Activity Using LuHCV Cells

As an HCV viral protein expression assay, screening was performed for compounds having anti-HCV activity using human hepatocytes with which the replication and expression of the intracellular HCV protein (NS3-NS4-NS5A-NS5B) can be evaluated through determination of luciferase activity (hereinafter, referred to as LuHCV).

LuHCV cells were plated onto 96-well plates at $5 \times 10^3$ cells/50 μL/well and then incubated overnight. Test compounds were each dissolved in dimethyl sulfoxide (DMSO) and dilution series were prepared using DMSO, if necessary. On the next day of plating of LuHCV cells, a medium containing a test compound with a concentration twice the final test concentration was added at 50 μL/well. Cells were gently cultured under culture conditions of 48 hours, 37° C., and 5% $CO_2$ (the final concentrations of the test compounds: 0, 10, and 20 μM). At this time, analysis was made using 3 test wells for each test compound and for each concentration.

Culture medium was removed after 48 hours. Glo lysis buffer (100 μL) (Promega) was added to each well and then cells were disrupted, so that a cell extract was obtained. With the use of 50 μL of the thus obtained cell extract, 50 μL of a Bright-Glo™ Luciferase Assay System (Promega) reagent was added. Luciferase activity in the extract was determined by measuring luminescence intensity for one second using a measuring device ARVO (PerkinElmer Co., Ltd.).

Based on the thus obtained numerical values of luminescence intensity, an average value for each test compound at each concentration was calculated. The luminescence intensity percentage for each test compound was calculated based on a luminescence intensity for DMSO (used as a control for test substances) as 100%. FIG. 1A shows the luminescence intensity percentage for each test compound.

Decreases in luciferase activity were observed in the presence of the test compounds in a concentration-dependent manner (Compound 2, Compound 5, and Compound 6). Furthermore, in the presence of 20 μM test compound, a significant decrease in luciferase activity compared with that of the control (DMSO) was observed. In particular, for Compound 5 and Compound 6, in the presence of even 10 μM of the compound, a decrease of about 50% in luminescence intensity was observed compared with the control.

These results demonstrated that the compounds tested herein effectively suppressed the expression of the HCV protein.

Example 1B

Evaluation of Cell Growth Suppression by Test Compound Using LuHCV Cell

LuHCV cells were plated onto 96-well plates at $5 \times 10^3$ cells/50 μL/well and then incubated overnight. Test compounds were each dissolved in dimethyl sulfoxide (DMSO) and dilution series were prepared using DMSO, if necessary. On the next day of plating of LuHCV cells, a medium containing a test compound with a concentration twice the final test concentration was added at 50 μL/well. Cells were gently cultured under culture conditions of 48 hours, 37° C., and 5% $CO_2$ (the final concentrations of the test compounds: 0, 10, and 20 μM). At this time, analysis was made using 3 test wells for each test compound and for each concentration.

After 48 hours, for measurement of the percentages of viable cells, a reagent SF for determination of the number of viable cells (NACALAI TESQUE, INC.) was added at 10 μL/well, cells were gently cultured under culture conditions of 37° C. and 5% $CO_2$, and then a coloring reaction was performed. Subsequently, absorbance was measured at 450 nm using a measuring device ARVO (PerkinElmer Co., Ltd.).

At this time, as a background absorbance, measurement was also performed for wells containing test compounds (or DMSO used as a control), but containing no cells. Each of the thus obtained background numerical values was deducted from the absorbance of a cell-containing well (measured for the same compound at the same concentration). The resulting value was designated as actual measurement of number of viable cells containing no background. Based on the thus obtained actual numbers of viable cells, an average value for each test compound at each concentration was calculated. With an average value measured for DMSO used as a control test substance designated as 100%, the percentage of the number of viable cells for each test compound was calculated. FIG. 1B shows the percentages of the number of viable cells (cell viability (% control)) calculated upon addition of test compounds.

As a result, as shown in FIG. 1B, the percentages of the number of viable cells never changed with the addition of any test compound. This indicates that these compounds do not change the percentages of viable cells under the conditions of Example 1A. Specifically, the results obtained in Example 1A suggest that the test compounds purely suppressed the expression of the HCV protein.

Example 2A

Screening for Compound with Structural Development Having Anti-HCV Activity Using LuHCV Cell LuHCV cells were plated onto 96-well plates at $5 \times 10^3$ cells/50 μL/well and then incubated overnight. Test compounds were each dissolved in dimethyl sulfoxide (DMSO) and dilution series were prepared using DMSO, if necessary. On the next day of plating of LuHCV cells, a medium containing a test compound with a concentration twice the final test concentration was added at 50 μL/well. Cells were gently cultured under culture conditions of 48 hours, 37° C., and 5% $CO_2$ (the final concentrations of the test compounds: 0, 10, and 20 μM). At this time, analysis was made using 3 test wells for each test compound and for each concentration.

Culture medium was removed after 48 hours. Glo Lysis buffer (100 μL) (Promega) was added to each well and then cells were disrupted, so that a cell extract was obtained. With the use of 50 μL of the thus obtained cell extract, 50 μL of a Bright-Glo™ Luciferase Assay System (Promega) reagent was added. Luciferase activity in the extract was determined by measuring luminescence intensity for one second using a measuring device ARVO (PerkinElmer Co., Ltd.).

Based on the thus obtained numerical values of luminescence intensity, an average value for each test compound at each concentration was calculated. The luminescence intensity percentage for each test compound was calculated based on a luminescence intensity of DMSO (used as a control for test substances) as 100%. Table 1-1 and FIG. 2A shows the luminescence intensity percentage for each test compound.

As in the results, decreases in luciferase activity were observed in a concentration-dependent manner for all compounds tested. This indicates that these compounds have activity of suppressing the intracellular expression of the HCV protein in a concentration-dependent manner.

Example 2B

Evaluation of Cell Growth Suppression by Compound with Structural Development Using LuHCV Cell LuHCV cells were plated onto 96-well plates at $5\times10^3$ cells/50 µL/well and then incubated overnight. Test compounds were each dissolved in dimethyl sulfoxide (DMSO) and dilution series were prepared using DMSO, if necessary. On the next day of plating of LuHCV cells, a medium containing a test compound with a concentration twice the final test concentration was added at 50 µL/well. Cells were gently cultured under culture conditions of 48 hours, 37° C., and 5% $CO_2$ (the final concentrations of the test compounds: 0, 10, and 20 µM). At this time, analysis was made using 3 test wells for each test compound and for each concentration.

After 48 hours, for measurement of the percentages of viable cells, a reagent SF for determination of the number of viable cells (NACALAI TESQUE, INC.) was added at 10 µL/well, cells were gently cultured under culture conditions of 37° C. and 5% $CO_2$, and then a coloring reaction was performed. Subsequently, absorbance was measured at 450 nm using a measuring device ARVO (PerkinElmer Co., Ltd.).

Figure 2B:
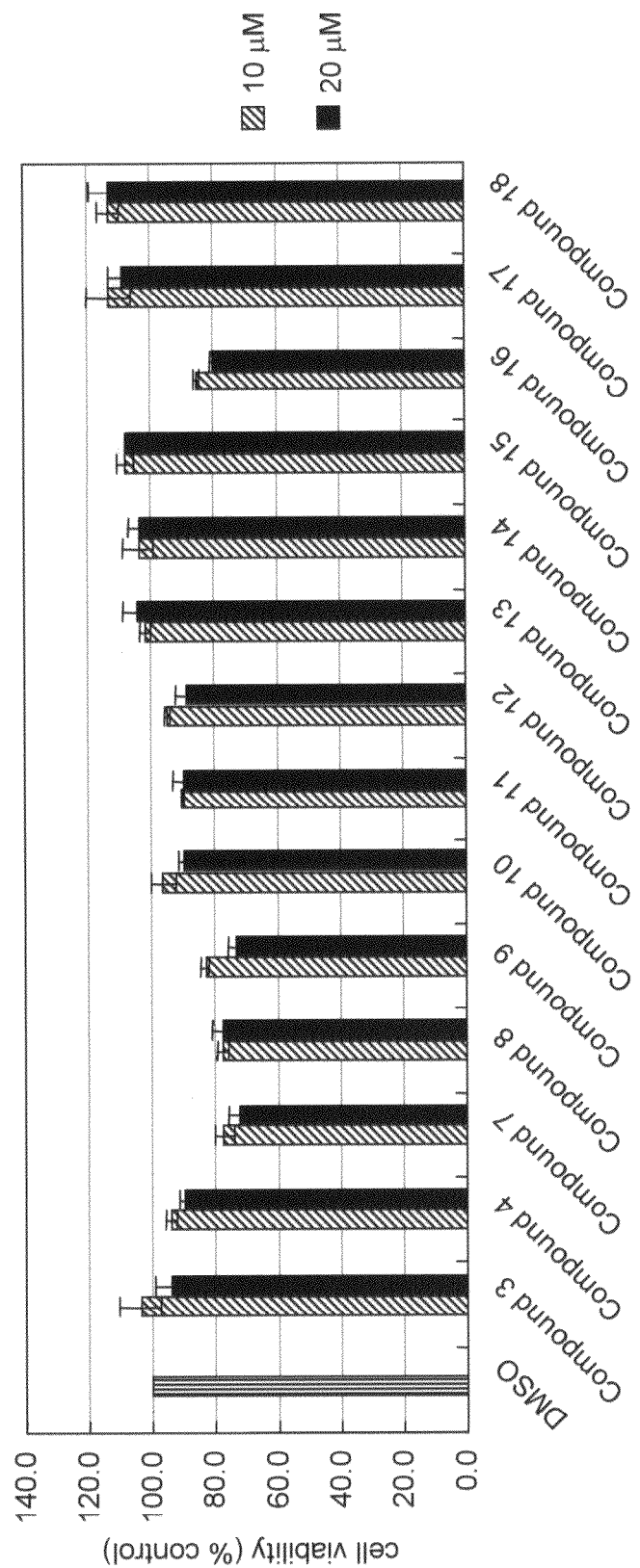
FIG. 2B shows percentages for viable LuHCV cells as obtained by a method similar to that in FIG. 1B. Values shown herein were calculated on a percentage basis, with total viable cells upon addition of DMSO (used as a control test substance) designated as 100%.
Figure 2B:
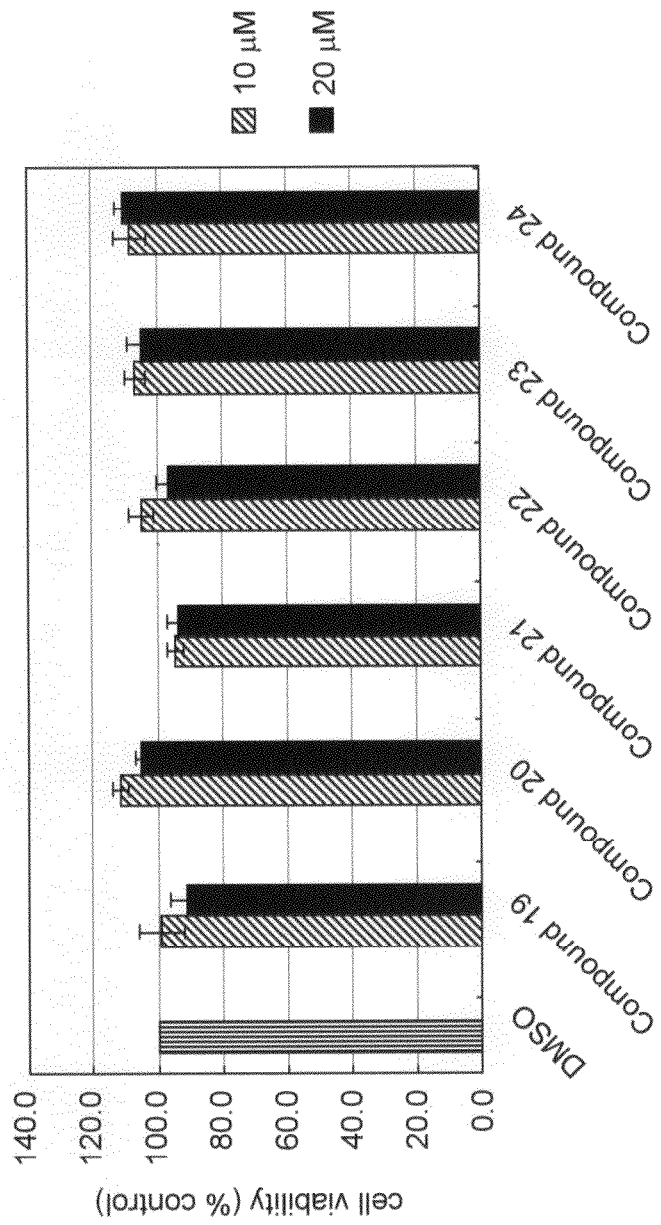

At this time, as a background absorbance, measurement was also performed for wells containing test compounds (or containing DMSO used as a control), but containing no cells. Each of the thus obtained background numerical values was deducted from the absorbance of a cell-containing well (measured for the same compound at the same concentration). The resulting value was designated as actual measurement of number of viable cells containing no background. Based on the thus obtained actual numbers of viable cells, an average value for each test compound at each concentration was calculated. By using a value measured upon addition of DMSO used as a control test substance designated as 100%, the percentage of the number of viable cells for each test compound was calculated. Table 1-2 and FIG. 2B show the percentage of the number of viable cells (cell viability (% control)) for each test compound at each concentration.

The results demonstrated that no significant decreases in cell survival rate were observed in most compounds tested. This indicates that under the conditions of Example 2A, these compounds completely lack cytotoxicity or have weak cytotoxicity if they have such activity. Specifically, the results obtained in Example 2A indicated that the test compounds purely suppressed the expression of the HCV protein.

TABLE 1

Table 1-1

| compound (µM) | luc activity (% control) | |
| --- | --- | --- |
| | 20 | 10 |
| Compound 3 | 43.23 | 69.31 |
| Compound 4 | 44.50 | 65.79 |
| Compound 7 | 16.37 | 30.70 |
| Compound 8 | 57.97 | 55.66 |
| Compound 9 | 26.03 | 33.65 |
| Compound 10 | 26.88 | 41.18 |
| Compound 11 | 29.76 | 35.77 |
| Compound 12 | 28.57 | 32.81 |
| Compound 13 | 28.46 | 34.15 |
| Compound 14 | 14.78 | 30.30 |

TABLE 1-continued

| Compound 15 | 37.60 | 45.76 |
| --- | --- | --- |
| Compound 16 | 48.90 | 58.12 |
| Compound 17 | 17.55 | 26.15 |
| Compound 18 | 22.00 | 26.83 |
| Compound 19 | 33.45 | 50.97 |
| Compound 20 | 22.67 | 48.26 |
| Compound 21 | 34.03 | 56.76 |
| Compound 22 | 21.88 | 42.61 |
| Compound 23 | 49.35 | 64.05 |
| Compound 24 | 39.44 | 56.39 |

Table 1-2

| compound (µM) | viability (% control) | |
| --- | --- | --- |
| | 20 | 10 |
| Compound 3 | 93.82 | 103.79 |
| Compound 4 | 89.76 | 93.86 |
| Compound 7 | 71.85 | 76.97 |
| Compound 8 | 77.81 | 77.35 |
| Compound 9 | 73.39 | 82.79 |
| Compound 10 | 89.38 | 96.19 |
| Compound 11 | 89.20 | 89.95 |
| Compound 12 | 88.78 | 94.69 |
| Compound 13 | 104.05 | 101.56 |
| Compound 14 | 103.76 | 103.81 |
| Compound 15 | 107.33 | 107.86 |
| Compound 16 | 79.86 | 85.21 |
| Compound 17 | 108.81 | 112.89 |
| Compound 18 | 113.41 | 113.01 |
| Compound 19 | 91.02 | 99.02 |
| Compound 20 | 105.35 | 111.50 |
| Compound 21 | 93.56 | 94.44 |
| Compound 22 | 96.39 | 104.65 |
| Compound 23 | 104.93 | 106.72 |
| Compound 24 | 110.15 | 108.20 |

Example 3A

Analysis of HCV Protein Expression-Suppressing Activity of Compound 5

LuHCV cells were plated onto 10-cm dishes at $1\times10^6$ cells/dish and then incubated overnight or longer. Subsequently, Compound 5 dissolved in DMSO was added at a final concentration of 20 µM. Cells were further gently cultured under culture conditions of 37° C. and 5% $CO_2$. DMSO alone was added to a control dish. At 14 hours and 60 hours after addition of Compound 5, cells were collected. Cells were lysed using a cell lysis solution (25 mM $NaPO_4$ (pH 7.5), 150 mM NaCl, 1% Triton X-100, 1 mM EDTA, 20% glycerol, and protease inhibitor cocktail (Roche Diagnostics)), so that cell extracts were obtained. With the use of the thus obtained cell extracts (10 µg each), expression analysis was performed by Western blotting for an HCV-NS5A protein (an antibody was purchased from Virogen) and β-actin (an antibody was purchased from Sigma).

Figure 3A:
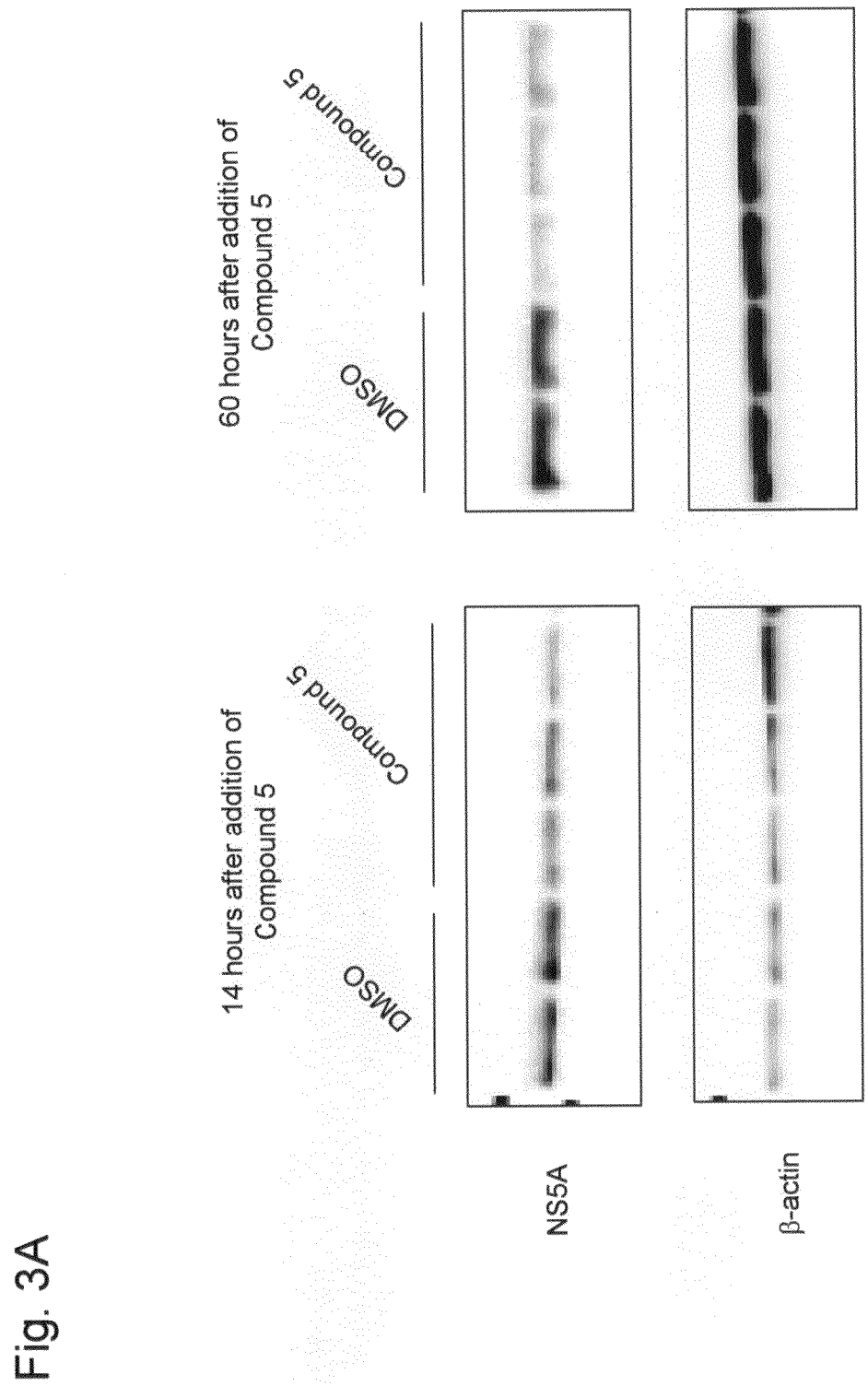
FIG. 3A shows the translation-suppressing effects of a compound of the present invention on HCV protein. During LuHCV cell culture, Compound 5 or DMSO as a control test compound was added, cells were cultured for each time length shown in the figure, and then immunoblotting was performed using anti-NS5A antibody or anti-β-actin antibody. Thus, NS5A expression upon addition of Compound 5 was examined.

FIG. 3A shows the results. At 14 hours and 60 hours after addition of Compound 5, no change was observed in the expression level of β-actin, regardless of the presence or the absence of Compound 5. However, a decrease in the expression level of NS5A was observed in cells to which Compound 5 had been added.

This suggests that Compound 5 tested herein can efficiently suppress the expression of the HCV protein without adversely affecting normal cell functions.

Example 3B

Effects of Compound 5 on the Replication and Stability of HCV RNA

LuHCV cells were plated onto 10-cm dishes at $1\times10^6$ cells/dish and then incubated overnight or longer. Subsequently, Compound 5 dissolved in DMSO was added at a final concentration of 20 µM. Cells were further gently cultured under culture conditions of 37° C. and 5% $CO_2$. DMSO alone was added to a control dish. At 14 hours and 60 hours after addition of Compound 5, cells were collected and then total RNA was extracted using Sepasol-RNA (NACALAI TESQUE, INC.). cDNA was synthesized using SuperScript II reverse transcriptase (Invitrogen) and oligo-dTprimer (Promega) or random primers (Invitrogen Corporation). PCR was performed using the thus synthesized cDNA as a template, NS5A-specific primers (5'-AGTTTTTCACGGAG-GTGGATGGG-3' (SEQ ID NO: 1) and 5'-GTCCGGGTTCT-TCCAAGACTCTA-3' (SEQ ID NO: 2)), GAPDH primers (5'-ACGGATTTGGTCGTATTGGG-3' (SEQ ID NO: 3) and 5'-GTAGTTGAGGTCAATGAAGGGGTC-3' (SEQ ID NO: 4)), and PrimeSTAR HS DNA polymerase (Takara Bio Inc.). After DNA amplification reaction, agarose gel electrophoresis and ethidium bromide staining were performed. The expression level of each gene was evaluated using a UV transilluminator.

Figure 3B:
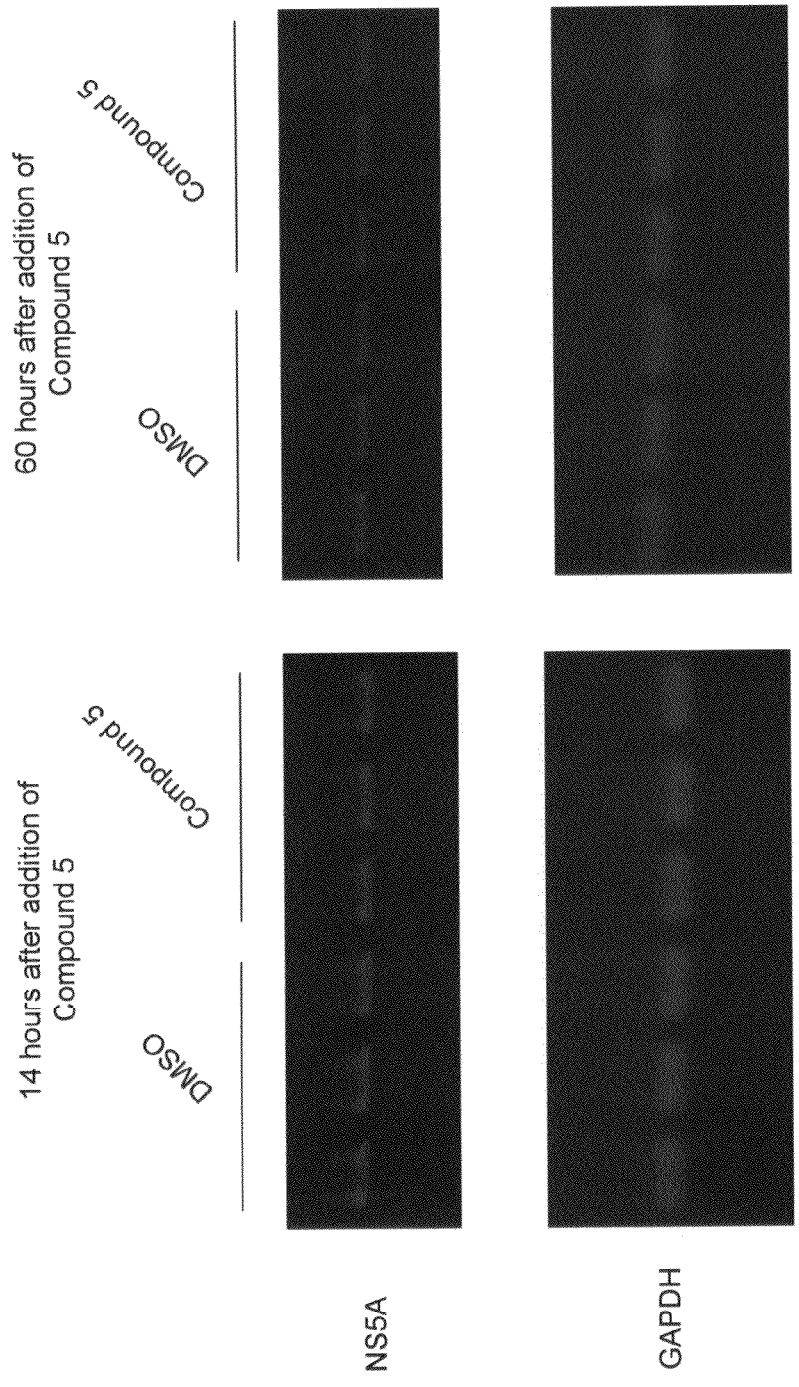
FIG. 3B shows that the compound of the present invention does not have effects on HCV-RNA replication. During LuHCV cell culture, Compound 5 or DMSO as a control test compound was added, cells were cultured for each time length shown in the figure, and then the amount of NS5A-RNA upon addition of Compound 5 was examined by the RT-PCR method using specific primers against NS5A or specific primers against GAPDH.

FIG. 3B shows the results. At 14 hours and 60 hours after addition of Compound 5, no quantitative change was observed for both NS5A and GAPDH regardless of the addition of Compound 5.

This indicates that Compound 5 tested herein has no effects on the replication and stability of HCV-RNA.

Based on the results of both Example 3A and Example 3B, it was revealed that Compound 5 can suppress the expression of the HCV protein at the translation level without affecting the replication or stability of HCV-RNA.

Example 4

Effects of Compound 5 on the Growth of LuHCV Cells

LuHCV cells were plated onto a 6-well plate at $5\times10^4$ cells/1 mL/well and then incubated overnight. On the next day of plating of LuHCV cells, a medium containing Compound 5 with a concentration twice the final test concentration was added at 1 mL/well. The final concentration of Compound 5 was 20 µM. Cells were gently cultured under culture conditions of 37° C. and 5% $CO_2$. After addition of Compound 5, cells were collected from 3 wells at 0, 6, 12, 24, 36, and 48 hours later, the number of viable cells per well was measured using a hemocytometer, and then the average value was calculated. Wells to which only DMSO had been added were used as control wells.

Figure 4:
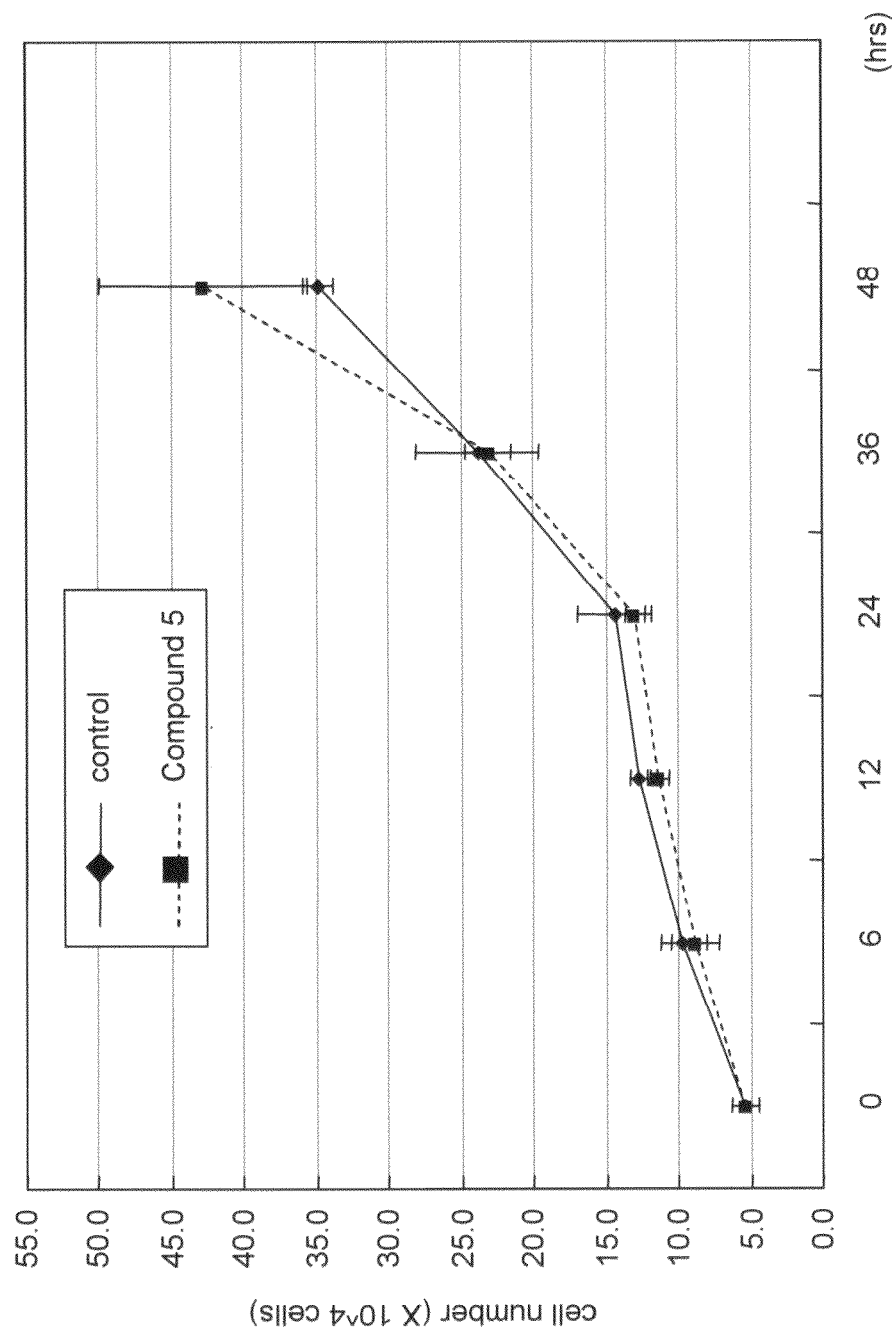
FIG. 4 shows that Compound 5 completely lacks the ability to suppress proliferation and cytotoxicity for LuHCV cells.

FIG. 4 shows the results. Almost no differences were observed in the number of cells at each time point between controls to which DMSO had been added and cells to which Compound 5 had been added. It was revealed by the results that Compound 5 does not suppress the growth of LuHCV cells and has no cytotoxicity.

Example 5

Evaluation of Anti-Viral Activity Against Influenza Virus

For the test compounds disclosed in the present invention, the effects of suppressing the replication of influenza A virus (PR-8) were evaluated. MDCK cells were plated onto 6-well plates at $5\times10^5$ cells/well and then incubated overnight. Test compounds were each dissolved in dimethyl sulfoxide (DMSO) and dilution series were prepared using DMSO, if necessary. On the next day of plating of MDCK cells, a test compound was added at a final concentration of 14 µM, simultaneously with the addition of influenza A virus (PR-8). Cells were gently cultured under culture conditions of 72 hours, 37° C., and 5% $CO_2$. After 72 hours of culture, cells were washed twice with 2 mL of PBS (−). Subsequently, after 30 minutes of fixation in a 15% acetic acid/85% ethanol solution, crystal violet staining was performed.

Figure 5:
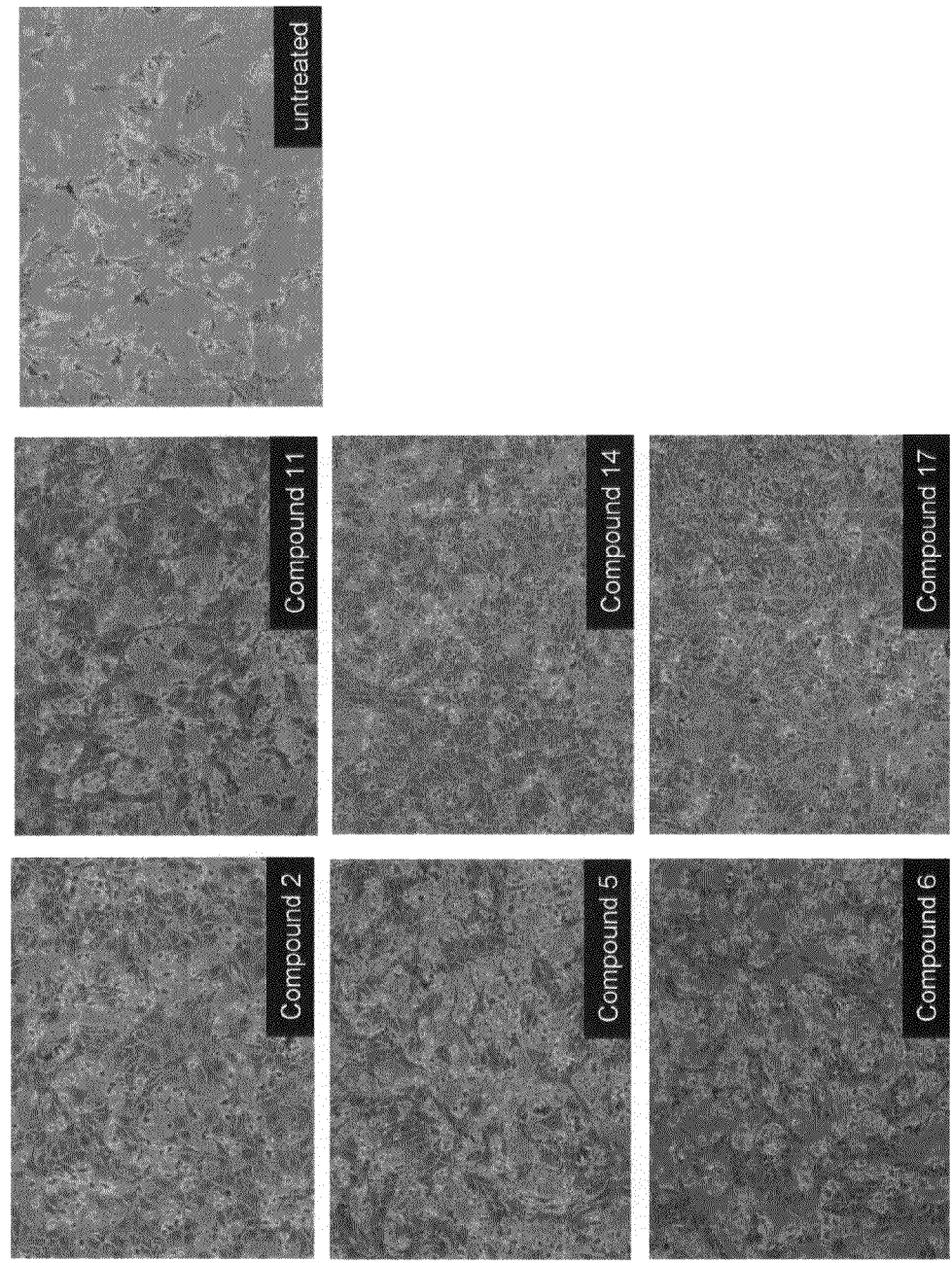
FIG. 5 shows that the compounds of the present invention also have antiviral effects against influenza virus. DMSO control MDCK cells to which no test compound had been added were infected with influenza virus, died at high rates, and were detached from the plate. On the other hand, in the test compound groups, cell detachment due to cell death was suppressed.

Cells after staining were observed under a phase-contrast microscope. As shown in FIG. 5, DMSO-control MDCK cells, to which no test compound had been added, were infected with the influenza virus, died at a high rate, and dissociated from the plate. On the other hand, cell dissociation due to cell death was suppressed in the case of groups to which the test compounds had been added.

This demonstrates that the test compounds also have antiviral effects on influenza viruses.

Example 6

Suppression of Cell Death Due to Influenza Virus Infection

MDCK cells were plated onto 96-well plates at $1\times10^4$ cells/100 µL/well and then incubated overnight. Test compounds were each dissolved in DMSO and dilution series were prepared using DMSO, if necessary. On the next day of plating of MDCK cells, a test compound was diluted with a medium for influenza virus infection and then culture media in the 96-well plates were replaced with it. Subsequently, an influenza virus was added to test wells. Cells were gently cultured under culture conditions of 48 hours, 37° C., and 5% $CO_2$ (the final concentrations of the test compounds: 0, 5, and 10 µM). At this time, analysis was made using 3 test wells for each test compound and for each concentration.

After 48 hours, for measurement of the percentages of viable cells, a reagent SF for determination of the number of viable cells (NACALAI TESQUE, INC.) was added at 10 µL/well, cells were gently cultured under culture conditions of 37° C. and 5% $CO_2$, and then a coloring reaction was performed. Subsequently, absorbance was measured at 450 nm using a measuring device ARVO (PerkinElmer Co., Ltd.).

At this time, as a background absorbance, measurement was also performed for wells containing test compounds (or containing DMSO used as a control), but containing no cells. Each of the thus obtained background numerical values was deducted from the absorbance of a cell-containing well (measured for the same compound at the same concentration). The resulting value was designated as actual measurement of number of viable cells containing no background. Based on the thus obtained actual numbers of viable cells, an average value for each test compound at each concentration was calculated. By using a value calculated upon addition of DMSO used as a control test substance as 100%, the percentage of the number of viable cells for each test compound was calculated.

Figure 6:
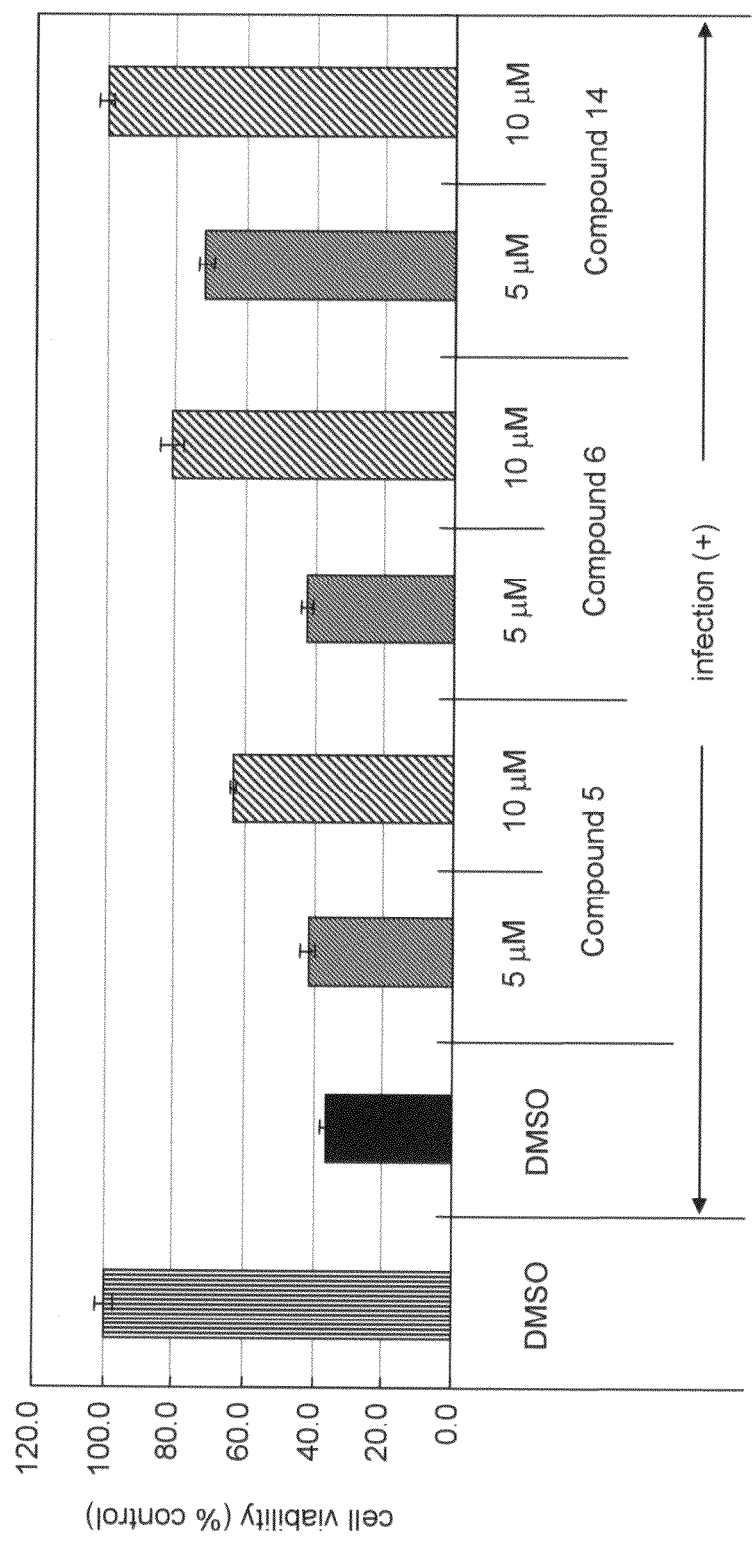
FIG. 6 shows the cell death-suppressing effects of the compounds of the present invention on cells infected with influenza virus. In the absence of test compounds, influenza virus infection resulted in the percentage of viable cells of 40% or less. On the other hand, it was revealed that cell death was reduced with the addition of Compound 5, Compound 6, or Compound 14.

FIG. 6 and Table 2 show the results. It was revealed that, in the absence of the test compounds, the percentages of viable cells were each found to be 40% or less because of influenza virus infection; but cell death was decreased by the addition of Compound 5, Compound 6, or Compound 14.

TABLE 2

| conc. (μM) | control | Compound 5 | | Compound 6 | | Compound 14 | | control |
|---|---|---|---|---|---|---|---|---|
| | | 10 | 5 | 10 | 5 | 10 | 5 | |
| infection | + | + | + | + | + | + | + | − |
| viability (% control) | 36.7 ± 1.3 | 63.1 ± 0.9 | 41.8 ± 2.2 | 80.9 ± 3.2 | 42.1 ± 1.5 | 100.0 ± 2.0 | 71.6 ± 2.2 | 100.0 ± 2.6 |

Example 7

Toxicity Test by Repeated In Vivo Administration of Compound 5

A conditioning period of one week (day-7 to day-1) was provided for mice (Crlj/CD1 (ICR) mice, male, 5-week-old), and then the mice were grouped based on the mean body weight on the day before the initiation of the test. Also, the dose of Compound 5 was calculated based on the mean body weight (day-1). There were 2 groups to which Compound 5 was administered: a placebo-administered group (n=6) to which a placebo was administered and a Compound 5-administered group (n=6) to which Compound 5 was administered. On the days of administration (day 00 to day 07), the test compound formulated using 0.5% carboxymethyl cellulose was administered via oral administration for 7 days in a row. Symptoms were observed during the administration period.

During the test period, the body weight of each mouse was weighed on day −7, day −3, day −1, day 4, and day 7. Symptoms were observed at ½, 1, 2, 3, and 4 hours after administration on the day of initiation of administration of Compound 5 and were observed once a day from day 2 after the initiation of administration.

As a result, throughout 7 days of the administration period, no dead mice were observed among the group to which Compound 5 had been administered at 1000 mg/kg/day, compared with the placebo group; and the level at which no adverse effect is observed was 1000 mg/kg or more.

Figure 7:
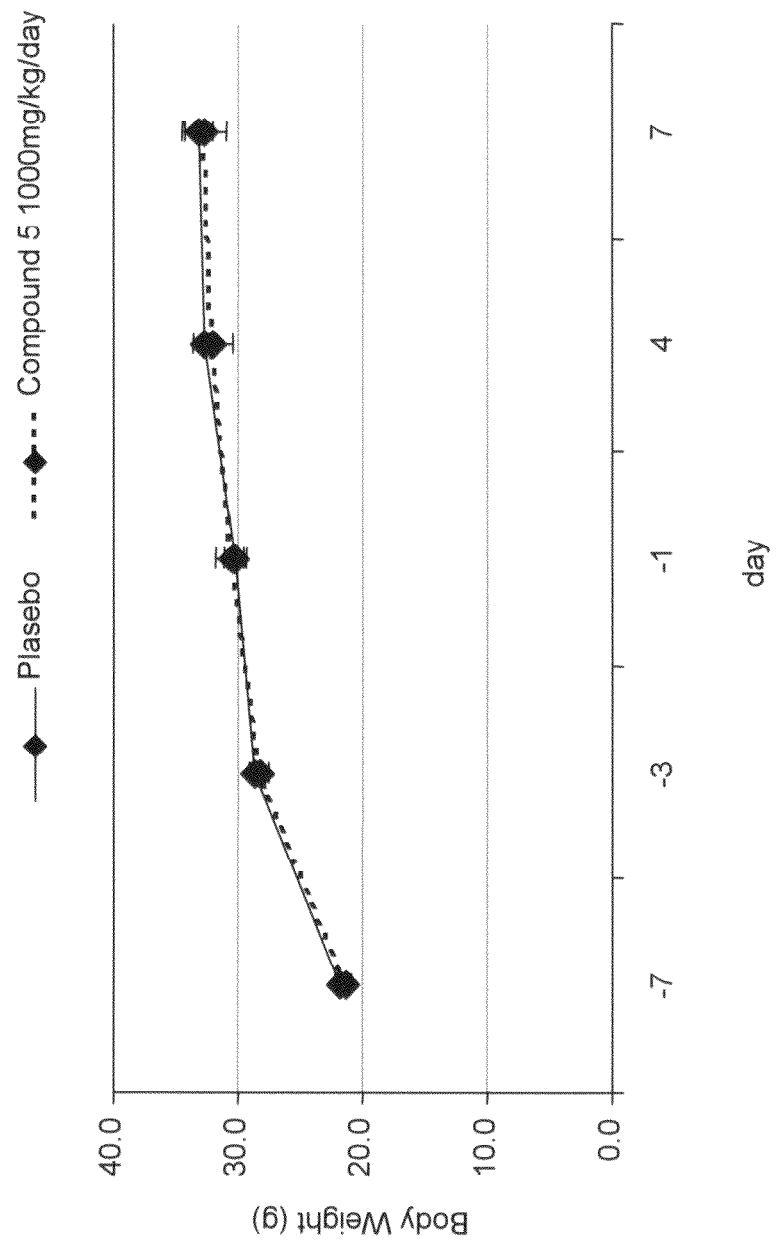
FIG. 7 shows the results of an in vivo toxicity test for Compound 5 of the present invention. Even after 7 days of repeated administration at 1000 mg/kg/day, no cases of death were observed. The test compound group showed a steady body weight increase that was completely the same as that of the control vehicle group (the placebo group).

Regarding changes in body weight in each group, no significant difference was present between the placebo group and the Compound 5-administered group; steady body weight gain was observed during the administration period; and each group maintained conditions of good health (FIG. 7 and Table 3).

| Group | Animal No. | BW −7 | −3 | −1 | 4 | 7 |
|---|---|---|---|---|---|---|
| | | Table 3-1 | | | | |
| Placebo | 1 | 22.0 | 29.0 | 31.5 | 32.5 | 33.5 |
| | 2 | 22.0 | 29.0 | 30.0 | 32.0 | 32.0 |

-continued

| Group | Animal No. | BW −7 | −3 | −1 | 4 | 7 |
|---|---|---|---|---|---|---|
| | 3 | 21.0 | 28.0 | 28.5 | 32.0 | 32.0 |
| | 4 | 21.5 | 28.0 | 29.5 | 31.0 | 31.0 |
| | 5 | 22.0 | 29.5 | 31.5 | 34.0 | 34.0 |
| | 6 | 22.0 | 28.0 | 31.0 | 35.0 | 36.0 |
| Compound 5 1000 mg kg/day | 7 | 21.5 | 28.0 | 29.5 | 31.0 | 31.5 |
| | 8 | 22.0 | 29.0 | 31.5 | 31.5 | 32.0 |
| | 9 | 21.5 | 28.5 | 31.0 | 32.0 | 32.5 |
| | 10 | 21.5 | 27.5 | 30.0 | 32.0 | 32.5 |
| | 11 | 21.0 | 28.0 | 30.0 | 32.5 | 33.5 |
| | 12 | 21.0 | 28.0 | 31.0 | 33.0 | 34.5 |
| | | Table 3-2 | | | | |
| Mean | Placebo | 21.8 | 28.6 | 30.3 | 32.8 | 33.1 |
| | Compound 5 | 21.4 | 28.2 | 30.5 | 32.0 | 32.8 |
| SD | Placebo | 0.4 | 0.7 | 1.2 | 1.5 | 1.8 |
| | Compound 5 | 0.4 | 0.5 | 0.8 | 0.7 | 1.1 |
| t-test | Compound 5 | 0.177 | 0.253 | 0.782 | 0.288 | 0.706 |

This means that the test compound has no in vivo toxicity.

CONCLUSION

As described above, it was demonstrated that the compounds of the present invention have anti-viral activity against HCV and influenza viruses and do not exert significant cytotoxicity or in vivo toxicity.

INDUSTRIAL APPLICABILITY

As a result of synthesis of and screening for many compounds, the present inventors have discovered that the compounds having the structure of formula I have excellent anti-RNA virus activity. The number of antiviral agents that currently can be used is very small. Medicines according to the present invention can present new therapeutic options. Specifically, the present invention can provide a new option for treatment of RNA virus infections.

The invention claimed is:

1. A compound selected from the group consisting of:

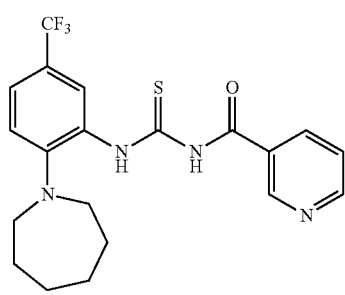

,

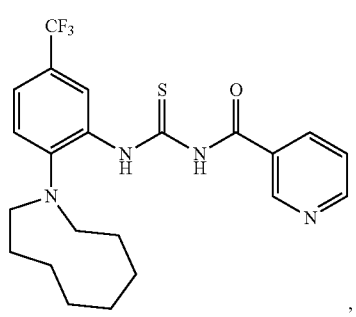

,

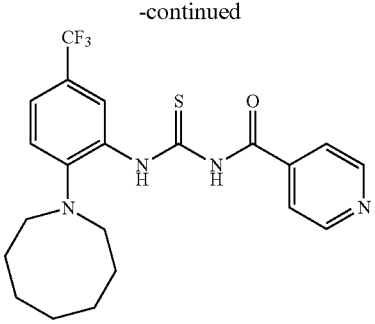

,

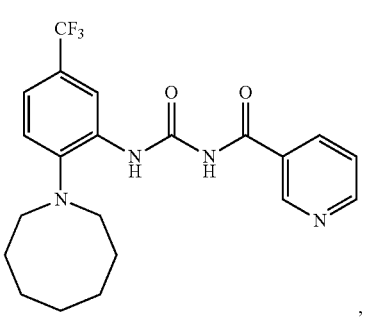

,

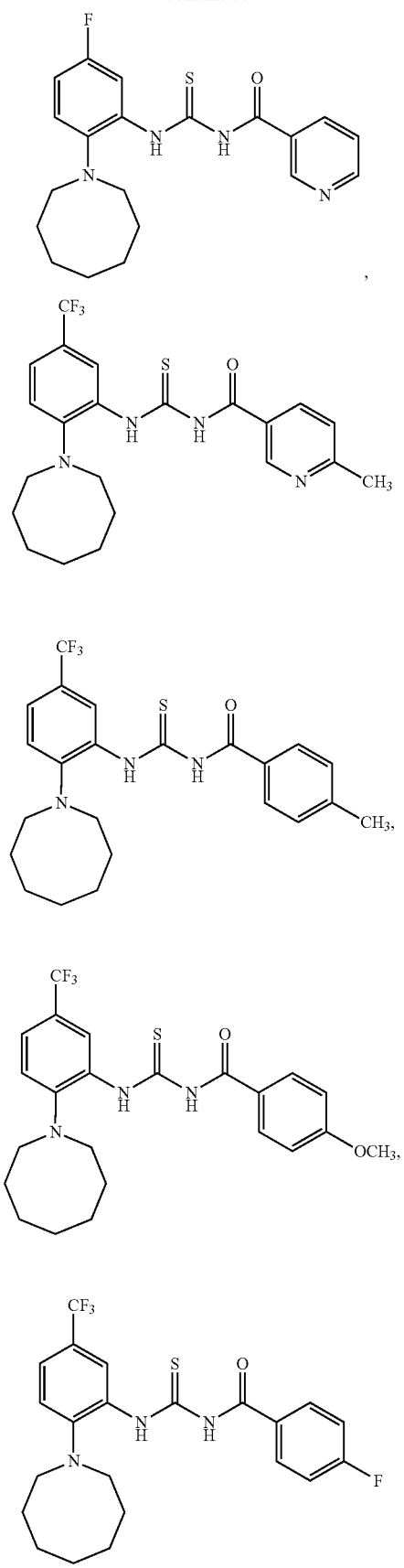
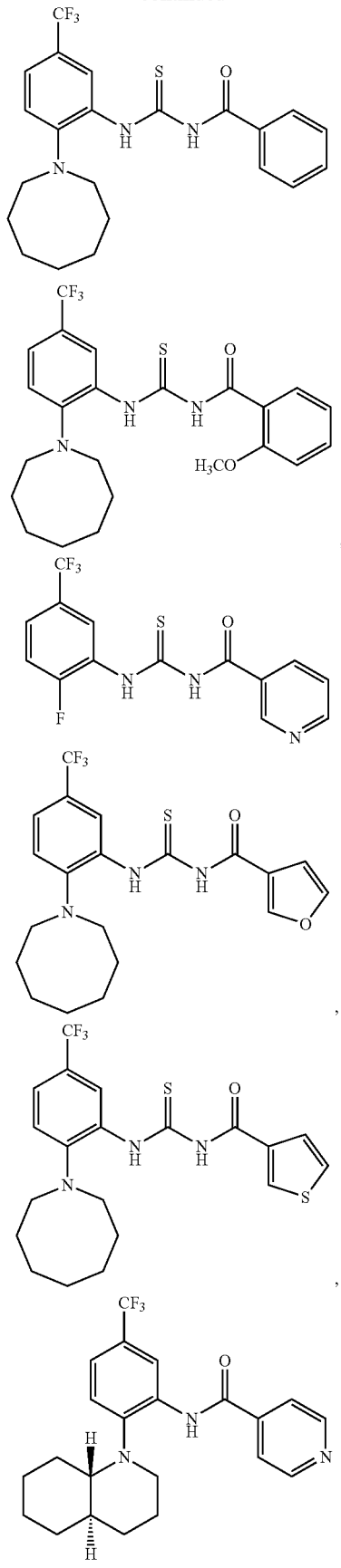

-continued
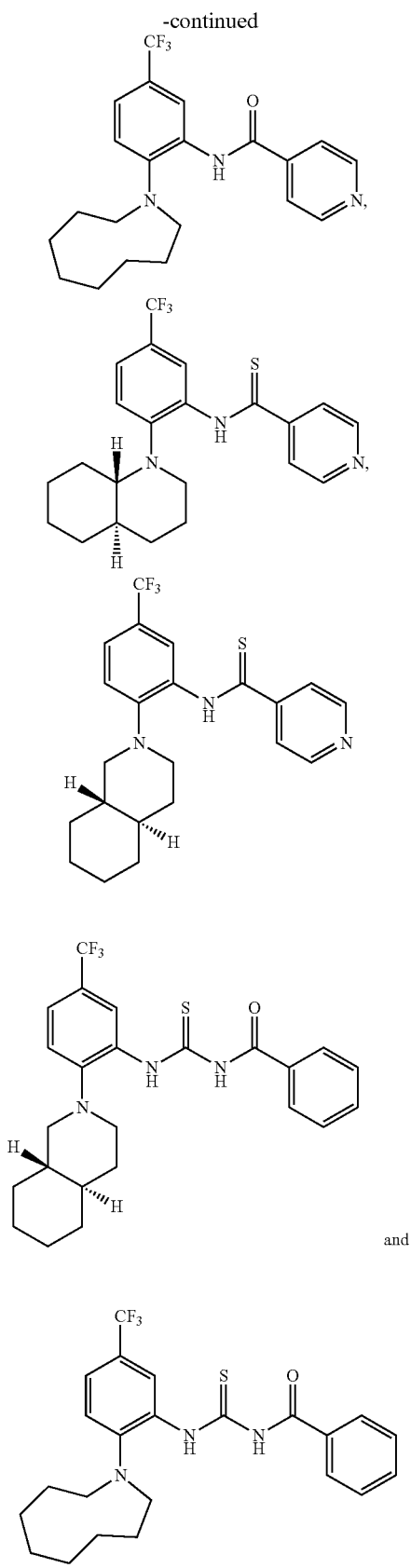
or a pharmaceutically acceptable salt thereof, or a hydrate thereof.
2. The compound of claim 1, wherein the compound is selected from the group consisting of:
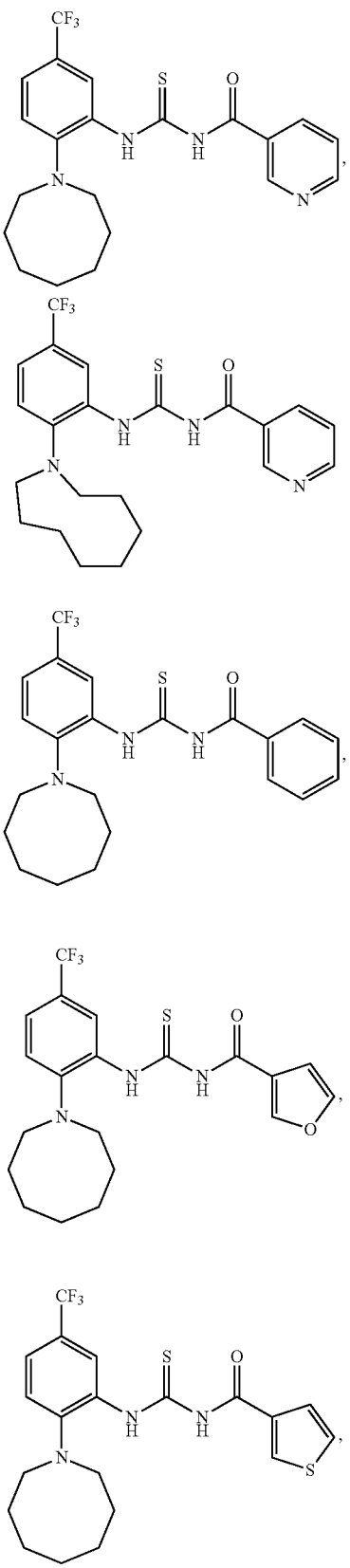

-continued
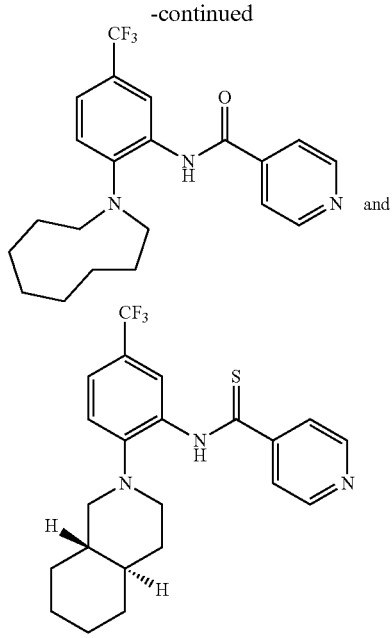
and
or a pharmaceutically acceptable salt thereof, or a hydrate thereof.
* * * * *